(12) United States Patent
Schmitz et al.

(10) Patent No.: US 7,959,577 B2
(45) Date of Patent: Jun. 14, 2011

(54) METHOD, SYSTEM, AND APPARATUS FOR NEURAL LOCALIZATION

(75) Inventors: Gregory P. Schmitz, Los Gatos, CA (US); Michael P. Wallace, Pleasanton, CA (US); Jeffery L. Bleich, Palo Alto, CA (US); Eric C. Miller, Los Gatos, CA (US)

(73) Assignee: Baxano, Inc., San Jose, CA (US)

( * ) Notice: Subject to any disclaimer, the term of this patent is extended or adjusted under 35 U.S.C. 154(b) by 88 days.

(21) Appl. No.: 12/060,229

(22) Filed: Mar. 31, 2008

(65) Prior Publication Data
US 2009/0069709 A1 Mar. 12, 2009

Related U.S. Application Data

(60) Provisional application No. 61/020,670, filed on Jan. 11, 2008, provisional application No. 61/017,512, filed on Dec. 28, 2007, provisional application No. 60/976,029, filed on Sep. 28, 2007, provisional application No. 60/970,458, filed on Sep. 6, 2007.

(51) Int. Cl.
*A61B 5/05* (2006.01)

(52) U.S. Cl. ............ 600/554; 607/48; 607/117; 607/118

(58) Field of Classification Search ................ 600/372, 600/377, 393, 547, 554, 587; 607/46, 48, 607/115–118, 148
See application file for complete search history.

(56) References Cited

U.S. PATENT DOCUMENTS

| | | | |
|---|---|---|---|
| 184,804 A | 11/1876 | Stohlmann | |
| 289,104 A | 11/1883 | How | |
| 863,389 A | 8/1907 | Harkin | |
| 1,039,487 A | 9/1912 | Casebolt | |
| 1,201,467 A | 10/1916 | Hoglund | |
| 1,374,638 A | 4/1921 | De Cew et al. | |
| 1,543,195 A | 6/1925 | Thygesen | |
| 1,690,812 A | 11/1928 | Bertels | |

(Continued)

FOREIGN PATENT DOCUMENTS

DE 3209403 A1 9/1983

(Continued)

OTHER PUBLICATIONS

Tomita et al., "The Use of the T-Saw for Expansive Midline laminoplasty in the Treatment of Cervical Myelopathy," Orthopedics and Traumatology, No. 3, pp. 169-178, 2002.

(Continued)

*Primary Examiner* — Max Hindenburg
*Assistant Examiner* — Rene Towa
(74) *Attorney, Agent, or Firm* — Shay Glenn LLP

(57) ABSTRACT

Described herein are devices, systems and methods for determining if a nerve is nearby a device or a region of a device. In general, a device for determining if a nerve is nearby a device includes an elongate body having an outer surface with one or more bipole pairs arranged on the outer surface. Bipole pairs may also be referred to as tight bipoles. The bipole pairs may be arranged as a bipole network, and may include a cathode and an anode that are spaced relatively close together to form a limited broadcast field. In general, the broadcast filed is a controlled or "tight" broadcast field that extends from the bipole pair(s). Methods of using these devices and system are also described.

13 Claims, 31 Drawing Sheets

U.S. PATENT DOCUMENTS

| | | |
|---|---|---|
| 1,938,200 A | 12/1933 | Wells |
| 2,243,757 A | 5/1941 | Kohls et al. |
| 2,269,749 A | 1/1942 | Wilkie |
| 2,372,553 A | 3/1945 | Coddington |
| 2,437,697 A | 3/1948 | Kalom |
| 2,516,882 A | 8/1950 | Kalom |
| 2,704,064 A | 5/1955 | Fizzell |
| 2,820,281 A | 1/1958 | Amsen |
| 2,843,128 A | 7/1958 | Storz |
| 2,982,005 A | 5/1961 | Booth |
| RE025,582 E | 5/1964 | Davies |
| 3,150,470 A | 9/1964 | Barron |
| 3,389,447 A | 6/1968 | Theobald et al. |
| 3,491,776 A | 1/1970 | Fleming |
| 3,495,590 A | 2/1970 | Zeiller |
| 3,528,152 A | 9/1970 | Funakubo et al. |
| 3,624,484 A | 11/1971 | Colyer |
| 3,640,280 A | 2/1972 | Slanker et al. |
| 3,651,844 A | 3/1972 | Barnes |
| 3,664,329 A | 5/1972 | Naylor |
| 3,682,162 A | 8/1972 | Colyer |
| 3,699,729 A | 10/1972 | Garvey et al. |
| 3,752,166 A | 8/1973 | Lyon et al. |
| 3,774,355 A | 11/1973 | Dawson et al. |
| 3,830,226 A | 8/1974 | Staub et al. |
| 3,835,859 A | 9/1974 | Roberts et al. |
| 3,956,858 A | 5/1976 | Catlin et al. |
| 3,957,036 A | 5/1976 | Normann |
| 3,978,862 A | 9/1976 | Morrison |
| 4,015,931 A | 4/1977 | Thakur |
| 4,099,519 A | 7/1978 | Warren |
| 4,108,182 A | 8/1978 | Hartman et al. |
| 4,160,320 A | 7/1979 | Wikoff |
| 4,172,440 A | 10/1979 | Schneider et al. |
| 4,203,444 A | 5/1980 | Bonnell et al. |
| 4,207,897 A | 6/1980 | Lloyd et al. |
| 4,259,276 A | 3/1981 | Rawlings |
| 4,405,061 A | 9/1983 | Bergandy |
| D273,806 S | 5/1984 | Bolesky et al. |
| 4,464,836 A | 8/1984 | Hissa |
| 4,502,184 A | 3/1985 | Karubian |
| 4,515,168 A | 5/1985 | Chester et al. |
| 4,545,374 A | 10/1985 | Jacobson |
| 4,573,448 A | 3/1986 | Kambin |
| 4,580,545 A | 4/1986 | Dorsten |
| 4,590,949 A | 5/1986 | Pohndorf |
| 4,616,660 A | 10/1986 | Johns |
| 4,621,636 A | 11/1986 | Fogarty |
| 4,625,725 A | 12/1986 | Davison et al. |
| 4,660,571 A | 4/1987 | Hess et al. |
| 4,678,459 A | 7/1987 | Onik et al. |
| 4,690,642 A | 9/1987 | Kyotani |
| 4,700,702 A | 10/1987 | Nilsson |
| 4,709,699 A | 12/1987 | Michael et al. |
| 4,741,343 A | 5/1988 | Bowman |
| 4,794,931 A | 1/1989 | Yock |
| 4,808,157 A | 2/1989 | Coombs |
| 4,817,628 A | 4/1989 | Zealear et al. |
| 4,856,193 A | 8/1989 | Grachan |
| 4,867,155 A | 9/1989 | Isaacson |
| 4,872,452 A | 10/1989 | Alexson |
| 4,873,978 A | 10/1989 | Ginsburg |
| 4,883,460 A | 11/1989 | Zanetti |
| 4,894,063 A | 1/1990 | Nashe |
| RE33,258 E | 7/1990 | Onik et al. |
| 4,943,295 A | 7/1990 | Hartlaub et al. |
| 4,957,117 A | 9/1990 | Wysham |
| 4,962,766 A | 10/1990 | Herzon |
| 4,973,329 A | 11/1990 | Park et al. |
| 4,990,148 A | 2/1991 | Worrick, III et al. |
| 4,994,036 A | 2/1991 | Biscoping et al. |
| 4,994,072 A | 2/1991 | Bhate et al. |
| 4,995,200 A | 2/1991 | Eberhart |
| 5,019,082 A | 5/1991 | Frey et al. |
| 5,025,787 A | 6/1991 | Sutherland et al. |
| 5,026,379 A | 6/1991 | Yoon |
| 5,026,386 A | 6/1991 | Michelson |
| 5,078,137 A | 1/1992 | Edell et al. |
| 5,089,003 A | 2/1992 | Fallin et al. |
| 5,100,424 A | 3/1992 | Jang et al. |
| 5,108,403 A | 4/1992 | Stern |
| 5,125,928 A | 6/1992 | Parins et al. |
| 5,147,364 A | 9/1992 | Comparetto |
| 5,152,749 A | 10/1992 | Giesy et al. |
| 5,161,534 A | 11/1992 | Berthiaume |
| 5,163,939 A | 11/1992 | Winston |
| 5,176,649 A | 1/1993 | Wakabayashi |
| 5,178,145 A | 1/1993 | Rea |
| 5,178,161 A | 1/1993 | Kovacs |
| 5,191,888 A | 3/1993 | Palmer et al. |
| 5,195,507 A | 3/1993 | Bilweis |
| 5,201,704 A | 4/1993 | Ray |
| 5,215,105 A | 6/1993 | Kizelshteyn et al. |
| 5,219,358 A | 6/1993 | Bendel et al. |
| 5,242,418 A | 9/1993 | Weinstein |
| 5,250,035 A | 10/1993 | Smith et al. |
| 5,255,691 A | 10/1993 | Otten |
| 5,271,415 A | 12/1993 | Foerster et al. |
| 5,281,218 A | 1/1994 | Imran |
| 5,284,153 A | 2/1994 | Raymond et al. |
| 5,284,154 A | 2/1994 | Raymond et al. |
| 5,300,077 A | 4/1994 | Howell |
| 5,325,868 A | 7/1994 | Kimmelstiel |
| 5,341,807 A | 8/1994 | Nardella |
| 5,351,679 A | 10/1994 | Mayzels et al. |
| 5,353,784 A | 10/1994 | Nady-Mohamed |
| 5,353,789 A | 10/1994 | Schlobohm |
| 5,353,802 A | 10/1994 | Ollmar |
| 5,360,441 A | 11/1994 | Otten |
| 5,365,928 A | 11/1994 | Rhinehart et al. |
| 5,374,261 A | 12/1994 | Yoon |
| 5,383,879 A | 1/1995 | Phillips |
| 5,385,146 A * | 1/1995 | Goldreyer ............... 600/374 |
| 5,387,218 A | 2/1995 | Meswania |
| 5,396,880 A | 3/1995 | Kagan et al. |
| 5,421,348 A | 6/1995 | Larnard |
| 5,423,331 A | 6/1995 | Wysham |
| 5,437,661 A | 8/1995 | Rieser |
| 5,439,464 A | 8/1995 | Shapiro |
| 5,441,044 A | 8/1995 | Tovey et al. |
| 5,441,510 A | 8/1995 | Simpson et al. |
| 5,454,815 A | 10/1995 | Geisser et al. |
| 5,456,254 A | 10/1995 | Pietroski et al. |
| 5,496,325 A | 3/1996 | McLees |
| 5,512,037 A | 4/1996 | Russell et al. |
| 5,515,848 A | 5/1996 | Corbett, III et al. |
| 5,531,749 A | 7/1996 | Michelson |
| 5,534,009 A | 7/1996 | Lander |
| 5,546,958 A | 8/1996 | Thorud et al. |
| 5,554,110 A | 9/1996 | Edwards et al. |
| 5,555,892 A | 9/1996 | Tipton |
| 5,560,372 A | 10/1996 | Cory |
| 5,562,695 A | 10/1996 | Obenchain |
| 5,571,181 A | 11/1996 | Li |
| 5,582,618 A | 12/1996 | Chin et al. |
| 5,598,848 A | 2/1997 | Swanson et al. |
| 5,620,447 A | 4/1997 | Smith et al. |
| 5,630,426 A | 5/1997 | Eggers et al. |
| 5,634,475 A | 6/1997 | Wolvek |
| 5,643,304 A | 7/1997 | Schechter et al. |
| 5,651,373 A | 7/1997 | Mah |
| 5,656,012 A | 8/1997 | Sienkiewicz |
| 5,680,860 A | 10/1997 | Imran |
| 5,681,324 A | 10/1997 | Kammerer et al. |
| 5,697,889 A | 12/1997 | Slotman et al. |
| 5,709,697 A | 1/1998 | Ratcliff et al. |
| 5,725,530 A | 3/1998 | Popken |
| 5,735,792 A | 4/1998 | Vanden Hoek et al. |
| 5,755,732 A | 5/1998 | Green et al. |
| 5,759,159 A | 6/1998 | Masreliez |
| 5,762,629 A | 6/1998 | Kambin |
| 5,766,168 A | 6/1998 | Mantell |
| 5,769,865 A | 6/1998 | Kermode et al. |
| 5,775,331 A * | 7/1998 | Raymond et al. ............. 600/554 |
| 5,779,642 A | 7/1998 | Nightingale |
| 5,788,653 A | 8/1998 | Lorenzo |
| 5,792,044 A | 8/1998 | Foley et al. |

| | | | | | | |
|---|---|---|---|---|---|---|
| 5,795,308 A | 8/1998 | Russin | | 6,324,432 B1 | 11/2001 | Rigaux et al. |
| 5,800,350 A | 9/1998 | Coppleson et al. | | 6,334,068 B1 | 12/2001 | Hacker |
| 5,803,902 A | 9/1998 | Sienkiewicz et al. | | 6,343,226 B1 | 1/2002 | Sunde et al. |
| 5,803,904 A | 9/1998 | Mehdizadeh | | 6,358,254 B1 | 3/2002 | Anderson |
| 5,807,263 A | 9/1998 | Chance | | 6,360,750 B1 | 3/2002 | Gerber et al. |
| 5,810,744 A | 9/1998 | Chu et al. | | 6,364,886 B1 | 4/2002 | Sklar |
| 5,813,405 A | 9/1998 | Montano, Jr. et al. | | 6,368,324 B1 | 4/2002 | Dinger et al. |
| 5,824,040 A | 10/1998 | Cox et al. | | 6,370,411 B1 | 4/2002 | Osadchy et al. |
| 5,830,151 A | 11/1998 | Hadzic et al. | | 6,370,435 B2 | 4/2002 | Panescu et al. |
| 5,830,157 A | 11/1998 | Foote | | 6,383,509 B1 | 5/2002 | Donovan et al. |
| 5,830,188 A | 11/1998 | Abouleish | | 6,390,906 B1 | 5/2002 | Subramanian |
| 5,833,692 A | 11/1998 | Cesarini et al. | | 6,391,028 B1 | 5/2002 | Fanton et al. |
| 5,836,948 A | 11/1998 | Zucherman et al. | | 6,416,505 B1 | 7/2002 | Fleischman et al. |
| 5,843,110 A | 12/1998 | Dross et al. | | 6,423,071 B1 | 7/2002 | Lawson |
| 5,846,196 A | 12/1998 | Siekmeyer et al. | | 6,423,080 B1 | 7/2002 | Gellman et al. |
| 5,846,244 A | 12/1998 | Cripe | | 6,425,859 B1 | 7/2002 | Foley et al. |
| 5,851,191 A | 12/1998 | Gozani | | 6,425,887 B1 | 7/2002 | McGuckin et al. |
| 5,851,209 A | 12/1998 | Kummer et al. | | 6,436,101 B1 | 8/2002 | Hamada |
| 5,851,214 A | 12/1998 | Larsen et al. | | 6,442,848 B1 | 9/2002 | Dean |
| 5,853,373 A | 12/1998 | Griffith et al. | | 6,451,335 B1 | 9/2002 | Goldenheim et al. |
| 5,865,844 A | 2/1999 | Plaia et al. | | 6,454,767 B2 | 9/2002 | Alleyne |
| 5,868,767 A | 2/1999 | Farley et al. | | 6,464,682 B1 | 10/2002 | Snoke |
| 5,879,353 A | 3/1999 | Terry | | 6,466,817 B1 | 10/2002 | Kaula et al. |
| 5,885,219 A | 3/1999 | Nightengale | | 6,468,289 B1 | 10/2002 | Bonutti |
| 5,895,417 A | 4/1999 | Pomeranz et al. | | 6,470,209 B2 | 10/2002 | Snoke |
| 5,897,583 A | 4/1999 | Meyer et al. | | 6,478,805 B1 | 11/2002 | Marino et al. |
| 5,899,909 A | 5/1999 | Claren et al. | | 6,487,439 B1 | 11/2002 | Skladnev et al. |
| 5,904,657 A | 5/1999 | Unsworth et al. | | 6,488,636 B2 | 12/2002 | Bryan et al. |
| 5,916,173 A | 6/1999 | Kirsner | | 6,491,646 B1 | 12/2002 | Blackledge |
| 5,918,604 A | 7/1999 | Whelan | | 6,500,128 B2 | 12/2002 | Marino |
| 5,919,190 A | 7/1999 | VanDusseldorp | | 6,500,189 B1 | 12/2002 | Lang et al. |
| 5,928,158 A | 7/1999 | Aristides | | 6,512,958 B1 | 1/2003 | Swoyer et al. |
| 5,928,159 A | 7/1999 | Eggers et al. | | 6,516,223 B2 | 2/2003 | Hofmann |
| 5,941,822 A | 8/1999 | Skladnev et al. | | 6,520,907 B1 | 2/2003 | Foley et al. |
| 5,961,522 A | 10/1999 | Mehdizadeh | | 6,527,786 B1 | 3/2003 | Davis et al. |
| 5,972,013 A | 10/1999 | Schmidt | | 6,533,749 B1 | 3/2003 | Mitusina et al. |
| 5,976,110 A | 11/1999 | Greengrass et al. | | 6,535,759 B1 | 3/2003 | Epstein et al. |
| 5,976,146 A | 11/1999 | Ogawa et al. | | 6,540,742 B1 | 4/2003 | Thomas et al. |
| 6,002,964 A | 12/1999 | Feler et al. | | 6,540,761 B2 | 4/2003 | Houser |
| 6,004,326 A | 12/1999 | Castro et al. | | 6,546,270 B1 | 4/2003 | Goldin et al. |
| 6,010,493 A | 1/2000 | Snoke | | 6,558,353 B2 | 5/2003 | Zohmann |
| 6,015,406 A | 1/2000 | Goble et al. | | 6,562,033 B2 | 5/2003 | Shah et al. |
| 6,022,362 A | 2/2000 | Lee et al. | | 6,564,078 B1 | 5/2003 | Marino et al. |
| 6,030,383 A | 2/2000 | Benderev | | 6,564,079 B1 | 5/2003 | Cory et al. |
| 6,030,401 A | 2/2000 | Marino | | 6,564,088 B1 | 5/2003 | Soller et al. |
| 6,038,480 A * | 3/2000 | Hrdlicka et al. ............... 607/116 | | 6,569,160 B1 | 5/2003 | Goldin et al. |
| 6,048,345 A | 4/2000 | Berke et al. | | 6,575,979 B1 | 6/2003 | Cragg |
| 6,068,642 A | 5/2000 | Johnson et al. | | 6,579,291 B1 | 6/2003 | Keith et al. |
| 6,073,051 A | 6/2000 | Sharkey et al. | | 6,584,345 B2 * | 6/2003 | Govari .......................... 600/509 |
| 6,099,514 A | 8/2000 | Sharkey et al. | | 6,592,559 B1 | 7/2003 | Pakter et al. |
| 6,102,930 A | 8/2000 | Simmons, Jr. | | 6,595,932 B2 | 7/2003 | Ferrera |
| 6,106,558 A | 8/2000 | Picha | | 6,597,955 B2 | 7/2003 | Panescu et al. |
| 6,113,534 A | 9/2000 | Koros et al. | | 6,606,523 B1 | 8/2003 | Jenkins |
| D432,384 S | 10/2000 | Simons | | 6,609,018 B2 | 8/2003 | Cory et al. |
| 6,132,387 A | 10/2000 | Gozani et al. | | 6,610,066 B2 | 8/2003 | Dinger et al. |
| 6,136,014 A | 10/2000 | Sirimanne et al. | | 6,620,129 B2 | 9/2003 | Stecker et al. |
| 6,142,993 A | 11/2000 | Whayne et al. | | 6,622,731 B2 | 9/2003 | Daniel et al. |
| 6,142,994 A | 11/2000 | Swanson et al. | | 6,624,510 B1 | 9/2003 | Chan et al. |
| 6,146,380 A | 11/2000 | Racz et al. | | 6,626,916 B1 | 9/2003 | Yeung et al. |
| 6,152,894 A | 11/2000 | Kubler | | 6,632,184 B1 | 10/2003 | Truwit |
| 6,169,916 B1 | 1/2001 | West | | 6,638,233 B2 | 10/2003 | Corvi et al. |
| 6,205,360 B1 | 3/2001 | Carter et al. | | RE038,335 E | 11/2003 | Aust et al. |
| 6,214,001 B1 | 4/2001 | Casscells et al. | | 6,648,883 B2 | 11/2003 | Francischelli et al. |
| 6,214,016 B1 | 4/2001 | Williams et al. | | 6,666,874 B2 | 12/2003 | Heitzmann et al. |
| 6,236,892 B1 * | 5/2001 | Feler ............................ 607/117 | | 6,673,063 B2 | 1/2004 | Brett |
| 6,251,115 B1 | 6/2001 | Williams et al. | | 6,673,068 B1 | 1/2004 | Berube |
| 6,256,540 B1 | 7/2001 | Panescu et al. | | 6,678,552 B2 | 1/2004 | Pearlman |
| 6,259,945 B1 | 7/2001 | Epstein et al. | | 6,682,535 B2 | 1/2004 | Hoogland |
| 6,261,582 B1 | 7/2001 | Needham et al. | | 6,682,536 B2 | 1/2004 | Vardi et al. |
| 6,266,551 B1 | 7/2001 | Osadchy et al. | | 6,699,246 B2 | 3/2004 | Zucherman et al. |
| 6,266,558 B1 * | 7/2001 | Gozani et al. .................. 600/547 | | 6,723,049 B2 | 4/2004 | Skladnev et al. |
| 6,267,760 B1 | 7/2001 | Swanson | | 6,726,531 B1 | 4/2004 | Harrel |
| 6,272,367 B1 | 8/2001 | Chance | | 6,726,685 B2 | 4/2004 | To et al. |
| 6,277,094 B1 | 8/2001 | Schendel | | 6,733,496 B2 | 5/2004 | Sharkey et al. |
| 6,280,447 B1 | 8/2001 | Marino et al. | | 6,736,815 B2 | 5/2004 | Ginn |
| 6,292,702 B1 | 9/2001 | King et al. | | 6,736,835 B2 | 5/2004 | Pellegrino et al. |
| 6,298,256 B1 | 10/2001 | Meyer | | 6,746,451 B2 | 6/2004 | Middleton et al. |
| 6,312,392 B1 | 11/2001 | Herzon | | 6,752,814 B2 | 6/2004 | Gellman et al. |
| 6,324,418 B1 | 11/2001 | Crowley et al. | | 6,760,616 B2 | 7/2004 | Hoey et al. |

| Patent | Date | Inventor |
|---|---|---|
| 6,772,012 B2 | 8/2004 | Ricart et al. |
| 6,776,765 B2 | 8/2004 | Soukup et al. |
| 6,788,966 B2 | 9/2004 | Kenan et al. |
| 6,790,210 B1 | 9/2004 | Cragg et al. |
| 6,805,695 B2 | 10/2004 | Keith et al. |
| 6,805,697 B1 | 10/2004 | Helm et al. |
| 6,807,444 B2 | 10/2004 | Tu et al. |
| 6,830,561 B2 | 12/2004 | Jansen et al. |
| 6,830,570 B1 | 12/2004 | Frey et al. |
| 6,832,111 B2 | 12/2004 | Tu et al. |
| 6,845,264 B1 | 1/2005 | Skladnev et al. |
| 6,847,849 B2 | 1/2005 | Mamo et al. |
| 6,851,430 B2 | 2/2005 | Tsou |
| 6,865,409 B2 | 3/2005 | Getsla et al. |
| 6,872,204 B2 | 3/2005 | Houser |
| 6,875,221 B2 | 4/2005 | Cull |
| 6,882,879 B2 | 4/2005 | Rock |
| 6,884,220 B2 | 4/2005 | Aviv et al. |
| 6,890,353 B2 | 5/2005 | Cohn et al. |
| 6,899,716 B2 | 5/2005 | Cragg |
| 6,907,884 B2 | 6/2005 | Pellegrino et al. |
| 6,911,003 B2 | 6/2005 | Anderson et al. |
| 6,911,016 B2 | 6/2005 | Balzum et al. |
| 6,916,328 B2 | 7/2005 | Brett |
| 6,923,813 B2 | 8/2005 | Phillips et al. |
| 6,929,647 B2 | 8/2005 | Cohen |
| 6,949,104 B2 | 9/2005 | Griffis et al. |
| 6,962,587 B2 | 11/2005 | Johnson et al. |
| 6,971,986 B2 | 12/2005 | Staskin et al. |
| 6,972,199 B2 | 12/2005 | Lebouitz et al. |
| 6,973,342 B1 | 12/2005 | Swanson |
| 6,976,986 B2 | 12/2005 | Berube |
| 6,991,643 B2 | 1/2006 | Saadat |
| 6,994,693 B2 | 2/2006 | Tal |
| 6,997,934 B2 | 2/2006 | Snow et al. |
| 6,999,820 B2 | 2/2006 | Jordan |
| 7,001,333 B2 | 2/2006 | Hamel et al. |
| 7,008,431 B2 | 3/2006 | Simonson |
| 7,010,352 B2 | 3/2006 | Hogan |
| 7,011,635 B1 | 3/2006 | Delay |
| 7,011,663 B2 | 3/2006 | Michelson |
| 7,014,616 B2 | 3/2006 | Ferrera |
| 7,033,373 B2 | 4/2006 | de la Torre et al. |
| 7,041,099 B2 | 5/2006 | Thomas et al. |
| 7,047,084 B2 | 5/2006 | Erickson et al. |
| 7,048,682 B2 | 5/2006 | Neisz et al. |
| 7,050,848 B2 | 5/2006 | Hoey et al. |
| 7,063,682 B1 | 6/2006 | Whayne et al. |
| 7,070,556 B2 | 7/2006 | Anderson et al. |
| 7,070,596 B1 | 7/2006 | Woloszko et al. |
| 7,079,883 B2 | 7/2006 | Marino et al. |
| 7,081,122 B1 | 7/2006 | Reiley et al. |
| 7,087,053 B2 | 8/2006 | Vanney |
| 7,087,058 B2 | 8/2006 | Cragg |
| 7,107,104 B2 | 9/2006 | Keravel et al. |
| 7,118,576 B2 | 10/2006 | Gitis et al. |
| 7,141,019 B2 | 11/2006 | Pearlman |
| 7,166,073 B2 | 1/2007 | Ritland |
| 7,166,081 B2 | 1/2007 | McKinley |
| 7,166,107 B2 | 1/2007 | Anderson |
| 7,169,107 B2 | 1/2007 | Jersey-Willuhn et al. |
| 7,189,240 B1 | 3/2007 | Dekel |
| 7,198,598 B2 | 4/2007 | Smith et al. |
| 7,198,626 B2 | 4/2007 | Lee et al. |
| 7,207,949 B2 | 4/2007 | Miles et al. |
| 7,211,082 B2 | 5/2007 | Hall et al. |
| 7,214,186 B2 | 5/2007 | Ritland |
| 7,216,001 B2 | 5/2007 | Hacker et al. |
| 7,223,278 B2 | 5/2007 | Davison et al. |
| 7,239,911 B2 | 7/2007 | Scholz |
| 7,270,658 B2 | 9/2007 | Woloszko et al. |
| 7,282,061 B2 | 10/2007 | Sharkey et al. |
| 7,337,005 B2 | 2/2008 | Kim et al. |
| 7,337,006 B2 | 2/2008 | Kim et al. |
| 7,470,236 B1 | 12/2008 | Kelleher et al. |
| 7,494,473 B2 | 2/2009 | Eggers et al. |
| 7,503,920 B2 | 3/2009 | Siegal |
| 7,507,218 B2 | 3/2009 | Aliski et al. |
| 7,617,006 B2 | 11/2009 | Metzler et al. |
| 7,641,658 B2 | 1/2010 | Shaolian et al. |
| 7,648,521 B2 | 1/2010 | Hestad |
| 7,655,026 B2 | 2/2010 | Justis et al. |
| 7,666,186 B2 | 2/2010 | Harp |
| 7,666,209 B2 | 2/2010 | Zucherman et al. |
| 7,857,813 B2 | 12/2010 | Schmitz et al. |
| 2001/0014806 A1 | 8/2001 | Ellman et al. |
| 2001/0025192 A1* | 9/2001 | Gerber et al. ................ 607/117 |
| 2001/0039419 A1 | 11/2001 | Francischelli et al. |
| 2001/0049527 A1 | 12/2001 | Cragg |
| 2001/0053885 A1 | 12/2001 | Gielen et al. |
| 2002/0016555 A1 | 2/2002 | Ritchart et al. |
| 2002/0019637 A1 | 2/2002 | Frey et al. |
| 2002/0022788 A1 | 2/2002 | Corvi et al. |
| 2002/0022873 A1* | 2/2002 | Erickson et al. ............. 607/117 |
| 2002/0029060 A1 | 3/2002 | Hogendijk |
| 2002/0106681 A1 | 8/2002 | Wexler et al. |
| 2002/0138091 A1 | 9/2002 | Pflueger |
| 2002/0183647 A1 | 12/2002 | Gozani et al. |
| 2003/0023190 A1 | 1/2003 | Cox |
| 2003/0045808 A1 | 3/2003 | Kaula et al. |
| 2003/0105503 A1 | 6/2003 | Marino |
| 2003/0109871 A1 | 6/2003 | Johnson et al. |
| 2003/0113906 A1 | 6/2003 | Sangha et al. |
| 2003/0130655 A1 | 7/2003 | Woloszko |
| 2003/0130738 A1 | 7/2003 | Hovda et al. |
| 2003/0167021 A1 | 9/2003 | Shimm |
| 2003/0187368 A1 | 10/2003 | Sata et al. |
| 2003/0188749 A1 | 10/2003 | Nichols et al. |
| 2003/0208206 A1 | 11/2003 | Gitis et al. |
| 2003/0212400 A1 | 11/2003 | Bloemer et al. |
| 2003/0225412 A1 | 12/2003 | Shiraishi |
| 2003/0225415 A1 | 12/2003 | Richard |
| 2004/0006379 A1 | 1/2004 | Brett |
| 2004/0006391 A1 | 1/2004 | Reiley |
| 2004/0019359 A1 | 1/2004 | Worley et al. |
| 2004/0024399 A1 | 2/2004 | Sharps et al. |
| 2004/0030330 A1 | 2/2004 | Brassell et al. |
| 2004/0049179 A1 | 3/2004 | Francischelli et al. |
| 2004/0049208 A1 | 3/2004 | Hill et al. |
| 2004/0054368 A1 | 3/2004 | Truckai et al. |
| 2004/0059247 A1 | 3/2004 | Urmey |
| 2004/0064058 A1 | 4/2004 | McKay |
| 2004/0067000 A1 | 4/2004 | Bates et al. |
| 2004/0097927 A1 | 5/2004 | Yeung et al. |
| 2004/0102721 A1 | 5/2004 | McKinley |
| 2004/0106940 A1 | 6/2004 | Shaolian et al. |
| 2004/0111084 A1 | 6/2004 | Brett |
| 2004/0116977 A1 | 6/2004 | Finch et al. |
| 2004/0122433 A1 | 6/2004 | Loubens et al. |
| 2004/0122459 A1 | 6/2004 | Harp |
| 2004/0122482 A1 | 6/2004 | Tung et al. |
| 2004/0127893 A1 | 7/2004 | Hovda |
| 2004/0127963 A1 | 7/2004 | Uchida et al. |
| 2004/0133208 A1 | 7/2004 | Weikel et al. |
| 2004/0143165 A1 | 7/2004 | Alleyne |
| 2004/0143280 A1 | 7/2004 | Suddaby |
| 2004/0162609 A1 | 8/2004 | Hossainy et al. |
| 2004/0167444 A1 | 8/2004 | Laroya et al. |
| 2004/0167553 A1 | 8/2004 | Simpson et al. |
| 2004/0181150 A1 | 9/2004 | Evans et al. |
| 2004/0199084 A1 | 10/2004 | Kelleher et al. |
| 2004/0199159 A1 | 10/2004 | Lee et al. |
| 2004/0199166 A1 | 10/2004 | Schmieding et al. |
| 2004/0260358 A1 | 12/2004 | Vaughan et al. |
| 2005/0027199 A1 | 2/2005 | Clarke |
| 2005/0033393 A1 | 2/2005 | Daglow |
| 2005/0049592 A1 | 3/2005 | Keith et al. |
| 2005/0060006 A1 | 3/2005 | Pflueger et al. |
| 2005/0075578 A1 | 4/2005 | Gharib et al. |
| 2005/0149034 A1 | 7/2005 | Assell et al. |
| 2005/0149035 A1 | 7/2005 | Pimenta et al. |
| 2005/0149154 A1 | 7/2005 | Cohen et al. |
| 2005/0171587 A1 | 8/2005 | Daglow et al. |
| 2005/0182454 A1 | 8/2005 | Gharib et al. |
| 2005/0187537 A1 | 8/2005 | Loeb et al. |
| 2005/0197661 A1 | 9/2005 | Carrison et al. |
| 2005/0203599 A1 | 9/2005 | Garabedian et al. |
| 2005/0209610 A1 | 9/2005 | Carrison |

| | | |
|---|---|---|
| 2005/0209617 A1 | 9/2005 | Koven et al. |
| 2005/0209622 A1 | 9/2005 | Carrison |
| 2005/0216023 A1 | 9/2005 | Aram et al. |
| 2005/0222598 A1 | 10/2005 | Ho et al. |
| 2005/0234425 A1 | 10/2005 | Miller et al. |
| 2005/0256423 A1 | 11/2005 | Kirsner |
| 2005/0261692 A1 | 11/2005 | Carrison et al. |
| 2005/0277942 A1 | 12/2005 | Kullas et al. |
| 2005/0283148 A1 | 12/2005 | Janssen et al. |
| 2006/0004369 A1 | 1/2006 | Patel et al. |
| 2006/0015035 A1 | 1/2006 | Rock |
| 2006/0025702 A1 | 2/2006 | Sterrantino et al. |
| 2006/0025703 A1 | 2/2006 | Miles et al. |
| 2006/0025797 A1 | 2/2006 | Lock et al. |
| 2006/0030854 A1 | 2/2006 | Haines |
| 2006/0036211 A1 | 2/2006 | Solsberg et al. |
| 2006/0036271 A1 | 2/2006 | Schomer et al. |
| 2006/0036272 A1 | 2/2006 | Solsberg et al. |
| 2006/0058732 A1 | 3/2006 | Harp |
| 2006/0064101 A1 | 3/2006 | Arramon |
| 2006/0079919 A1 | 4/2006 | Harp |
| 2006/0085048 A1 | 4/2006 | Cory et al. |
| 2006/0085049 A1 | 4/2006 | Cory et al. |
| 2006/0089609 A1 | 4/2006 | Bleich et al. |
| 2006/0089633 A1* | 4/2006 | Bleich et al. .................. 606/32 |
| 2006/0089640 A1 | 4/2006 | Bleich et al. |
| 2006/0089650 A1 | 4/2006 | Nolde |
| 2006/0089688 A1 | 4/2006 | Panescu |
| 2006/0094976 A1 | 5/2006 | Bleich |
| 2006/0095026 A1 | 5/2006 | Ricart et al. |
| 2006/0095028 A1 | 5/2006 | Bleich |
| 2006/0095059 A1 | 5/2006 | Bleich et al. |
| 2006/0100651 A1 | 5/2006 | Bleich |
| 2006/0122458 A1 | 6/2006 | Bleich |
| 2006/0122620 A1 | 6/2006 | Kim |
| 2006/0122653 A1 | 6/2006 | Bradley et al. |
| 2006/0122654 A1 | 6/2006 | Bradley et al. |
| 2006/0135882 A1 | 6/2006 | Bleich |
| 2006/0142753 A1 | 6/2006 | Francischelli et al. |
| 2006/0149278 A1 | 7/2006 | Abdou |
| 2006/0161189 A1 | 7/2006 | Harp |
| 2006/0173374 A1 | 8/2006 | Neubardt et al. |
| 2006/0184175 A1 | 8/2006 | Schomer et al. |
| 2006/0195107 A1 | 8/2006 | Jones et al. |
| 2006/0200153 A1 | 9/2006 | Harp |
| 2006/0200154 A1 | 9/2006 | Harp |
| 2006/0200155 A1 | 9/2006 | Harp |
| 2006/0206115 A1 | 9/2006 | Schomer et al. |
| 2006/0206117 A1 | 9/2006 | Harp |
| 2006/0206118 A1 | 9/2006 | Kim et al. |
| 2006/0206178 A1 | 9/2006 | Kim |
| 2006/0224060 A1 | 10/2006 | Garell et al. |
| 2006/0224078 A1 | 10/2006 | Hoey et al. |
| 2006/0235451 A1 | 10/2006 | Schomer et al. |
| 2006/0235452 A1 | 10/2006 | Schomer et al. |
| 2006/0241648 A1 | 10/2006 | Bleich et al. |
| 2006/0258951 A1 | 11/2006 | Bleich et al. |
| 2006/0264952 A1 | 11/2006 | Nelson et al. |
| 2006/0264994 A1 | 11/2006 | Schomer et al. |
| 2006/0276720 A1 | 12/2006 | McGinnis et al. |
| 2006/0276802 A1 | 12/2006 | Vresilovic et al. |
| 2006/0276836 A1 | 12/2006 | Bergin et al. |
| 2007/0010717 A1 | 1/2007 | Cragg |
| 2007/0016097 A1 | 1/2007 | Farquhar et al. |
| 2007/0016185 A1 | 1/2007 | Tullis et al. |
| 2007/0027464 A1 | 2/2007 | Way et al. |
| 2007/0027514 A1* | 2/2007 | Gerber .......................... 607/116 |
| 2007/0049962 A1 | 3/2007 | Marino et al. |
| 2007/0055215 A1 | 3/2007 | Tran et al. |
| 2007/0055262 A1 | 3/2007 | Tomita et al. |
| 2007/0055263 A1 | 3/2007 | Way et al. |
| 2007/0073356 A1* | 3/2007 | Rooney et al. .................. 607/46 |
| 2007/0106219 A1 | 5/2007 | Grabinsky |
| 2007/0123766 A1 | 5/2007 | Whalen, III et al. |
| 2007/0123888 A1 | 5/2007 | Bleich et al. |
| 2007/0123890 A1 | 5/2007 | Way et al. |
| 2007/0162044 A1 | 7/2007 | Marino |
| 2007/0162061 A1 | 7/2007 | Way et al. |
| 2007/0162062 A1 | 7/2007 | Norton et al. |
| 2007/0166345 A1 | 7/2007 | Pavcnik et al. |
| 2007/0198019 A1 | 8/2007 | Schomer et al. |
| 2007/0213583 A1 | 9/2007 | Kim et al. |
| 2007/0213584 A1 | 9/2007 | Kim et al. |
| 2007/0213733 A1 | 9/2007 | Bleich et al. |
| 2007/0213734 A1 | 9/2007 | Bleich et al. |
| 2007/0213735 A1 | 9/2007 | Saadat et al. |
| 2007/0225703 A1 | 9/2007 | Schmitz et al. |
| 2007/0255162 A1 | 11/2007 | Abboud et al. |
| 2007/0255369 A1 | 11/2007 | Bonde et al. |
| 2007/0260252 A1 | 11/2007 | Schmitz et al. |
| 2007/0270795 A1 | 11/2007 | Francischelli et al. |
| 2007/0270865 A1 | 11/2007 | Arnin et al. |
| 2007/0276286 A1 | 11/2007 | Miller |
| 2007/0276390 A1 | 11/2007 | Solsberg et al. |
| 2007/0282217 A1 | 12/2007 | McGinnis et al. |
| 2007/0299403 A1 | 12/2007 | Crowe et al. |
| 2007/0299459 A1 | 12/2007 | Way et al. |
| 2008/0033465 A1 | 2/2008 | Schmitz et al. |
| 2008/0051812 A1 | 2/2008 | Schmitz et al. |
| 2008/0058874 A1 | 3/2008 | Westlund et al. |
| 2008/0097465 A1 | 4/2008 | Rollins et al. |
| 2008/0119711 A1 | 5/2008 | Nikumb et al. |
| 2008/0125621 A1 | 5/2008 | Gellman et al. |
| 2008/0125709 A1 | 5/2008 | Chang et al. |
| 2008/0140153 A1 | 6/2008 | Burdulis |
| 2008/0140169 A1 | 6/2008 | Imran |
| 2008/0146867 A1 | 6/2008 | Gellman et al. |
| 2008/0161810 A1 | 7/2008 | Melkent |
| 2008/0197024 A1 | 8/2008 | Simpson et al. |
| 2008/0200912 A1 | 8/2008 | Long et al. |
| 2008/0221383 A1 | 9/2008 | Way et al. |
| 2008/0221586 A1 | 9/2008 | Garcia-Bengochea et al. |
| 2008/0255439 A1 | 10/2008 | Tang et al. |
| 2008/0288005 A1 | 11/2008 | Jackson |
| 2008/0319459 A1 | 12/2008 | Al-najjar |
| 2009/0018610 A1 | 1/2009 | Gharib et al. |
| 2009/0054804 A1 | 2/2009 | Gharib et al. |
| 2009/0054936 A1 | 2/2009 | Eggen et al. |
| 2009/0054941 A1 | 2/2009 | Eggen et al. |
| 2009/0062871 A1 | 3/2009 | Chin et al. |
| 2009/0062872 A1 | 3/2009 | Chin et al. |
| 2009/0105604 A1 | 4/2009 | Bertagnoli et al. |
| 2009/0105788 A1 | 4/2009 | Bartol et al. |
| 2009/0138056 A1 | 5/2009 | Anderson et al. |
| 2009/0143829 A1 | 6/2009 | Shluzas |
| 2009/0177112 A1 | 7/2009 | Gharib et al. |
| 2009/0182382 A1 | 7/2009 | Justis et al. |
| 2009/0209879 A1 | 8/2009 | Kaula et al. |
| 2009/0216284 A1 | 8/2009 | Chin et al. |
| 2009/0299166 A1 | 12/2009 | Nishida |
| 2010/0057087 A1 | 3/2010 | Cha |
| 2010/0274250 A1 | 10/2010 | Wallace et al. |
| 2010/0331883 A1 | 12/2010 | Schmitz et al. |
| 2010/0331900 A1 | 12/2010 | Garabedian et al. |
| 2011/0004207 A1 | 1/2011 | Wallace et al. |

FOREIGN PATENT DOCUMENTS

| | | |
|---|---|---|
| DE | 4036804 A1 | 5/1992 |
| EP | 359883 A1 | 3/1990 |
| EP | 1304080 A2 | 4/2003 |
| EP | 1340467 A2 | 9/2003 |
| EP | 1207794 B1 | 5/2004 |
| EP | 1315463 B1 | 5/2005 |
| EP | 1611851 A1 | 1/2006 |
| EP | 1006885 B1 | 9/2006 |
| FR | 2706309 | 12/1994 |
| JP | 2960140 B2 | 10/1999 |
| JP | 24065380 A2 | 3/2004 |
| RU | 2107459 | 3/1998 |
| WO | WO-96/22057 | 7/1996 |
| WO | WO9734536 A2 | 9/1997 |
| WO | WO9918866 A1 | 4/1999 |
| WO | WO99/21500 A1 | 5/1999 |
| WO | WO00/67651 A1 | 11/2000 |
| WO | WO0108571 A1 | 2/2001 |
| WO | WO01/62168 A2 | 8/2001 |
| WO | WO0207901 A1 | 1/2002 |
| WO | WO0234120 A2 | 5/2002 |

| | | |
|---|---|---|
| WO | WO02076311 A2 | 10/2002 |
| WO | WO 03/026482 A2 | 4/2003 |
| WO | WO03/066147 A1 | 8/2003 |
| WO | WO2004002331 A1 | 1/2004 |
| WO | WO2004028351 A2 | 4/2004 |
| WO | WO2004/043272 A1 | 5/2004 |
| WO | WO2004056267 A1 | 7/2004 |
| WO | WO2004/078066 A2 | 9/2004 |
| WO | WO2004080316 A1 | 9/2004 |
| WO | WO2004096080 A2 | 11/2004 |
| WO | WO2005/009300 A1 | 2/2005 |
| WO | WO2005057467 A2 | 6/2005 |
| WO | WO2005077282 A1 | 8/2005 |
| WO | WO2005089433 A2 | 9/2005 |
| WO | WO2006009705 A2 | 1/2006 |
| WO | WO2006015302 A1 | 2/2006 |
| WO | WO2006017507 A2 | 2/2006 |
| WO | WO2006039279 A2 | 4/2006 |
| WO | WO2006042206 A2 | 4/2006 |
| WO | WO2006044727 A2 | 4/2006 |
| WO | WO2006047598 A1 | 5/2006 |
| WO | WO2006058079 A3 | 6/2006 |
| WO | WO2006058195 A2 | 6/2006 |
| WO | WO2006062555 A2 | 6/2006 |
| WO | WO2006086241 A2 | 8/2006 |
| WO | WO2006099285 A2 | 9/2006 |
| WO | WO2006102085 A2 | 9/2006 |
| WO | WO2007008709 A2 | 1/2007 |
| WO | WO2007021588 A1 | 2/2007 |
| WO | WO2007022194 A2 | 2/2007 |
| WO | WO2007059343 A2 | 2/2007 |
| WO | WO2007067632 A2 | 6/2007 |
| WO | WO2008008898 A2 | 1/2008 |
| WO | WO 2009/012265 A2 | 1/2009 |
| WO | WO 2009/018220 A1 | 2/2009 |
| WO | WO 2009/021116 A2 | 2/2009 |
| WO | WO-2010/014538 | 4/2010 |

OTHER PUBLICATIONS

Bleich, et al.; U.S. Appl. No. 12/127,535 entitled "Guidewire exchange systems to treat spinal stenosis," filed May 27, 2008.

Bleich, et al.; U.S. Appl. No. 12/140,201 entitled "Devices and methods for measuring the space around a nerve root," filed Jun. 16, 2008.

Schmitz et al.; U.S. Appl. No. 12/170,392 entitled "Spinal access system and method," filed Jul. 9, 2008.

Barer Malvin, "Instrument to Enhance Passage of the Gigli Saw," Journal of Pediatric Orthopedics, Raven Press, New York, 1984, 4:762-763.

Baumgart et al., "Indikation and Technik der Knochendurchtrennung," Der Chirurg, 1998, vol. 69:1188-1196. (in German with Eng Summary).

Bohinski et al., "Novel use of a threadwire saw for high sacral amputation," Journal of neurosurgery: Spine, 2005, vol. 3, 71R78.

Brunori et al., "Celebrating the centennial (1894-1994): Leonardo Gigli and his wire saw," J. Neurosurg, 1995, 82:1086-1090.

Burrows, Harold, "Surgical instruments and appliances used in operations," Faber and Faber, London, 1937, total pp. 4.

Codman Laminectomy Shaver (a Johnson & Johnson company www.codman.com) catalogue, pp. 416-431, [online] Retrieved from the internet: <URL: http:IIwww.codman.com/PDFs/Catalog_04_R.pdf>.

Dammann, Gordon, Pictorial Encyclopedia of Civil War Medical Instruments and Equipment, Pictorial Histories Publishing Company, Missoula, Montana, 1983, Total pp. 2.

Edwards et al; "T-Saw Laminoplasty for the Management of Cervical Spondylotic Myelopathy," Spine, Lippincott Williams & Wilkins, Inc., 2000, vol. 25 (14): 1788R1794.

Ellman Int. Disc-FX System Accessories K052241 [online] Retrieved from the Internet: <URL: http://www.ellman.com/ medical/ >.

Eralp et al., "A comparison of two osteotomy techniques for tibial lengthening," Archives of orthopaedic and trauma surgery, 2004, vol. 124:298R300.

Fessler Richard G, "Minimally Invasive Microendoscopic Decompressive Laminotomy for Lumbar Stenosis," American Association of Neurological Surgeons, 2006, Online CME course, [Retrieved on Jun. 29, 2006 from the Internet <http://www.aans.emedtrain.com/lumbar_stenosis/lumbarStenosis.swf>.

Fujita et al., "Chordoma in the Cervical Spine Managed with En Bloc Excision," Spine, Lippincott Williams & Wilkins, Inc., 1999, 24 (17), 1848-1851.

Goel, Atul, "Neurosurgical forum, Supraorbital Craniotomy," Journal of Neurosurgery, 1994, vol. 81, 642-643.

Gore Smoother User Manual, W. L. Gore & Associates, Inc. Flagstaff, AZ, Dec. 1999,Total pp. 3.

Hara et al., "En Bloc Laminoplasty Performed with Threadwire Saw: Technical Note," Neurosurgery, Jan 2001, Vol. 48, No. 1, pp. 235-239.

Hata et al; "A less invasive surgery for rotator cuff tear: Mini-open repair," Journal of Shoulder and Elbow Surgery, 2001, vol. 10 No. 1, 11-16.

Honl et al; "The Use of Water-Jetting Technology in Prostheses Revision Surgery R First Results of Parameter Studies on Bone and Bone Cement," J. Biomed Mater Res (Applied Biomaterials), John Wiley & Sons, Inc, 2000, 53, 6: 781-790.

Integra Ruggles TM Kerrison Rongeurs [online] Retrieved from the internet: <URL: http://www.integra-ls.com/products!? product=22>.

Jun, Byung-Yoon, "Posterior Lumbar Interbody Fusion With Restoration of Lamina and Facet Fusion," Spine, Lippincott Williams & Wilkins, Inc., 2000, vol. 25 No. 8, 917R922.

Kawahara et al., "Recapping T-Saw Laminoplasty for Spinal Cord Tumors," Spine, 1999, vol. 24 No. 13, pp. 1363-1370.

Martin-Benlloch et al., "Expansive Laminoplasty as a Method for Managing Cervical Multilevel Spondylotic Myelopathy," Spine, Lippincott Williams & Wilkins, Inc., 2003, vol. 28 No. 7, 680R684.

Miyamoto et al., "Kyphectomy Using a Surgical Threadwire (T-saw) for Kyphotic Deformity in a Child With Myelomeningocele," SPINE, Lippincott Williams & Wilkins, Inc., 2003, vol. 28 No. 10, E187RE190.

Abdel-Wanis et al., "Tumor growth potential after tumoral and instrumental contamination: an in-vivo comparative study of T-saw, Gigli saw, and scalpel," Journal of orthopaedic science, 2001, vol. 6, 424R429.

Mopec Bone-Cutting tool, Product brochure, Total pp. 4.

Nakagiri et al., "Thoracoscopic Rib Resection Using a Gigli Saw," The Annals of Thoracic Surgery, 2005, vol. 80, 755R756.

Osaka et al., "Clinical significance of a wide excision policy for sacrococcygeal chordoma," J Cancer Res Clin Oncol, 2005, Total pp. 6.

Paley et al., "Percutaneous Osteotomies," Orthopedic Clinics of North America, 1991, vol. 22 No. 4, 613-624.

Pancoast, Joseph, "A Treatise on Operative Surgery," Carey and Hart, Philadelphia,1844, Total pp. 11.

Park et al; "Cases of the Excision of Carious Joints," John Scrymgeour, Glasgow, 1806, Total pp. 6.

Peavy et al., "Comparison of Cortical Bone Ablations by Using Infrared Laser Wavelengths 2.9 to 9.2 μm, Lasers in Surgery and Medicine," 1999, vol. 26, 421R434.

Peltier, Leonard Orthopedics: A History and Iconography, Norman Publishing, San Francisco, 1993, Total pp. 3.

Reckling Frederick, "Modified Stethoscope Earpiece Makes Excellent Gigli Saw Guide," J Bone and Joint Surgery Am, Dec. 1972, 54-A(8), 1787-1788.

Rutkow, Ira, "Surgery An Illustrated History," Mosby'Year Book, Inc., St. Louis, 1993, Total pp. 4.

Schwieger et al., "Abrasive Water Jet Cutting as a New Procedure for Cutting Cancellous Bone In Vitro Testing in Comparison with the Oscillating Saw," Wiley Interscience, www.interscience,wiley.com, Sep. 20, 2004, 223-228.

Sen, Cengiz, Tibia proksimalinde Gigli testeresi ile yapilanperkütan osteotominin güvenilirligi: Kadavra calismasi, Acta orthopaedica et traumatologica turcica, 2002, vol. 36, 136-140; (in Russian w/ Eng Summary).

Shiraishi et al., "Results of Skip Laminectomy—Minimum 2-Year Follow-up Study Compared With Open-Door Laminoplasty," Spine, Lippincott Williams & Wilkins, Inc., 2003, vol. 28 No. 24, 2667-2672.

Shiraishi T., "A new technique for exposure of the cervical spine laminae," Journal of neurosurgery. Spine, 2002, vol. 96(1), 122-126.
Shiraishi T., Skip laminectomy—a new treatment for cervical spondylotic myelopathy, preserving bilateral muscular attachments to the spinous processes: a preliminary report, Spine, 2002, vol. 2(2), 108-115.
Skippen et al., "The Chain Saw R A Scottish Invention," Scottish Medical Journal, 2004, vol. 49(2), 72-75.
Stevens et al., "Calvarial Bone Graft Harvest Using the Gigli Saw," Journal of Oral and Maxillofacial Surgery, 1998, vol. 56, 798-799.
Takada et al., "Unusual Metastasis to the Cauda Equina From Renal Cell Carcinoma," Spine, Lippincott Williams & Wilkins, Inc., 2003, vol. 28 No. 6, E114RE117.
Paktiss et al., "Afghan Percutaneous Osteotomy," Journal of Pediatric Orthopaedics, Raven Press Ltd, New York, 1993, vol. 13 No. 4, 531-533.
Tomita et al., "Expansive Midline T-Saw Laminoplasty (Modified Spinour Process-Splitting) for the Management of Cervical Myelopathy," Spine, Lippincott Williams & Wilkins, Inc, 1998, 23(1), 32-37.
Tomita et al., "The Threadwire Saw: a New Device for Cutting Bone," The Journal of Bone and Joint Surgery, 1996, vol. 78, 1915-1917.
Tomita et al., "Total en bloc spondylectomy and circumspinal decompression for solitary spinal metastasis," Paraplegia, 1994, 32:36-46.
Tomita K. et al., "Total en bloc spondylectomy for solitary spinal metastases," International Orthopaedics (SICOT), 1994, 18: 291-298.
Truax, Charles, "The Mechanics of Surgery," Chicago, IL; 1899, Total pp. 3.
US Surgical Kerrison Spinal Rongeur K943116 [online] Retrieved from the internet: <URL: http://www.ussurg.com/uss/index.html>.
Wilkins, Robert H, "Neurosurgical Classics," Johnson Reprint Corporation, New York, 1965, 377-382.
Zeppelin Laminectomy Rongeur K901372, [online] Retrieved from the internet: <URL: http://www.zeppelin-medical.com/download/instruments.pdf>.
Bleich et al; U.S. Appl. No. 11/952,934 entitled "Tissue Removal Devices and Methods," filed Dec. 7, 2007.
Schmitz et al; U.S. Appl. No. 11/468,247 entitled "Tissue access guidewire system and method," filed Aug. 29, 2006.
Schmitz et al; U.S. Appl. No. 11/468,252 entitled "Tissue access guidewire system and method," filed Aug. 29, 2006.
Schmitz et al; U.S. Appl. No. 11/538,345 entitled "Articulating Tissue Cutting Device," filed Oct. 3, 2006.
Schmitz et al; U.S. Appl. No. 11/843,561 entitled "Surgical Probe and Method of Making," filed Aug. 22, 2007.
Schmitz et al; U.S. Appl. No. 11/870,370 entitled "Percutaneous Spinal Stenosis Treatment," filed Oct. 10, 2007.
Bleich et al.; U.S. Appl. No. 12/504,545 entitled "Spinal access and neural localization," filed Jul. 16, 2009.
Schmitz et al.; U.S. Appl. No. 12/496,094 entitled "Access and tissue modification systems and methods," filed Jul. 1, 2009.
Schmitz et al.; U.S. Appl. No. 12/324,147 entitled "Tissue modification devices," filed Nov. 26, 2008.
Schmitz et al.; U.S. Appl. No. 12/352,385 entitled "Devices, methods and systems for neural localization," filed Jan. 12, 2009.
Bleich et al.; U.S. Appl. No. 12/352,978 entitled "Multiple pathways for spinal nerve rood decompression from a single access point," filed Jan. 13, 2009.
Bleich, Jeffrey; U.S. Appl. No. 12/357,289 entitled "Devices and methods for selective surgical removal of tissue," filed Jan. 21, 2009.
Bleich et al.; U.S. Appl. No. 12/428,369 entitled "Devices and methods for tissue modification," filed Apr. 22, 2009.
Bleich et al.; U.S. Appl. No. 12/637,447 entitled "Devices and methods for tissue modification," filed Dec. 14, 2009.
Garabedian et al.; U.S. Appl. No. 12/824,043; entitled "Surgical Tools for Treatment of Spinal Stenosis"; filed Jun. 25, 2010.
Schmitz et al.; U.S. Appl. No. 12/816,729 entitled Access and Tissue Modification Systems and Methods, filed Jun. 16, 2010.
Wallace et al.; U.S. Appl. No. 12/724,315 entitled "Flexible Neural Localization Devices and Methods," filed Mar. 15, 2010.
Wallace et al.; U.S. Appl. No. 12/773,595 entitled "Tissue Modification Devices and Methods," filed May 4, 2010.
Arcenio et al.; U.S. Appl. No. 12/980,165 entitled "Systems and Methods for Performing Spinal Fusion", filed Dec. 28, 2010.
Bleich et al.; U.S. Appl. No. 12/984,162 entitled "Devices and Methods for Tissue Access", filed Jan. 4, 2011.
Schmitz et al.; U.S. Appl. No. 12/917,253; entitled "Tissue Access Guidewire System and Method"; filed Nov. 1, 2010.
Wallace et al.; U.S. Appl. No. 12/911,537 entitled "Devices and Methods for Treating Tissue", filed Oct. 25, 2010.
Wallace et al.; U.S. Appl. No. 13/007,381 entitled "Tissue Modification Devices", filed Jan. 14, 2011.

* cited by examiner

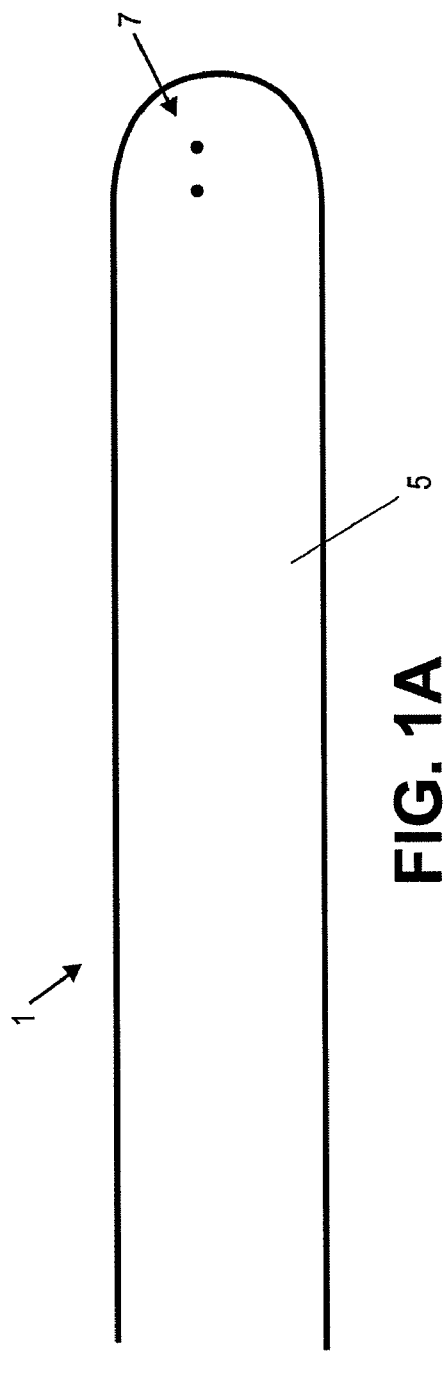
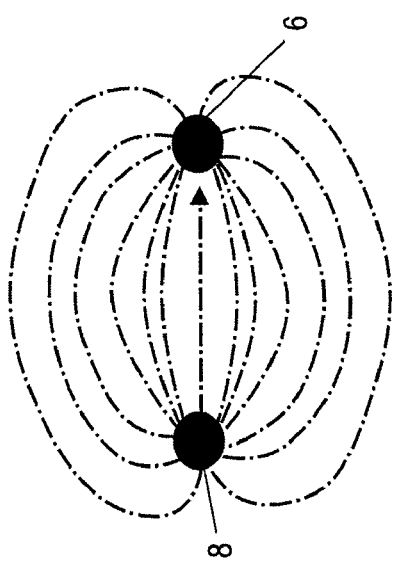
FIG. 1A
FIG. 1C
FIG. 1B

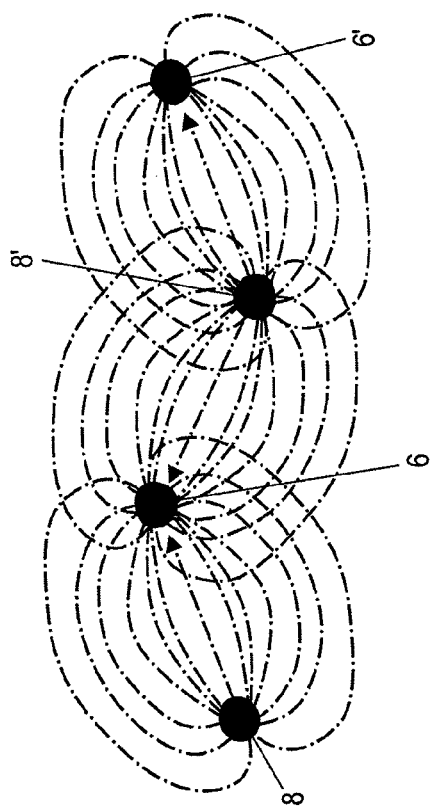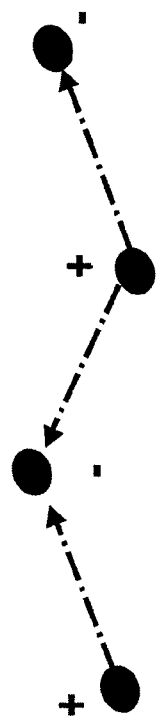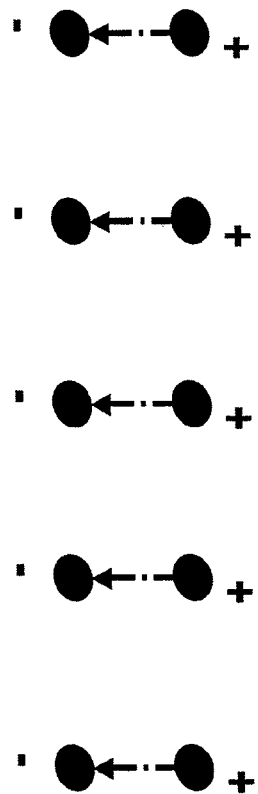

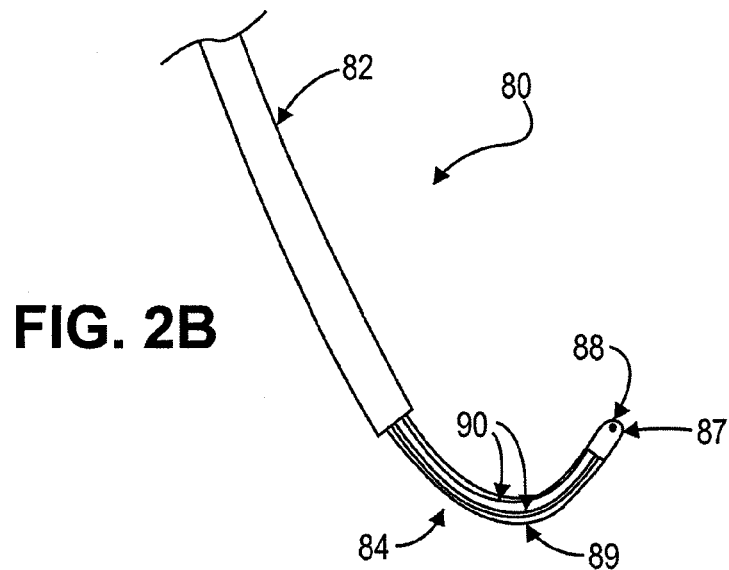
FIG. 2B
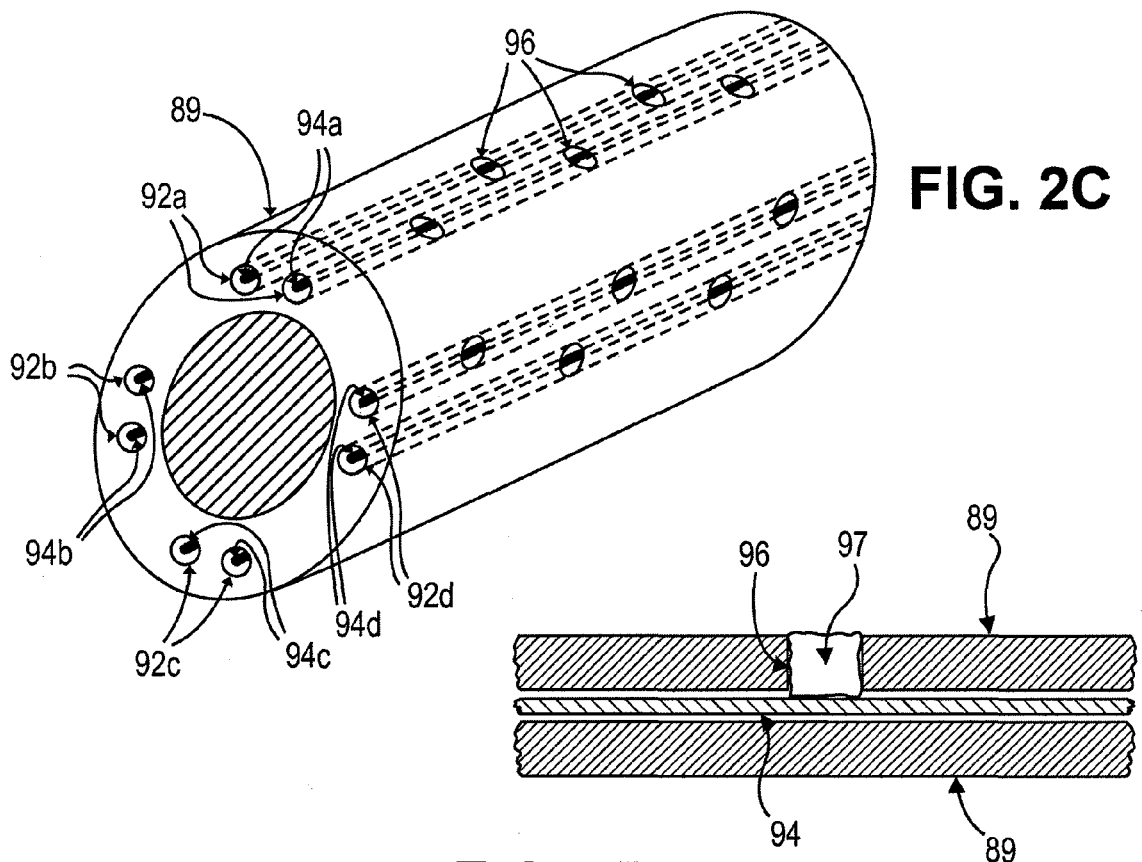
FIG. 2C
FIG. 2D

FIG. 5A  FIG. 6A  FIG. 7A
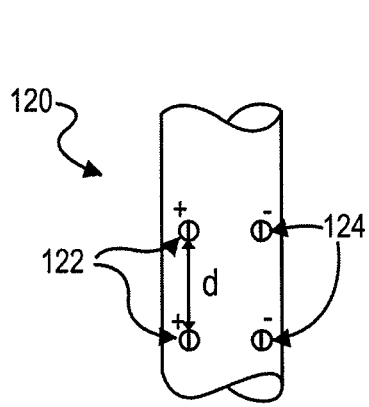 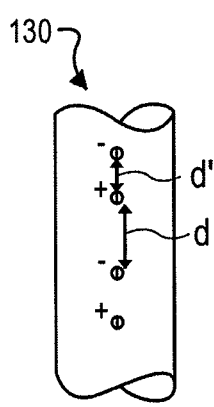 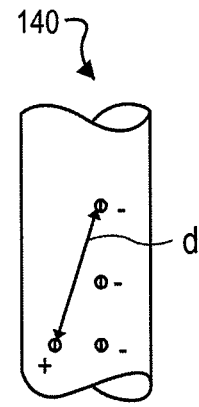
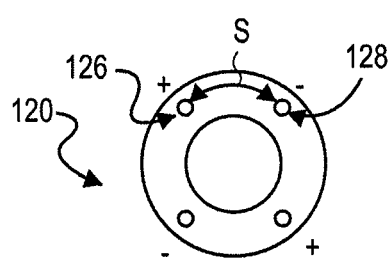 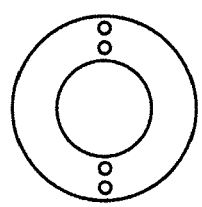 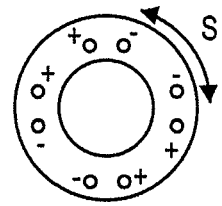
FIG. 5B  FIG. 6B  FIG. 7B
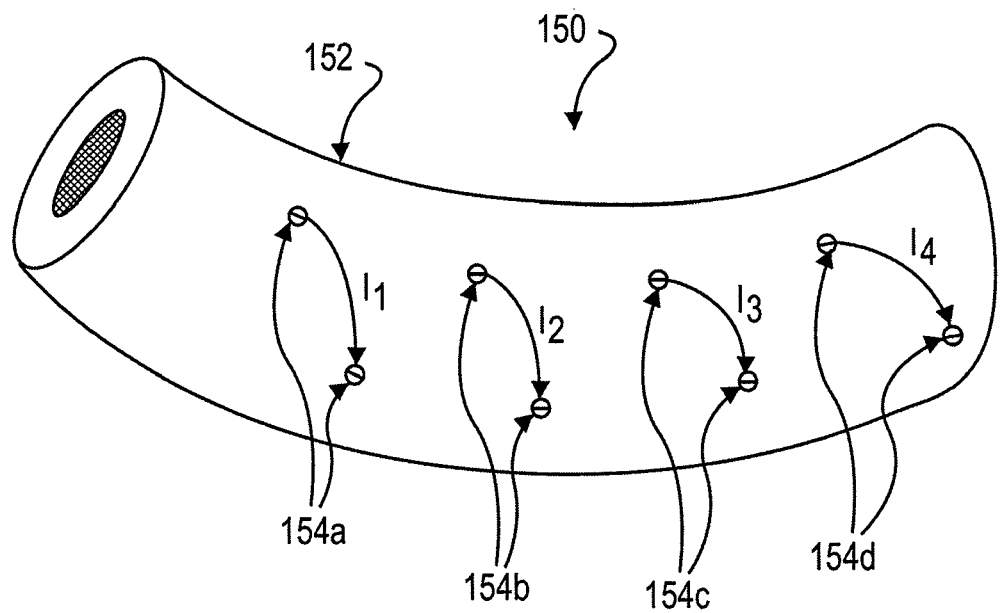
FIG. 8

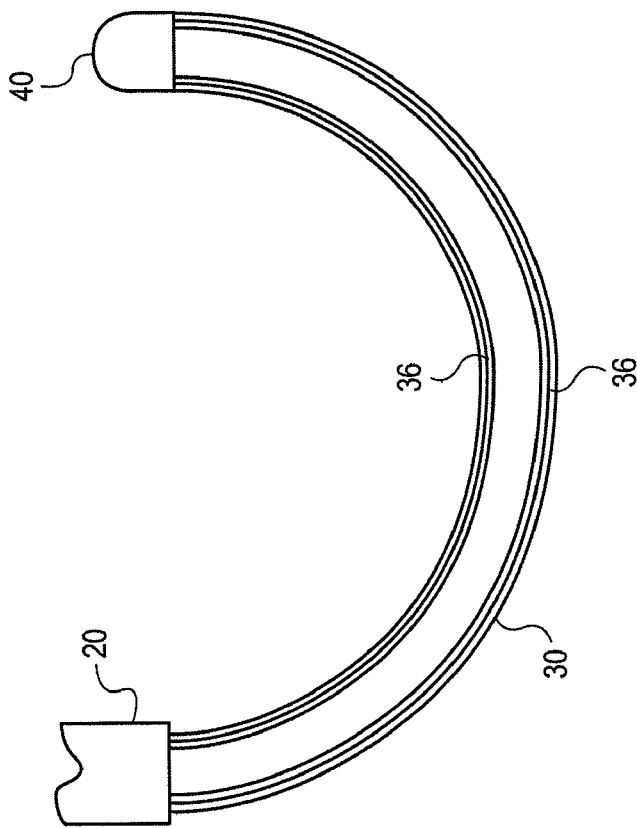
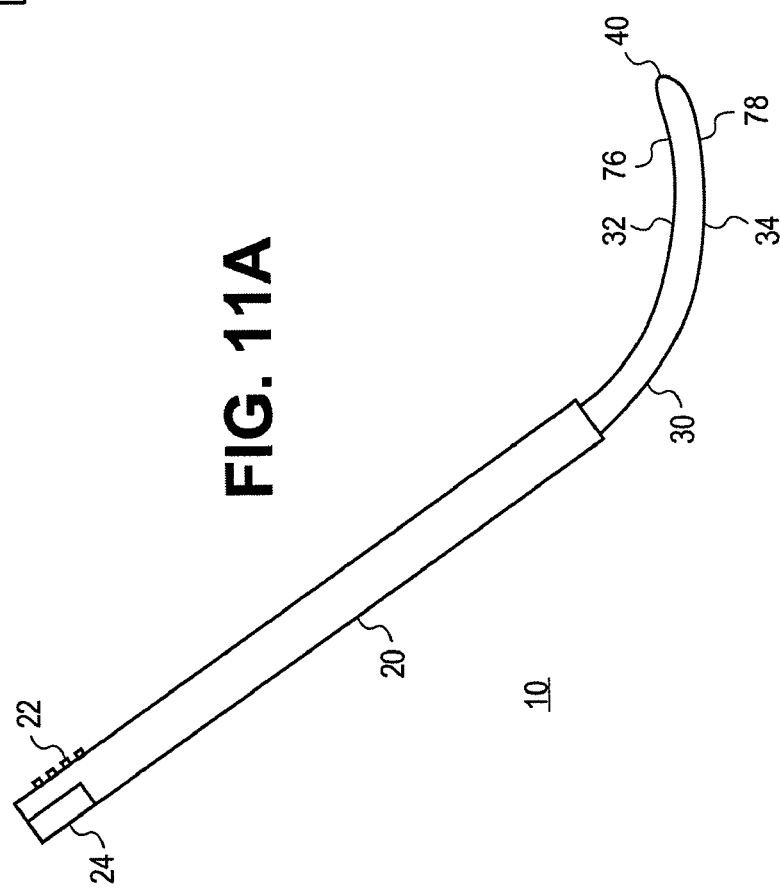
FIG. 11B
FIG. 11A

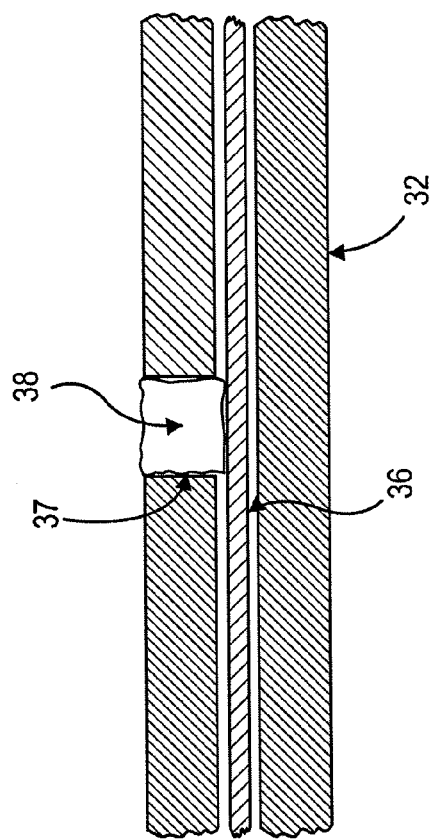
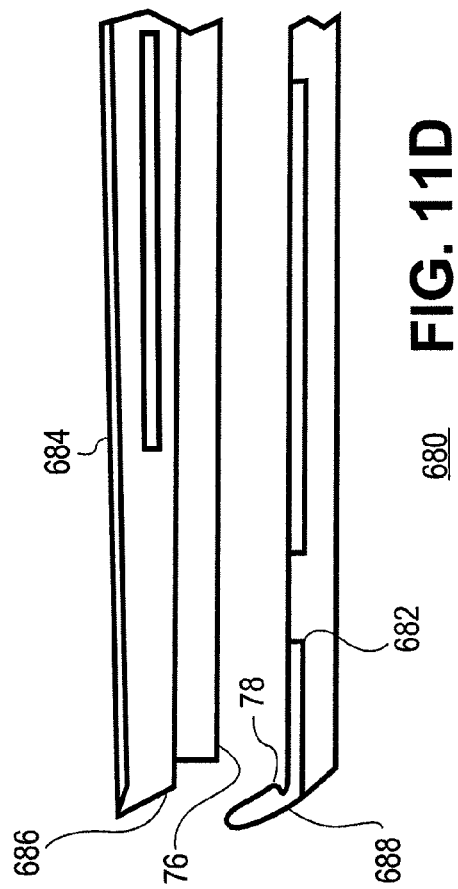
FIG. 11C
FIG. 11D

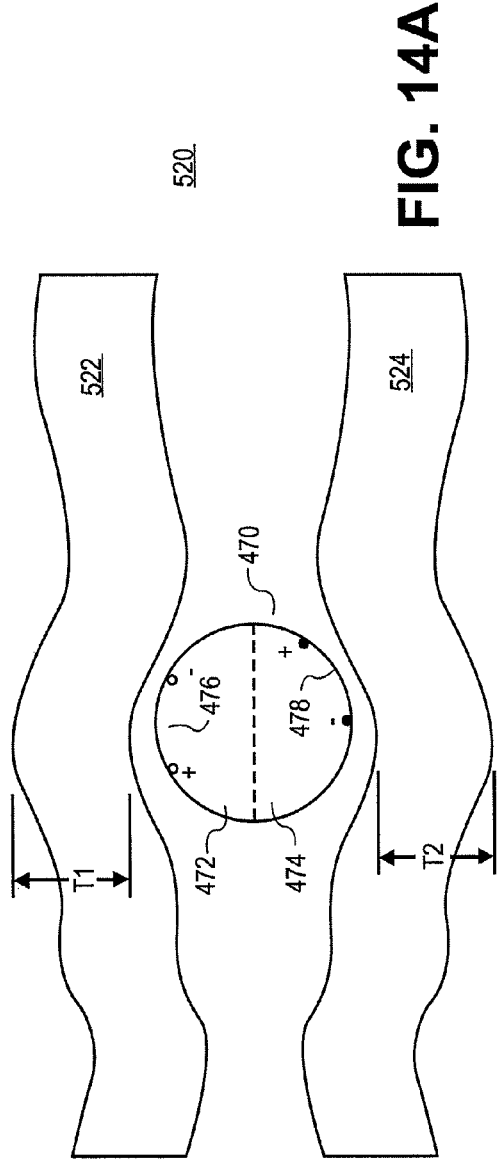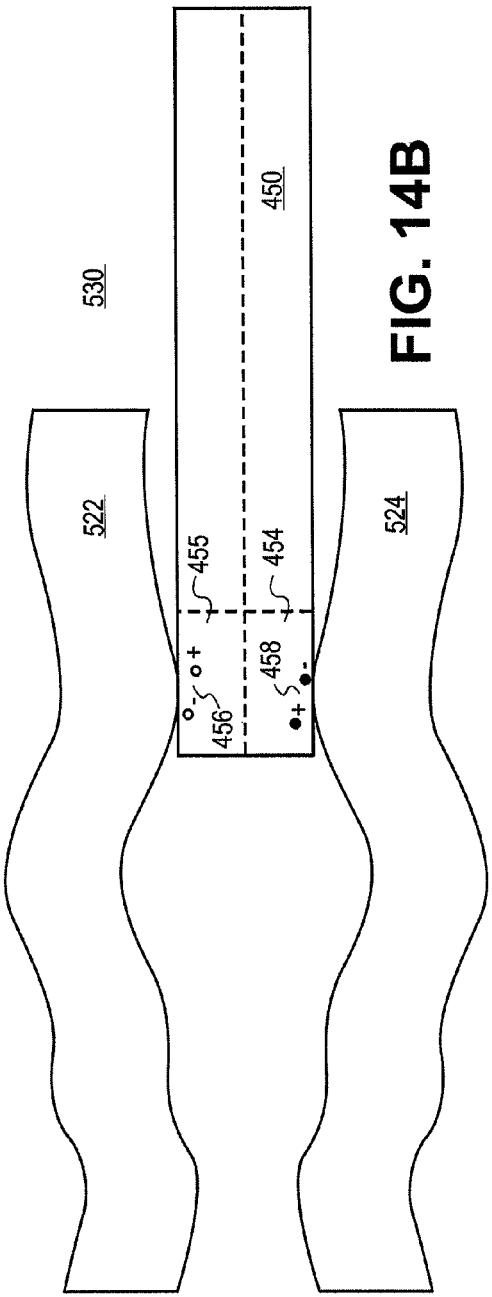

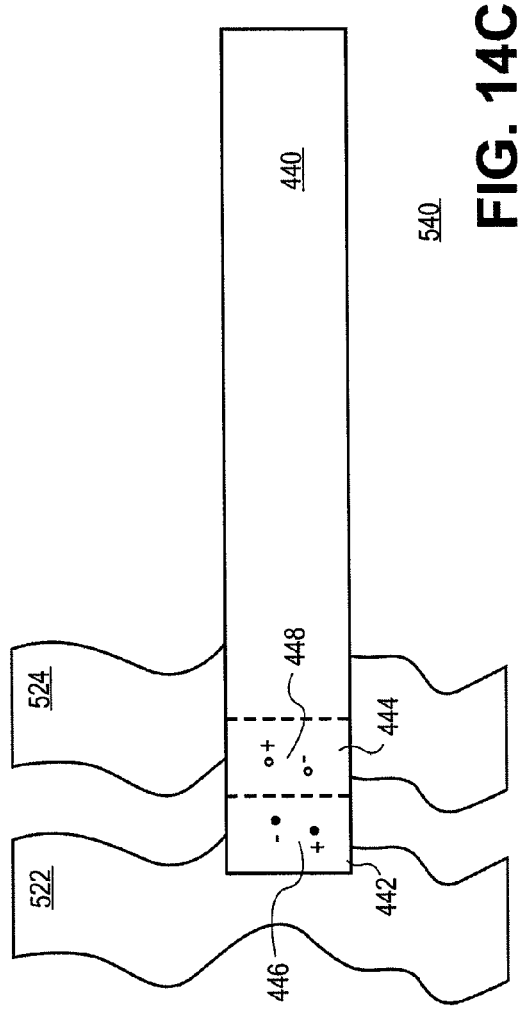
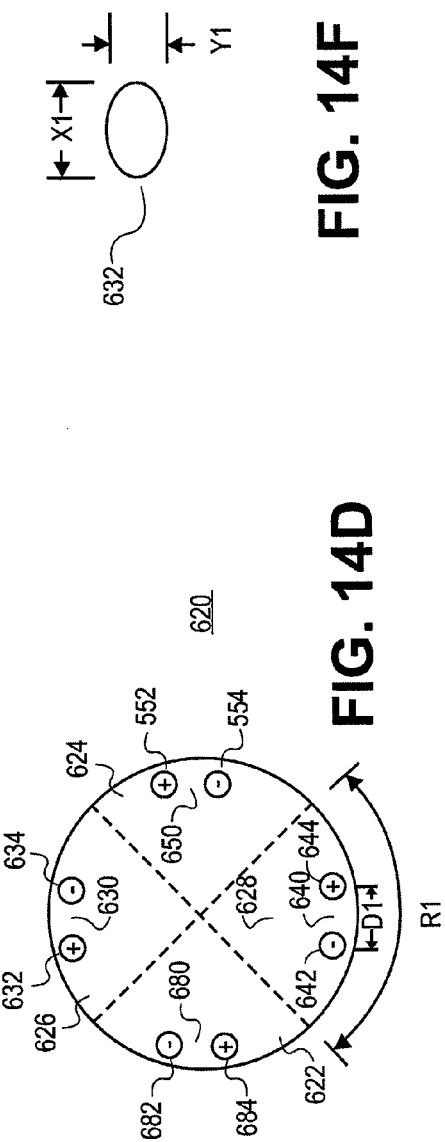

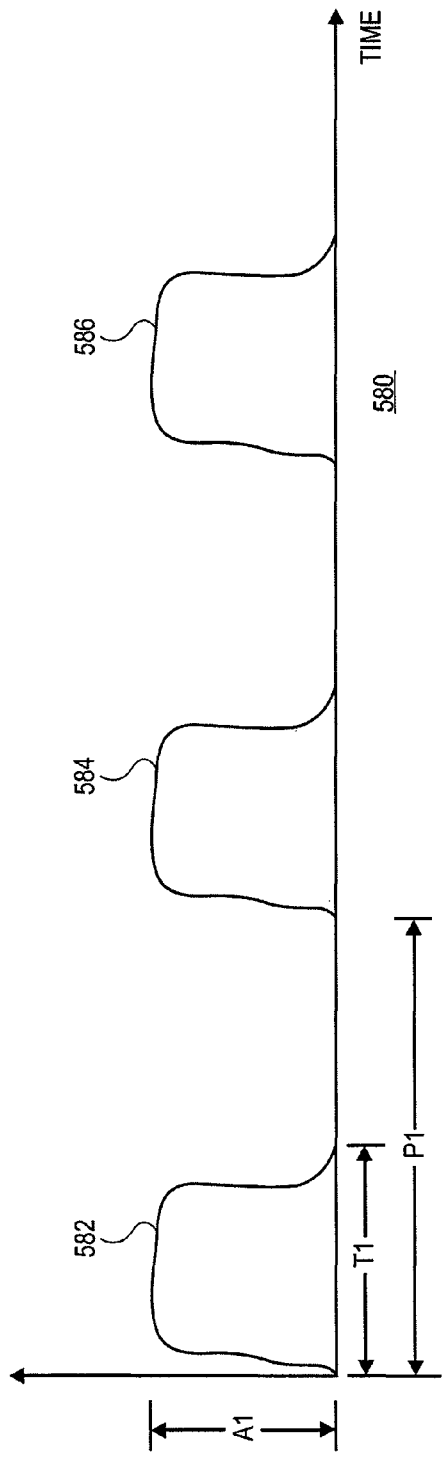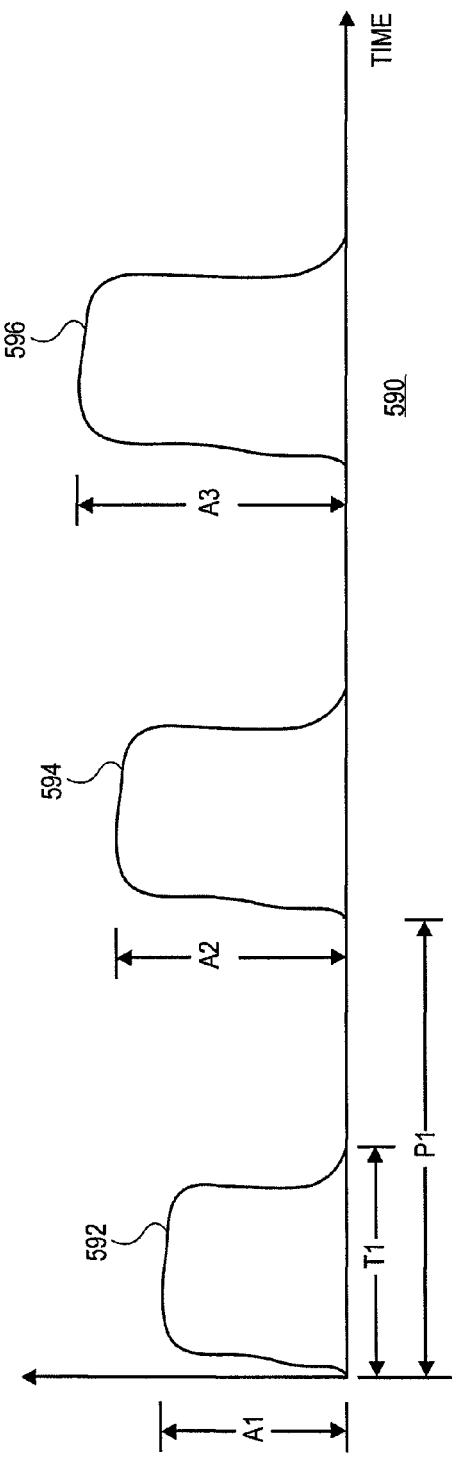

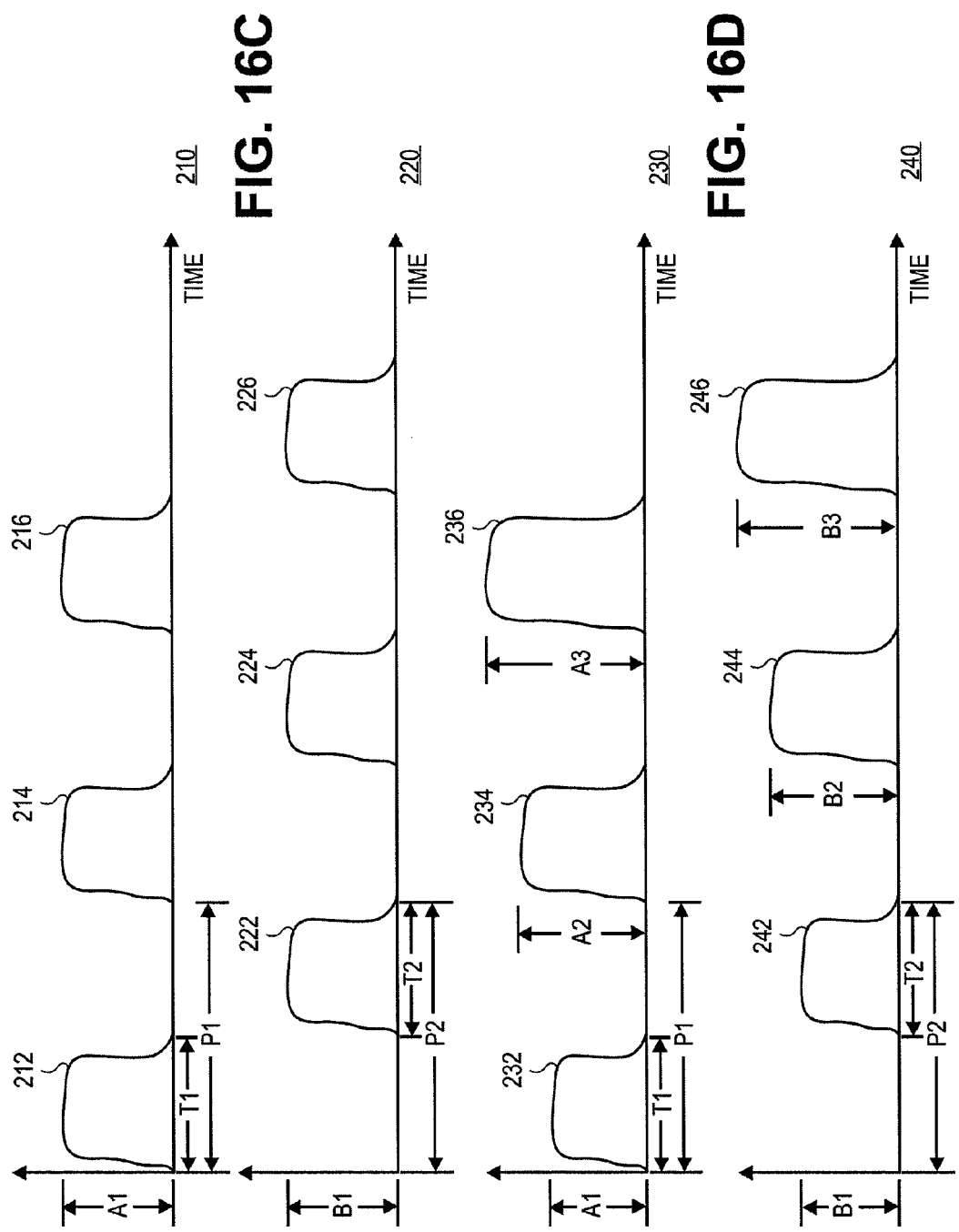

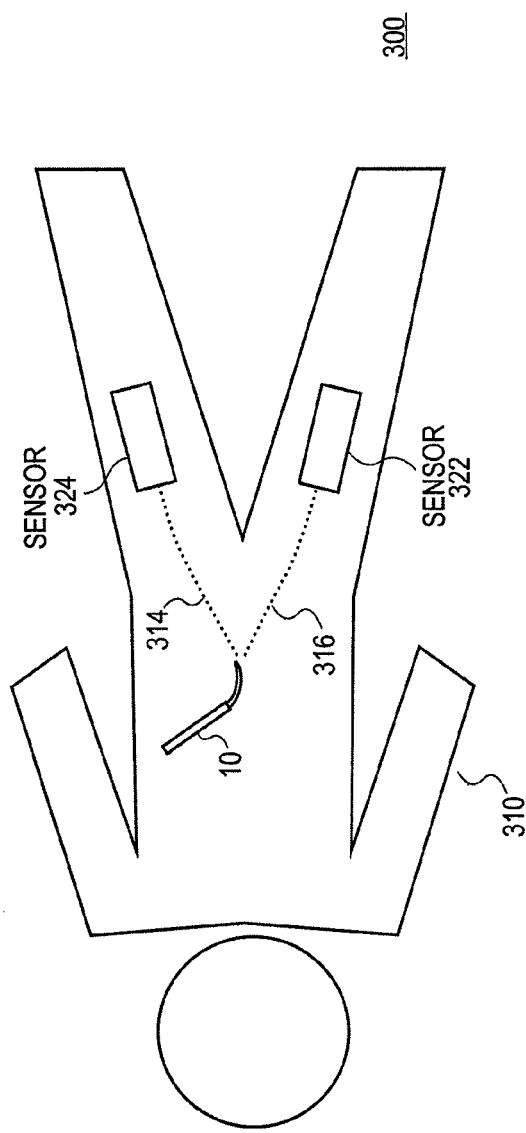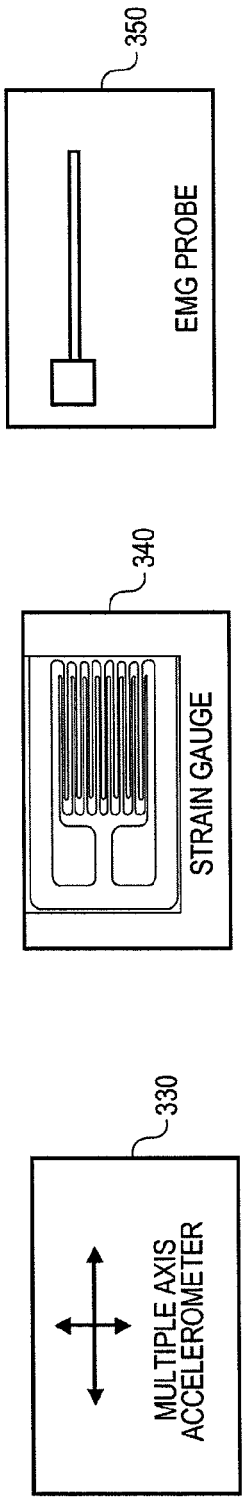

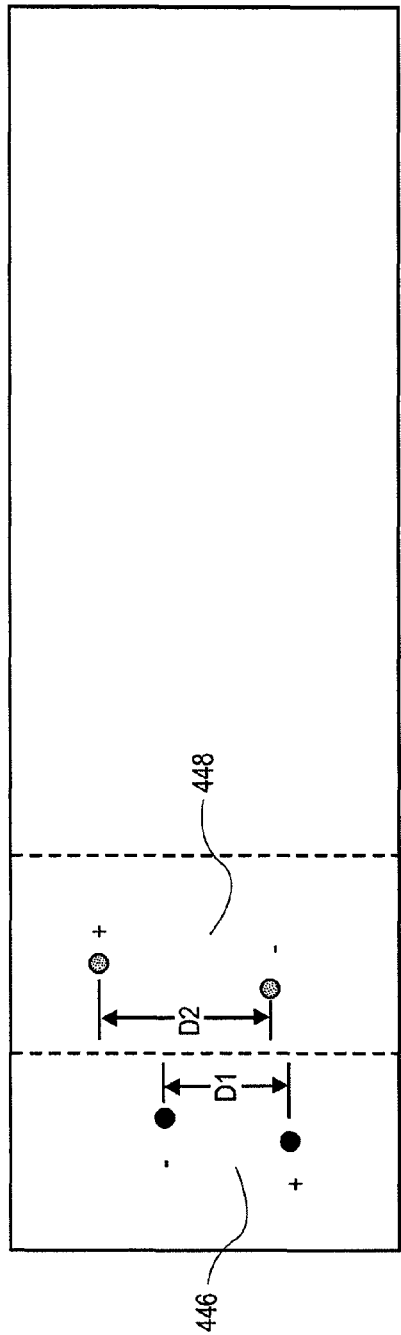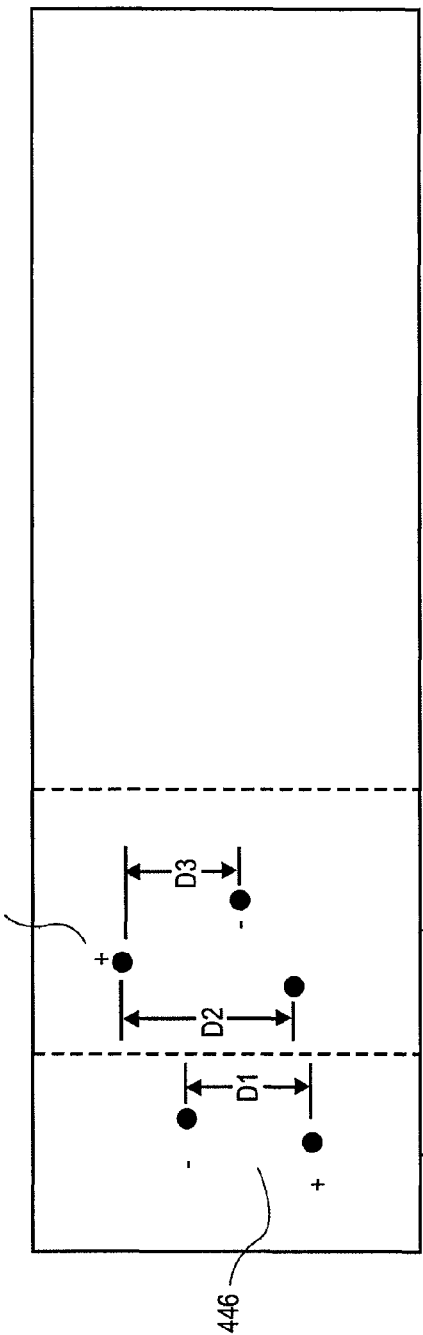

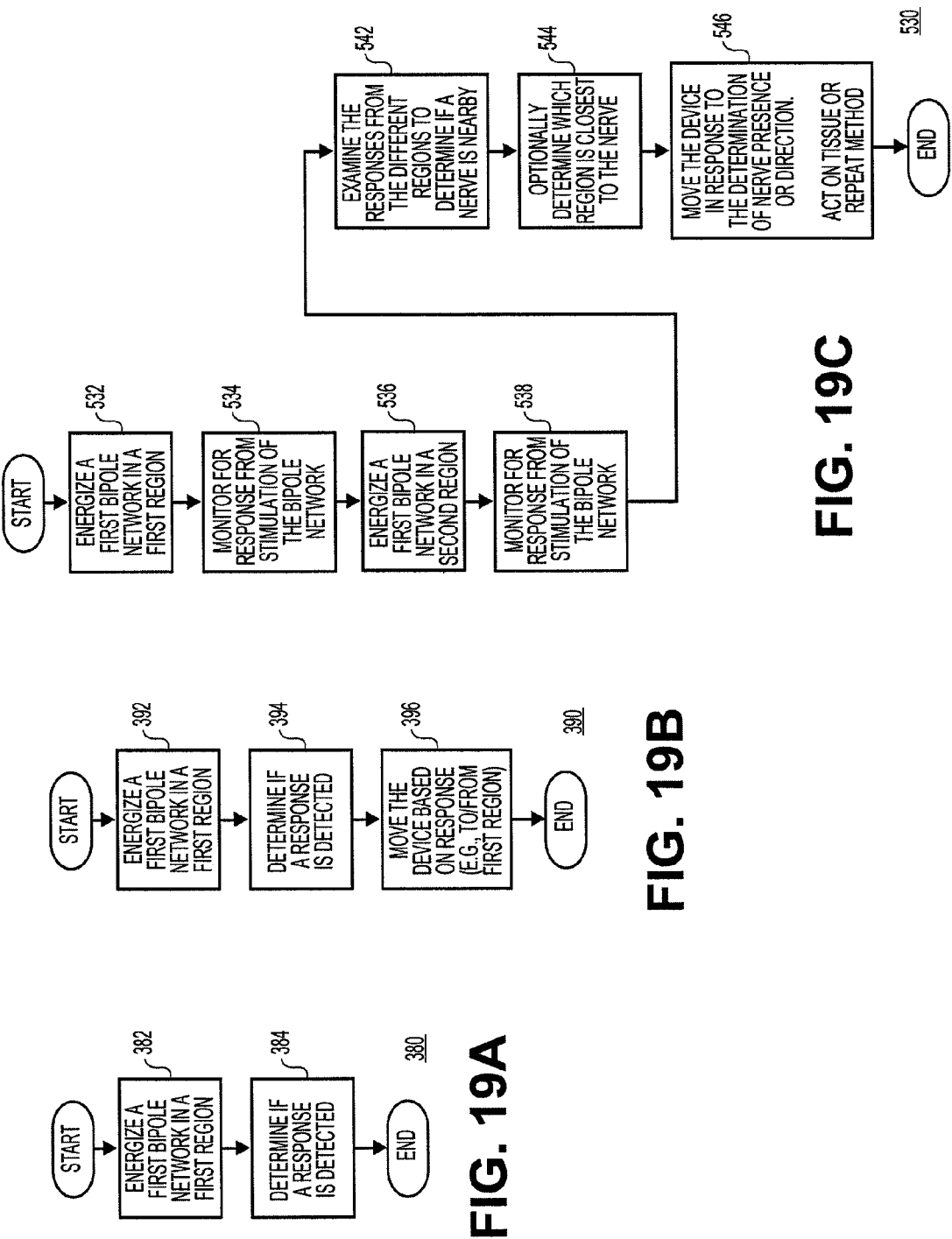

METHOD, SYSTEM, AND APPARATUS FOR NEURAL LOCALIZATION

CROSS-REFERENCE TO RELATED APPLICATIONS

This application claims priority to U.S. Provisional patent application Ser. No. 61/020,670, titled "DEVICES AND METHODS FOR TISSUE LOCALIZATION AND IDENTIFICATION", filed on Jan. 11, 2008; U.S. Provisional Patent Application Ser. No. 61/017,512, titled "METHOD, SYSTEM AND APPARATUS FOR TISSUE LOCALIZATION AND IDENTIFICATION", filed on Dec. 28, 2007; U.S. Provisional Patent Application Ser. No. 60/976,029, titled "METHOD AND APPARATUS FOR NEURAL LOCALIZATION", filed on Sep. 28, 2007; and U.S. Provisional Patent Application Ser. No. 60/970,458, titled "NERVE TISSUE LOCALIZATION SYSTEM", filed on Sep. 6, 2007. Each of these provisional patent applications is herein incorporated by reference in its entirety.

BACKGROUND OF THE INVENTION

Many types of surgical intervention require manipulation of one or more medical devices in close proximity to a nerve or nerves, and therefore risk damage to the nerve tissue. For example, medical devices may be used to cut, extract, suture, coagulate, or otherwise manipulate tissue including or near neural tissue. It would therefore be beneficial to precisely determine the location and/or orientation of neural tissue when performing a medical procedure.

Knowing the location or orientation of a nerve in relation to a medical device (e.g., a probe, retractor, scalpel, etc.) would enable more accurate medical procedures, and may prevent unnecessary damage to nearby nerves. Although systems for monitoring neural tissue have been described, these systems are relatively imprecise. Further, many of these systems require large current densities (which may also damage tissue) and may be severely limited in their ability to accurately guide surgical procedures. For example, in many such systems a current is applied from an electrode (e.g., a needle electrode) in order to evoke an efferent muscular response such as a twitch or EMG response. Such systems typically broadcast, via the applied current, from the electrode and the current passes through nearby tissue until it is sufficiently near a nerve that the current density is adequate to depolarize the nerve.

Because the conductance of biological tissue may vary between individuals, over time in the same individual, and within different tissue regions of the same individual, it has been particularly difficult to predictably regulate the applied current. Furthermore, the broadcast fields generated by such systems are typically limited in their ability to spatially resolve nerve location and/or orientation with respect to the medical device.

For example, US patent application 2005/0075578 to Gharib et. al. and US 2005/0182454 to Gharib et al. describe a system and related methods to determine nerve proximity and nerve direction. Similarly, U.S. Pat. No. 6,564,078 to Marino et al. describes a nerve surveillance cannula system and US 2007/016097 to Farquhar et al. describes a system and method for determining nerve proximity and direction. These devices generally apply electrical current to send current into the tissue and thereby depolarize nearby nerves. Although multiple electrodes may be used to stimulate the tissue, the devices, systems and methods described are do not substantially control the broadcast field. Thus, these systems may be limited by the amount of current applied, and the region over which they can detect nerves.

Thus, it may be desirable to provide devices, systems and methods that controllably produce precise electrical broadcast fields in order to stimulate adjacent neural tissue, while indirectly or directly monitoring for neural stimulation (e.g. EMG, muscle movement, or SSEP), and thereby accurately determine if a nerve is in close proximity to a specified region of the device.

SUMMARY OF THE INVENTION

Described herein are devices, systems and methods for determining if a nerve is nearby a region of a device. In general, the devices may include one or more bipole pairs that can be excited by the application of a current or voltage to produce a bipole field between the anode(s) and cathode(s). These bipoles may be referred to as "tight" bipole pairs because the bipole field produced is limited to the adjacent region relatively near the surface of the device. In some variations the bipole field is formed by a bipole network comprising a plurality of anodes and cathodes arranged along an outer surface of the device. Multiple bipole pairs or multiple bipole networks maybe arranged in different regions along the outer surface of the device.

For example, described herein are devices that are capable of determining if a nerve is nearby a region of the device. These devices may include an elongate body having an outer surface, and a bipole network arranged along the outer surface. The bipole network typically includes a plurality of anodes and a plurality of cathodes, wherein the plurality of anodes and the plurality of cathodes are configured to form an effectively continuous bipole field along a portion of the device's outer surface.

In some variations the plurality of anodes are in electrical communication with a first anodal conductor. For example, the plurality of anodes may all be positioned in a single region of the device (e.g., the outer surface of the device) and may all connect to a single connector. In some variations the plurality of anodes are effectively formed from a single anode. For example, all of the anodes in a particular region may be formed from a single anodal wire. Individual anodes forming the bipole network may be formed as openings (or uninsulated regions) through the body of the device electrically exposing the anodal conductor (e.g., wire).

Similarly, any of the devices described herein may include a plurality of cathodes that are all in electrical communication with a first cathodal conductor. As mentioned for the anodes, the cathodes forming a bipole network may be formed from the same cathodal conductor, such as a wire having multiple regions that are exposed (or uninsulated) to form the cathodes.

Alternatively, in some variations the individual anodes and/or cathodes forming the bipoles of the devices described herein (including the bipoles of a bipole network) may be separately connected to the power supply and/or controller. For example, each anode and/or cathode may be separately wired back to the controller, allowing individual control of each anode and/or cathode.

The anodes and cathodes forming the bipole network may be arranged so that the current from a particular cathode or anode passes substantially to an adjacent cathode or anode rather than spreading out or broadcasting. Thus, the broadcast field formed when the bipoles are excited by the application of energy may be limited or controlled. For example, each anode of a bipole network may be located less than 2 mm from at least one cathode. In some variations the anodes and cathodes form an alternating pattern (e.g., of adjacent anodes/cathode/anode). As used herein, a bipole network (or a plurality of bipoles) may be formed as a "tripolar" electrode arrangement, in which an anode is adjacent to two cathodes, or a cathode is adjacent to two anodes.

In some variations, the anodes forming a bipole network are arranged in a line. Similarly, the cathodes may be formed in a line. For example, when the anodes of a bipole network are formed from a single anodal conductor such as an insulated wire, the openings through the electrical insulator that expose the wire may be arranged in a line (including a curved or straight line). In some variations, an anodal wire forms the anodes of a bipole network, and a cathodal wire forms the cathodes of the bipole network, and the wires are arranged in parallel with each other on or in the body of the device. In some variations, the anodal and cathodal wires are arranged in a helical pattern.

The electrodes forming a bipole may have any appropriate dimension, particularly relatively smaller dimensions. For example, the anode and/or cathode may have a surface area of less than 5 mm (or less than 3 mm$^2$, less than 2 mm$^2$, less than 1 mm$^2$, etc.). The cathode may be the same size as the anode, or the sizes of the cathodes and anodes may be different.

Some device variations have a plurality of bipole networks that are arranged in a non-overlapping fashion along the outer surface. For example, the outer surface of the device may contain two or more regions that each includes a bipole network.

Also described herein are devices capable of determining if a nerve is nearby one or more regions of the device that include an outer surface having a first region and a second region, a first bipole network comprising a plurality of anodes and a plurality of cathodes, wherein the plurality of anodes and the plurality of cathodes are configured to form an effectively continuous bipole field along the first region of outer surface, and a second bipole network comprising a plurality of anodes and a plurality of cathodes, wherein the plurality of anodes and the plurality of cathodes are configured to form an effectively continuous bipole field along the second region of outer surface.

As described above, the plurality of anodes in the first bipole network may be formed along a first anodal conductor and the plurality of cathodes in the first bipole network may be formed along a first cathodal conductor. Similarly, the plurality of anodes in the second bipole network may be formed along a second anodal conductor and the plurality of cathodes in the second bipole network may be formed along a second cathodal conductor.

The dimension and arrangement of the anodes and cathodes within each bipole network may be formed as described above.

In some variations, the bipole field formed along the first region of the outer surface does not overlap with the bipole field formed along the second region of the outer surface. For example, the substantially continuous bipole filed may be formed by applying current or voltage simultaneously to all of the anodes and cathodes so that the bipole filed extends between adjacent anodes and cathodes to form a region in which the bipole fields connect the adjacent anodes and cathodes to form a stitched together length. This substantially continuous bipole filed provides a length along the surface of the device which may be used to detect a nerve near this region of the surface. For example, the plurality of anodes of the first bipole network may be arranged in a line.

In some variations, a first connector electrically is connected to the anodes of the first bipole network and a second connector electrically connected to the cathodes of the first bipole network. For example, the anodes of the first bipole network may be formed from a single anodal conductor and the cathodes of the first bipole network may be formed from a single cathodal conductor. Similarly a third connector may be electrically connected to the anodes of the second bipole network and a fourth connector electrically may be connected to the cathodes of the second bipole network.

Also described herein are devices capable of determining if a nerve is nearby one or more regions of the device that include an outer surface having a first region and a second region, a first bipole network in the first region and a second bipole network in the second region. The first bipole network may include a plurality of anodes in electrical communication with a first anodal conductor and a plurality of cathodes in electrical communication with a first cathodal conductor, wherein the plurality of anodes and the plurality of cathodes are configured to form an effectively continuous bipole field along the first region of outer surface. The second bipole network in the second region may include a plurality of anodes in electrical communication with a second anodal conductor, and a plurality of cathodes in electrical communication with a second cathodal conductor, wherein the plurality of anodes and the plurality of cathodes are configured to form an effectively continuous bipole field along the second region of outer surface.

As mentioned above, the bipole field formed along the first region may not overlap with the bipole field formed along the second region when these bipole fields are excited.

Also described herein are devices capable of determining if a nerve is nearby a region of the device that include an elongate body having an outer surface, wherein the outer surface includes a first region and a second region, a first bipole network in the first region, and a second bipole network in the second region. The first bipole network may include a first anodal conductor forming a plurality of anodes within the first region, and a first cathodal conductor forming a plurality of cathodes within the first region. The plurality of anodes and the plurality of cathodes in the first region may be configured to form a substantially continuous bipole field in the first region. Similarly, the second bipole network in the second region may include a second anodal conductor forming a plurality of anodes located within the second region and a second cathodal conductor forming a plurality of cathodes located within the second region, wherein the plurality of anodes and the plurality of cathodes in the second region are configured to form a continuous bipole field in the second region.

Also described herein are devices capable of determining if a nerve is nearby a region of the device that include an elongate body having an outer surface and a plurality of anodes and cathodes on the outer surface, wherein the anodes and cathodes are arranged to form a substantially continuous broadcast field between the plurality of anodes and cathodes such that the broadcast field is formed by adjacent bipole pairs of anodes and cathodes which share either an anode or cathode.

As mentioned, the plurality of anodes may be in electrical communication with a first anodal conductor, and the plurality of cathodes may be in electrical communication with a first cathodal conductor. In this variation, bipole pairs (formed by an anode and cathode) are arranged adjacent to each other so that they can form a substantially continuous broadcast field (e.g., bipole filed). Thus, adjacent bipole pairs share either a cathode or an anode, and an anode may communicate electrically with one or more adjacent cathode, and a cathode may communicate with one or more adjacent anodes. This arrangement allows a single network (in some cases formed by a single cathodal conductor and a single anodal conductor) to span a larger region of the surface using a relatively small exposed electrode area. As described below, there may also be advantages in the ability to detect adjacent nerves based on the multiple field orientations.

In some variations, the device also includes a second, non-overlapping plurality of anodes and cathodes on the outer surface configured to form a substantially continuous broadcast field between the second plurality of anodes and cathodes such that the broadcast field is formed by adjacent bipole pairs of anodes and cathodes which share either an anode or cathode. For example, multiple regions on the surface (including more than two) may each include a plurality of anodes and cathodes configured to form a substantially continuous broadcast field.

For example, a device capable of determining if a nerve is nearby a region of the device may include an elongate body having an outer surface, wherein the outer surface includes a first region and a second region, a plurality of anodes and cathodes in the first region, wherein the anodes and cathodes are arranged in the first region to form a substantially continuous broadcast field between the plurality of anodes and cathodes such that the broadcast field is formed by adjacent bipole pairs of anodes and cathodes which share either an anode or cathode, and a plurality of anodes and cathodes in the second region, wherein the anodes and cathodes are arranged in the second region to form a substantially continuous broadcast field between the plurality of anodes and cathodes such that the broadcast field is formed by adjacent bipole pairs of anodes and cathodes which share either an anode or cathode. The broadcast field of the first region does not substantially overlap with the broadcast field of the second region.

For example, also described herein are devices capable of determining if a nerve is nearby a region of the device that include an outer surface, a plurality of adjacent bipolar electrode pairs within a first region of the surface, wherein the bipolar electrode pairs are formed by alternating anodes and cathodes such that adjacent bipole pairs share either an anode or a cathode, wherein the anodes in the first region are electrically continuous and the cathodes in the first region are electrically continuous and the adjacent bipole pairs form an angle of less than 180 degrees. This arrangement may also be referred as forming a "zigzag" pattern of bipole pairs.

Also described herein are systems capable of determining if a nerve is nearby one or more regions of a device. The systems may include any of the variations of the devices described herein as well as one or more additional elements. For example, a system capable of determining if a nerve is nearby one or more regions of a device and a controller. The device may include a device with an outer surface having a first region and a second region, a first bipole network including a plurality of anodes and a plurality of cathodes, wherein the plurality of anodes and the plurality of cathodes are configured to form an effectively continuous bipole field along the first region of outer surface, and a second bipole network including a plurality of anodes and a plurality of cathodes, wherein the plurality of anodes and the plurality of cathodes are configured to form an effectively continuous bipole field along the second region of outer surface. The controller may be configured to switch between applying energy to form the bipole field of the first bipole network or applying energy to form the bipole field of the second bipole network.

The system may also include a power source connected to the controller. The power source may be a battery. In some variations the system includes one or more sensors. In particular, the sensors may be configured for detecting stimulation of a nerve. For example, motion detectors, muscle twitch detectors, nerve depolarization detectors, EMG detectors, etc.

As already described, in some variations of the device, the plurality of anodes in the first bipole network may be in electrical communication with a first anodal conductor and the plurality of cathodes in the first bipole network may be in electrical communication with a first cathodal conductor; similarly the plurality of anodes in the second bipole network may be in electrical communication with a second anodal conductor and the plurality of cathodes in the second bipole network may be in electrical communication with a second cathodal conductor.

Any of the features or arrangements of the devices described herein may be part o the systems for determining if a nerve is nearby one or more regions of a device.

Also described herein are device for determining if a nerve is nearby a region of the device that only require a single tight bipole pair in each region of the outer diameter of an elongate member. For example, described herein are devices for determining if a nerve is nearby including an elongate device with an outer surface having a first circumferential region and a second circumferential region, a first tight bipole pair within the first circumferential region, wherein the first tight bipole pair comprises an anode and a cathode that are separated by a distance that is less half the length of the first circumferential region, and a second tight bipole pair within the second circumferential region, wherein the second tight bipole pair comprises an anode and a cathode that are separated by a distance that is less than half the length of the second circumferential region, wherein the broadcast field of the first bipole pair does not overlap with the broadcast field of the second bipole pair.

In some variations, each anode is located less than 2 mm from at least one cathode. Further, each anode may have a surface area of less than 5 $mm^2$, and/or each cathode may have a surface area of less than 5 $mm^2$ (e.g., less than 3 $mm^2$, less than 2 $mm^2$, less than 1 $mm^2$, etc.). In some variations, the first tight bipole pair is separated from the second tight bipole pair by a distance that is greater than the distance separating either the first tight bipole pair or the second tight bipole pair.

Also described herein are systems for determining if a nerve is nearby a region of a probe that include an elongate probe with a surface having a first region and a second region, a first tight bipole pair within the first region, a second tight bipole pair within the second region (wherein the broadcast field of the first tight bipole pair does not substantially overlap with the broadcast field of the second tight bipole pair), and a controller configured to switch between the first or second tight bipole pairs so that energy may be applied to either the first or second tight bipole pairs, wherein the system is configured to enable determination of whether the tissue is detectably closer to the first region or the second region.

This system, as with any of the systems described herein, may include a power supply connected to the controller, wherein the controller regulates the power applied to the tight bipole pairs. The system may also include one or more sensors, such as a sensor for determining stimulation of a nerve.

Also described herein are devices for determining if a nerve is nearby the device that includes one or more rotatable bipole pairs. For example, described herein are devices for determining if a nerve is nearby the device, the device including an elongate body having an outer body surface and a plurality of circumferential regions, a scanning surface that is movable with respect to the outer body surface, and a bipolar electrode pair connected to the scanning surface, wherein the bipole pair comprises an anode and a cathode configured to form a bipole field, wherein the scanning surface is configured to scan the bipolar electrodes across at least two of the circumferential regions to determine if a nerve is near a circumferential region.

The device may also include a controller configured to control the scanning of the bipolar electrode pair. In some variations the devices also include a driver for driving the motion of the scanning surface. The driver may be a motor or other moving mechanism that drives the movement of the bipole pair. The device may also include an output for indicating which circumferential region the bipolar electrode pair corresponds to. For example, as the bipole pair is rotated, the output may indicate where around the circumference of the elongate body the bipole pair is positioned. This may help coordinate the location of the nerve relative to the probe.

The scanning surface (including the bipole pair(s)) may be movable in any appropriate fashion. For example, in some variations the scanning surface is rotatable with respect to the outer body surface.

In some variations, the scanning surface includes a plurality of bipolar electrode pairs.

In operation, any of the devices and systems described herein may be used to determine if a nerve is nearby the device.

For example, a method of determining if a nerve is nearby a region of a device may include the steps of energizing a first tight bipole pair within a first circumferential region of the device to form a first broadcast field, energizing a second tight bipole pair within a second circumferential region of the device to form a second broadcast field, and determining if a nerve has been stimulated by either the first broadcast field or the second broadcast field.

The step of energizing the second tight bipole pair may include forming a second broadcast field that does not substantially overlap with the first broadcast field. Thus, energy (e.g., current, voltage) may be applied to the bipole pairs (which may be a bipole network) of different circumferential regions at different times in order to determine which region is closer to the device.

The method may also include the step of determining whether a nerve is closer to the first circumferential region or the second circumferential region. In some variations the method includes the step of monitoring the output of the nerve, such as muscle twitch, EMG, SSEP, or other methods for determining depolarization of the nerve, directly or indirectly. If the nerve is depolarized when stimulating the bipole pair(s) in one region but not when stimulating other regions, then the nerve is likely closer to the region that resulted in stimulation. Alternatively, if the nerve is stimulated after exciting bipole pairs from more than one region, the nerve may be relatively near all of these regions, but may be assumed to be closer to the region that results in the greatest output response.

The method may also include switching between the bipole pairs to apply energy. Thus, the energy may be applied separately (in time) between different regions.

Also described herein are methods of determining if a nerve is nearby a region of a device using a moving bipole pair. For example, the method may include the steps of energizing a bipolar electrode pair, scanning the bipolar electrode pair across a plurality of circumferential regions of the outer surface of an elongate body, and determining if a nerve has been stimulated. The method may also include determining which circumferential region corresponds to the stimulation of a nerve.

The step of scanning the bipolar electrode pair includes rotating the bipole pair with respect to the outer surface of the elongate body. In some variations, the step of energizing a bipolar electrode pair comprises energizing a plurality of bipolar electrode pairs.

Also described herein are methods of determining if a nerve is nearby a device when the bipole pair forms part of a bipole network in an outer surface region of a device. For example, a method of determining if a nerve is nearby a device may generally include energizing a plurality of bipolar electrodes within a first region of an outer surface of the device to form a first substantially continuous broadcast field, and determining if a nerve has been stimulated by energizing the first substantially continuous broadcast field.

The method may also include the steps of energizing a plurality of bipolar electrodes within a second region of an outer surface of the device to form a second substantially continuous broadcast field when not energizing the plurality of electrodes within the first region, and determining if a nerve has been stimulated by the second substantially continuous broadcast field. In some variations, the method includes the steps of determining whether a nerve is closer to the first region or the second region.

Also described herein are methods of determining if a nerve is nearby a device including the steps of energizing a plurality of bipolar electrodes within a first region of an outer surface of the device, energizing a plurality of bipolar electrodes within a second region of an outer surface of the device, and determining whether a nerve is closer to the first region or the second region. The plurality of bipole pairs within the first region may be substantially simultaneously energized. The plurality of bipole pairs within the second region may be substantially simultaneously energized.

Also described herein are methods of determining if a nerve is nearby a device including the steps of energizing a plurality of bipolar electrodes within a first region of an outer surface of the device to form a first substantially continuous broadcast field, energizing a plurality of bipolar electrodes within a second region of an outer surface of the device to form a second substantially continuous broadcast field, wherein the second broadcast field does not overlap with the first broadcast field, and determining whether a nerve is closer to the first region or the second region.

Another method of determining if a nerve is nearby a device includes energizing a plurality of bipolar electrodes within a first region of an outer surface of the device, wherein the plurality of bipolar electrodes comprise one or more anodes electrically connected to a first anodal conductor and one or more cathodes electrically connected to a first cathodal conductor, energizing a plurality of bipolar electrodes within a second region of an outer surface of the device, wherein the plurality of bipolar electrodes comprise one or more anodes electrically connected to a second anodal conductor and one or more cathodes electrically connected to a second cathodal conductor, and determining whether a nerve is closer to the first region or the second region.

Any of the devices described herein may be used as part of a treatment method for treating tissue that includes the method of determining if a nerve is nearby the device. The device may be a treatment device or a device involved in the procedure. Thus, any of the devices described herein may be integrated into known devices or instruments.

For example, a method of determining if a nerve is nearby a device may include the steps of positioning a device within a tissue, wherein the device comprises a plurality of circumferential regions around the device, wherein each circumferential region includes a plurality of electrodes comprising at least one bipole pair, energizing the electrodes in a first circumferential region to a plurality of stimulation levels, determining a first stimulation level from the plurality of stimulation levels based on a response of a nerve, energizing the electrodes in the other circumferential regions to the first stimulation level, and determining which circumferential region the nerve is nearest to. The step of energizing the electrodes in the first circumferential region may include energizing the electrodes in to a plurality of increasing stimulation levels. In some variations, the electrodes within each circumferential region may comprise a plurality of bipole pairs configured to form a substantially continuous broadcast field when energized.

The step of energizing the electrodes in the first circumferential region may comprises energizing the electrodes to increasing stimulation levels between 0.001 mV and 100 mV (e.g., between 0.01 mV and 10 mV, etc.). In some variations the step of energizing the electrodes includes applying a ramp of stimulation at increasing levels (e.g., increasing voltage). The step of determining the first stimulation level may include determining the first stimulation level at which the nerve responds.

In some variations, the step of energizing the electrodes in the other circumferential regions comprises sequentially energizing the electrodes in the other circumferential regions.

The step of determining which circumferential region the nerve is nearest to may include determining which circumferential region evokes the largest response from the nerve when the electrodes within that circumferential region are energized to the first stimulation level.

INCORPORATION BY REFERENCE

All publications and patent applications mentioned in this specification are herein incorporated by reference in their entirety, as if each individual publication or patent application was specifically and individually indicated to be incorporated by reference in its entirety.

BRIEF DESCRIPTION OF THE DRAWINGS

FIG. 1A shows an example of a generic device including an elongate body and a bipole pair.

FIGS. 1B and 1C show a tight bipole pair.

FIGS. 1D-1F show bipole networks.

FIGS. 2A-2D are various views of portions of a neurostimulation device, according to one embodiment of the present invention.

FIGS. 5A and 5B illustrate side views and cross-sectional views, respectively, of one variation of a portion of a nerve localization device.

FIGS. 6A and 6B illustrate side views and cross-sectional views, respectively, of another variation of a portion of a nerve localization device.

FIGS. 7A and 7B illustrate side views and cross-sectional views, respectively, of another variation of a portion of a nerve localization device.

FIG. 8 is a side view of a nerve localization device showing multiple current path direction features.

FIGS. 11A-11C are simplified diagrams of one variation of a nerve localization device.

FIG. 11D is a partial, simplified diagram of a rongeur tip configured as a nerve localization device.

FIGS. 14A-14B illustrate one variations of a device employed in tissue.

FIG. 14C illustrates another variation of a device in tissue.

FIGS. 14D and 14E show a cross-section and a partial perspective view, respectively, of a device having an elongate body including four regions.

FIG. 14F show a schematic illustration of an electrode that may form part of a tight bipole pair.

FIGS. 16A-16D illustrate exemplary signals that may be applied to one or more bipole pairs or networks within a region of a device.

FIG. 17A illustrates a system for determining if a nerve is nearby applied to a patient.

FIG. 17B-17D are simplified diagrams of sensors which may be used as part of a system for determining if a nerve is nearby.

FIGS. 18A-18B illustrate variations of a device for determining if a nerve is nearby.

FIGS. 19A-19C are flow diagrams illustrating method of determining if a nerve is nearby a region of a device.

DETAILED DESCRIPTION OF THE INVENTION

Figure 2A:
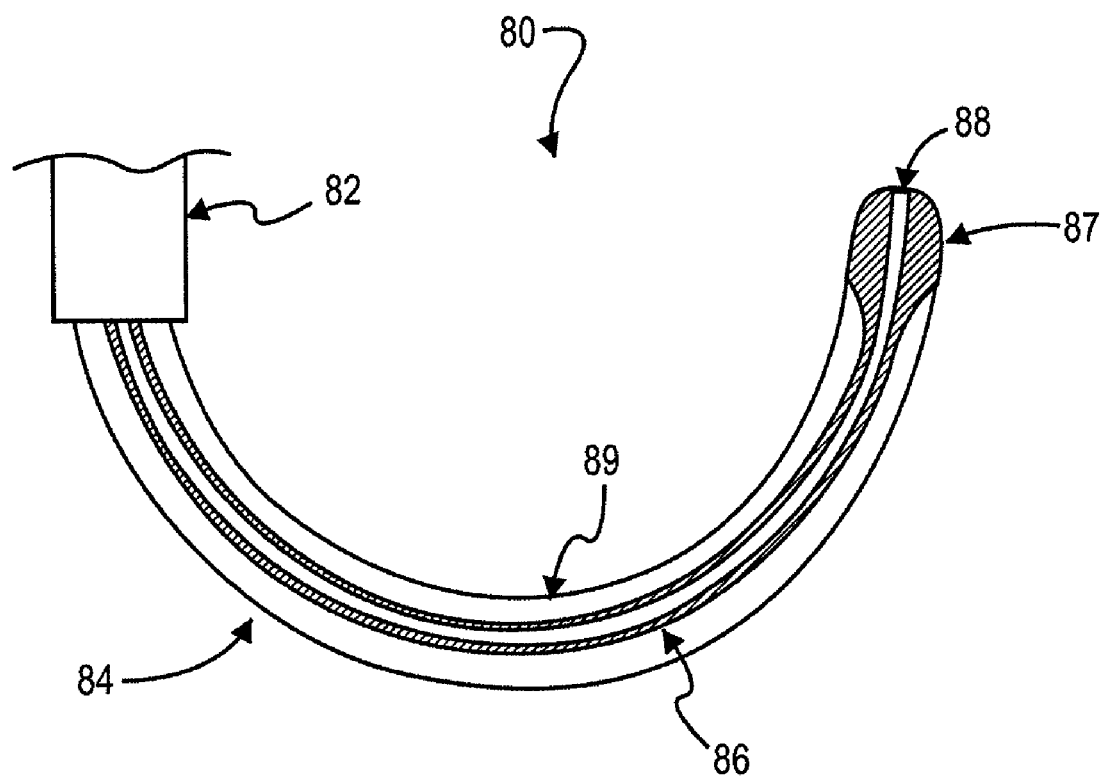

Described herein are devices, systems and methods for determining if a nerve is nearby a device or a region of a device. In general, a device for determining if a nerve is nearby a device includes an elongate body having an outer surface with one or more bipoles arranged on the outer surface. These bipoles may also be referred to as tight bipoles, and include a cathode and an anode that are spaced relatively close together to form a limited broadcast field. The broadcast field may be referred to as the bipole field, or the field formed by the excitation of the bipole pair. In general, the bipole filed is a controlled or "tight" broadcast field that extends from the bipole pair(s).

A device for determining if a nerve is nearby the device may be referred to as a nerve localization device, a localization device, or a neurostimulation device. The elongate body region of the device may be referred to as a probe, although it should be understood that any appropriate surgical or medical device may be configured as a device for determining if a nerve is nearby the device. Particular examples of such devices are described below. For example, FIG. 1A shows a generic device 1 configured as a nerve localization device that having an elongate body 5 that may be configured to determine if a nerve is nearby.

The outer surface of a device for determining if a nerve is nearby a region of the device may have two or more regions. In some variations, each region includes two or more bipole pairs that are arranged to detect a nearby nerve. The regions may be arranged around or along the outer surface of the device. For example, the regions may be circumferential regions that divide the outer surface up along the circumference. Examples of different regions are described below. Each region may include one or more bipole pairs, which may be used to detect a nearby nerve.

Returning to FIG. 1A, the elongate body 5 has an outer surface with a blunt (atraumatic) end. In general, the outer body of the device 5 may be formed of any appropriate material, including polymeric materials such as PEBAX, PEEK or the like. Non-conducting and biocompatible materials may be particularly preferred. In FIG. 1A, a single bipole pair 7 is shown near the distal end of the device. FIG. 1B illustrates an approximation of the current lines for a dipole pair, including the cathode 8 and the anode 6. These current lines reflect the dipole field to broadcast field for the dipole pair.

A tight bipole pair may have a very limited broadcast field, as reflected in FIG. 1C, which shows the bipole pair of FIG. 1B having only the major current line. In some variations the size of the anode 6 and cathode 6 forming the bipole pair are relatively small, particularly (e.g., less than 5 $mm^2$, less than 3 $mm^2$, less than 2 $mm^2$, less than 1 $mm^2$), and the anode and cathode are positioned sufficiently nearby so that the majority of current passes between the anodes and cathodes. For example, the anode and cathode of a bipole pair may be separated by less than 5 mm, less than 2 mm, less than 1 mm, etc.

The limited broadcast field may allow stimulation of only nerves that are very near the bipole pair. This may enhance accuracy, and help prevent or limit tissue damage, particularly at the low stimulation.

When a region of the outer surface of a device includes more than one bipole, the bipoles may be arranged as a bipole network. A bipole network includes at least two bipoles that are formed by at least three electrodes (e.g., two anodes and a cathode or two cathodes and an anode). The bipole network is typically arranged so that all of the bipoles in the network are activated synchronously to create an effectively continuous bipole field along the outer surface. For example, FIGS. 1D and 1E illustrates an example of an effectively continuous bipole filed. In this example, the anodes and cathodes forming the bipolar network are arranged so that the current between the two electrodes forms a zigzag pattern. Bipole pairs are located adjacent to each other and share either an anode or a cathode. FIG. 1F illustrates another example of a bipole network, in which adjacent bipole pairs do not share anode or cathodes. This bipole network also forms an effectively continuous bipole field along the outer surface of the device. Adjacent bipole pairs are positioned close to each other.

In some variation all of the cathodes forming a bipole network are electrically connected to each other and all of the anodes forming a bipole network are electrically connected. For example, the anodes of the bipole network may all be formed from a single anodal connector, and all of the cathodes of a bipole network may be formed from a single cathodal connector. Alternatively, all of the cathodes of the bipole network may be formed separately and connected distally on the device. For example, all of the cathodes may be wired to a single connector that connects to a power source or controller configured to energize the bipole network in a particular region.

A device may include multiple bipole networks. For example, different regions on the surface of the device may include different bipole networks (e.g., each region may have its own bipole network). The bipole networks in different regions may be non-overlapping, and may form effectively non-overlapping continuous bipole fields. "Effectively non-overlapping bipole fields" means that the broadcast fields of two or more bipole networks do not substantially overlap. For example, the component of a broadcast field (e.g., intensity) due to a second bipole network is less than 15% (or 10%, or 8% or 5% or 1%) of the component due to a first bipole network at any position near the first bipole network, particularly at the excitation ranges described herein.

A device for determining if a nerve is nearby may also include a controller for controlling the application of energy to the bipoles. In particular, the application of energy to the bipoles may be coordinated as described in the methods sections below, so that the activation of a nerve can be correlated to a particular region of the surface of the device.

In some variations, the bipole or bipole networks are movable with respect to the outer surface of the device. Moving the bipole (e.g., rotating it a around the outer surface) may allow a bipole field (a tight or narrow broadcast field) to be correlated with different regions of the device. This is also described in greater detail below.

Nerve Localization Devices

FIG. 2A, illustrates the distal portion of one embodiment of a device capable of determining if a nerve is nearby. This exemplary device 80 is shown in partial cross-section. For clarity, FIG. 2A does not show the bipoles, thus showing more clearly the structure of probe device 80. In this example, the device 80 includes a rigid cannula 82 (or tube or needle) and a curved, flexible guide 84 that can slide through cannula 82. The guide 84 may include a Nitinol core 86 (or inner tube) having a central lumen 88 and an atraumatic, rounded tip 87 and may also include a sheath 89 (or coating or cover) disposed over at least part of Nitinol core 86. The sheath 89 may comprise, in one embodiment, a polymeric material such as PEBAX, PEEK or the like, or any other suitable material, and may form an outer surface having different regions. Core 86 may be made of Nitinol or may alternatively be made of one or more other substances, such as spring stainless steel or other metals. Lumen 88, in some embodiments, may be used to pass a guidewire.

FIG. 2B is a perspective view of a portion of the probe 80 of FIG. 2A, in which two electrically conductive members 90 are visible. One member may be a cathodal conductor and one member may be an anodal conductor. A probe may include as many electrode pairs as desired, such as eight, sixteen, thirty-two, etc. In this example, the probe may have a preformed, curved shape and may be made of at least one flexible, shape memory material, such as Nitinol. In this way, guide 84 may be passed through cannula 82 in a relatively straight configuration and may resume its preformed curved shape upon exiting a distal opening in cannula 82. This curved shape may facilitate passage of guide 74 around a curved anatomical surface, such as through an intervertebral foramen of a spine.

The exemplary device shown in FIGS. 2A-2D may include at least one bipole network, including a plurality of anodes and cathodes. In this example, anodes of a single bipole network are all formed from the same anodal conductor, and the cathodes of the same anodal conductor are all formed from the same cathodal conductor. FIG. 2C illustrates this. In FIG. 2C a section of probe sheath 89, including the outer surface region, is shown in more detail. In one embodiment, sheath 89, which fits directly over at least a portion of Nitinol core 86 (FIG. 2A), includes multiple, longitudinal lumen 92, each of which may contain an electrical conductor 94 forming a plurality of electrodes (e.g., anodes or cathodes). In some embodiments, conductors 94 may be slideably disposed inside lumen 92, while in other embodiments they may be fixedly contained therein. Openings into the sheath 89 form the plurality of cathodes and anodes. The openings may be pores, holes, ports, slits, grooves or the like. Each aperture 96 may extend from an outer surface of sheath 89 to one of conductor lumen 92. As such, apertures 96 may help direct current along paths from one electrical conductor (e.g., cathodal conductor) to the other electrical conductor (e.g., anodal conductor) forming the plurality of bipolar electrode pairs. In some embodiments the conductor 94 may partially extend through and above of the aperture 96 surface. This may be achieved by a conductor 94 that has several bends enabling the apex of the bend to protrude through the aperture 96. Alternatively, the conductor 94 may have sections of its length near the aperture 96 that have a larger diameter than other sections of conductor 94. In a given embodiment, any number of lumen 92, electrical conductors 94 and apertures 96 forming anodes or cathodes may be used. In some embodiments, apertures 96 may extend along a desired length of sheath 89 to approximate, for example, a length of an area to be treated by a device or procedure.

FIG. 2D shows a section of sheath 89 is shown in cross section, showing an electrical conductor 94 comprising (i.e., a cathodal conductor) and a current directing aperture 96 (i.e., forming a cathode of a bipole). In some embodiments, some or all of apertures 96 may be filled with a conductive material 97, such as a conductive gel, solid, matrix or the like. Conductive material 97 may serve the dual purpose of helping conduct electric current along a path and preventing non-conductive substances from clogging apertures 96.

The example shown in FIGS. 2C-2D has four circumferential regions spaced around the circumference of the outer surface of the sheath region of the device. In this example, each region includes a bipole network formed by an anodal and cathodal conductor that are positioned in parallel. Thus, the bipole network (similar to that shown in FIGS. 1D and 1E) extends along the length of each surface region of the device, and may form an effectively continuous bipolar field along the outer surface.

Figure 3:
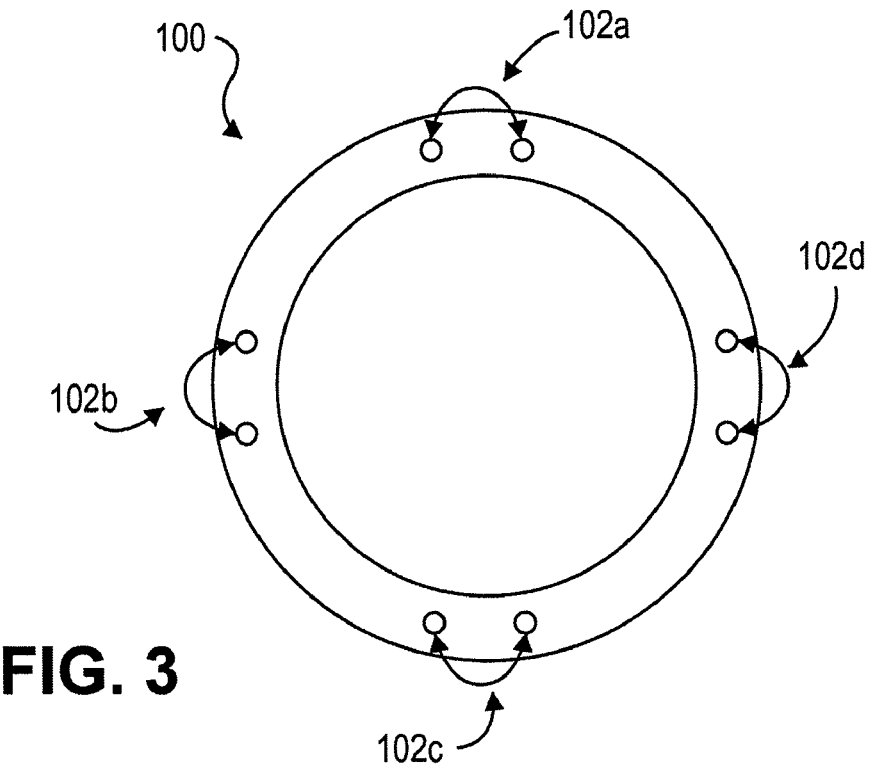
FIG. 3 is cross-section through a device showing four circumferential regions.

FIG. 3 illustrates a similar arrangement having four regions which each include electrical connectors within the elongate body that may form the bipole network. For example, in FIG. 3, four pairs 102 of anodal and cathodal conductors are shown. The conductors of each pair 102 are close enough together that electric current is transmitted only between electrodes formed by each pair 102a and not, for example, between electrode pairs formed by other anodal or cathodal conductors 102b, 102c, 102d. In some embodiments, the anodal conductor and the cathodal conductor may be "switched" to change the direction that current is passed between electrodes formed by the two conductors. For example, one conductor of each pair 102 may be designated as the transmission conductor (cathode), and the other electrode of the pair 102 may be designated as the return electrode (anode). When one of the conductors forming the anode or cathode is set to ground, this ground may be isolated from the ground (e.g., an anodal conductor) in other regions of the device, which may help isolate the current to the bipolar network in a single region of the device. In various embodiments, electrodes forming the bipole pair may be spaced at any suitable distance apart by spacing the electrical conductors forming the electrodes of the bipole pair. For example, electrodes of each pair may be spaced about 0.1 mm to about 2 mm apart, or about 0.25 mm to about 1.5 mm apart, or about 0.5 mm to about 1.0 mm apart.

Figure 4:
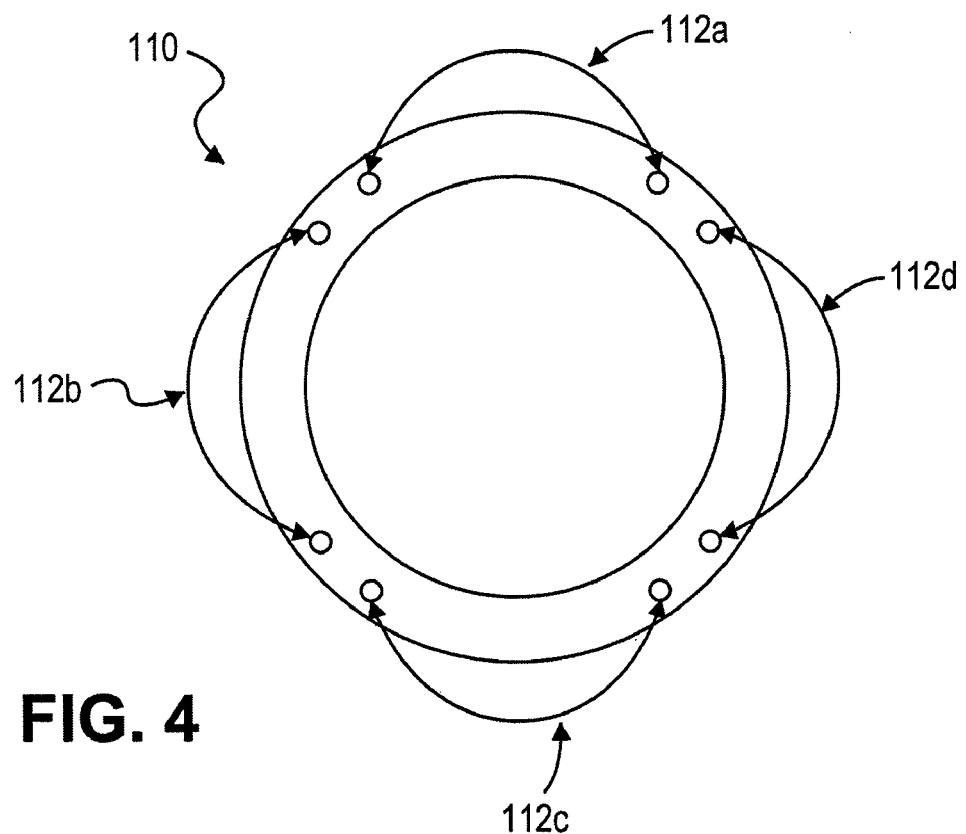
FIG. 4 is another cross-section through a device having four circumferential regions.

FIG. 4 shows another example of a cross-section through a device having pairs 112 of electrical conductors that may form a network of bipole pairs on the surface of the device. In this example, the anodal and cathodal conductors are spaced farther apart. Farther spaced electrode pairs 112 may allow current to pass farther into tissue but may also risk dispersing the current farther and potentially being less accurate. Depending on the specific use and desired characteristics of the device (e.g., sheath 110), the bipole pairs formed may be spaced at any of a number of suitable distances from one another.

Alternative arrangements of bipole pairs formed from an anodal and cathodal conductor are shown in FIGS. 5A-7B. For example, FIG. 5A is a side-view of a pair of bipole pairs that are formed by apertures 122, 124 in the body of the device (sheath 120) which expose portions of the cathodal electrical conductor 126 and portions of the anodal conductor 128. Apertures forming the cathodes 122 and anodes 124 are disposed along a length of sheath 120 separated by a distance d. As shown in FIG. 5B, the electrical conductors (i.e., cathodal conductor 126 and anodal conductor 128) are embedded in the elongate body and are spaced apart from each other about a circumferential distance s. In one embodiment, the distance d may be greater than the distance s, so that current is more likely to travel circumferentially between positive and negative electrodes, rather than longitudinally along sheath 120. As can be appreciated from FIGS. 6A and 7A, current may be directed along any of a number of different paths in different embodiments of elongate body (sheath 120), by changing the separation distances of apertures 122, 124 providing access to the electrical conductors 126, 128.

For example, in FIGS. 6A and 6B, the cathodal and anodal conductors are positioned in immediately above and below one another, and apertures forming the anodes and cathodes of bipole pairs may be spaced at different distances along the body of the device 130, such that current is more likely to travel between two closer spaced apertures (distance d') than between two farther spaced apertures (distance d).

In FIGS. 7A and 7B, current may be directed along a distance d between apertures forming anodes and cathodes of bipole pairs that are spaced more closely together than the anodal and cathodal conductors of other bipole pairs. As mentioned above, in various embodiments of these nerve localization devices, any combination of anodal or cathodal conductors, apertures forming the anode and cathode pairs, and/or other current direction path features may be included.

FIG. 8 shows a portion of a nerve localization device 150. This nerve localization device variant includes a sheath 152 having multiple current directing apertures 154 disposed over a cathodal conductor and an anodal conductor, forming bipole pairs along the outer surface of the device. As shown, current may be driven along multiple paths between pairs of apertures 154a, 154b, 154c, 154d. Multiple individual currents I1, I2, I3 and I4 add up to the total current IT transmitted between the anodal and cathodal conductor. In various embodiments, the bipole pairs formed 154 may be disposed along any desired length of probe 150. Any number of bipole pairs may be included. As mentioned above, in some variations the cathodes and/or anodes formed in a single region of the device may be formed from multiple (including individual) anodal/cathodal conductors (e.g., wires).

Figure 9:
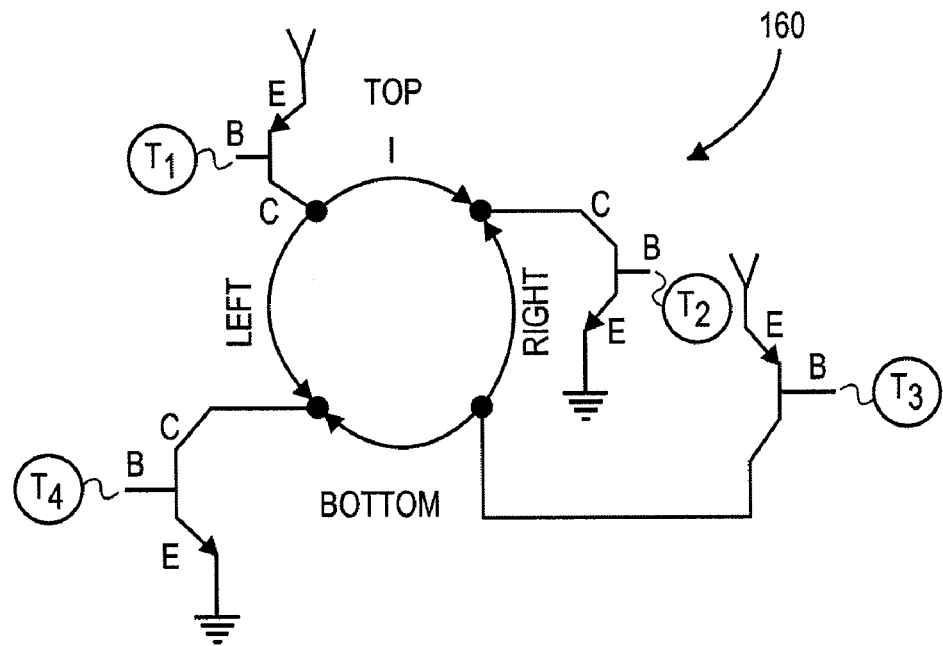
FIG. 9 is a circuit diagram of one variation of a portion of a nerve localization device.

FIG. 9 is a circuit diagram 160 for a nerve localization device having two bipole pairs (e.g., eight electrical conductors). In this simple form, electric current may be driven between the electrical conductors along a top, bottom, left and right side, separately. Each of these side forms a different region of the device.

Figure 10:
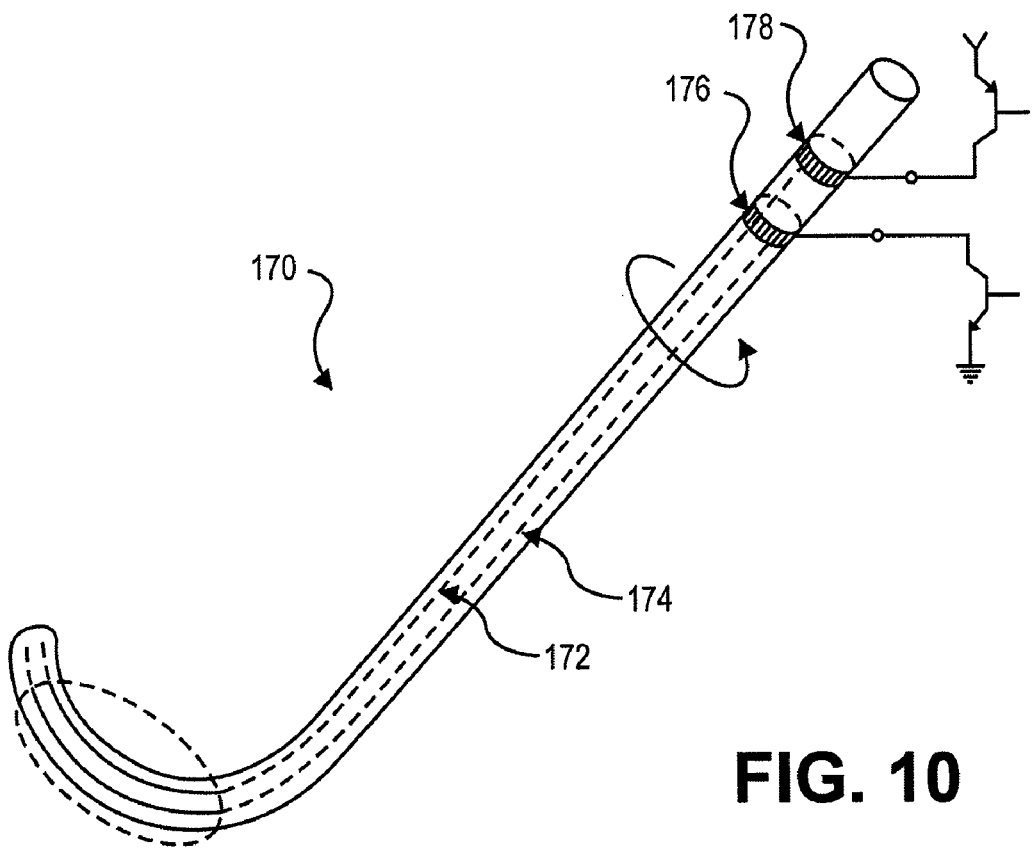
FIG. 10 is a perspective view of a portion of a nerve localization device having two electrodes with rotating brushes.

Another example of a nerve localization device is shown in FIG. 10. In FIG. 10, the nerve localization device includes two electrical conductors 172, 174 forming at least one bipole pair (not shown) and two rotating brushes 176, 178. Such an embodiment may allow different sides, such as top, bottom, left and/or right sides, to be stimulated with only two electrodes 172, 174, rather than multiple electrode pairs in different sections.

The elongate bodies forming part of the nerve localization devices described above may be used with any appropriate controller and/or stimulator configured to energize the bipole pairs. Thus, any of these devices may be used as part of a system including a controller and/or stimulator. In some variations, the elongate body may also be referred to as a probe. Examples of elongate bodies, including elongate bodies having different regions which may each contain one or more bipole pairs, are shown in FIGS. 11A-13D.

FIG. 11A is a simplified diagram of one variation of a device 10. This device 10 may be used to perform one or more medical procedures when orientation of the device with respect to an adjacent nerve is desired. Similar to the device shown in FIG. 2A above, this variation 10 includes a cannula 20 and a probe 30. The device 30 includes a tip 40, a top section 32, and a bottom section 34. The device 30 may include multiple bipole pairs 76, 78 or bipole networks consisting of multiple bipole pairs. A first bipole pair or bipole network 76 may be located on a first section 32 and a second bipole pair 78 may be located on a second section 34. In one variation the bipole network or pair 76 may be energized to determine whether a nerve is located near or adjacent to the first or top section 32. The second bipole network or pair 78 may be energized to determine whether a nerve is located near or adjacent to the second or bottom section 34. The first bipole network or pair 76 and the second bipole network or pair 78 may be alternatively energized to independently determine whether a nerve is located near or adjacent to the first section 32 and/or the second section 34.

In some variations a bipole pair or network 76, 78 is typically energized with one or more electrical signal(s). The device may monitor the electrical signal applied to the bipole network (or pair) 76, 78, and may monitor the characteristics of the electrical signal and determine whether tissue is near or adjacent the bipole(s) 76, 78 as a function of the monitored electrical signal characteristics. The electrical signal characteristics may include amplitude, phase, impedance, capacitance, and inductance over time or frequency.

After an electrical signal is applied to the bipole network or pair 76, 78, an output may be detected. In some variations the nerve localization device includes a sensor or sensors for monitoring the nerve response. For example, the device may monitor one or more sensors anatomically coupled to nerve or afferent tissue enervated by the nerve whose condition is modified by the signal(s) applied to the bipolar network or pair 76, 78. For example, the device may monitor one or more sensors innervated by the nerve tissue such as limb muscles.

The nerve localization devices and systems described herein may include one or more indicators or outputs 22, 24. The detectors may provide a user-identifiable signal to indicate the location of the nerve or the status of the system. For example, the nerve localization devices may include one or more light emitting diodes (LEDs), buzzers (or other sound output), a video display, or the like. An LED may be illuminated based on signals generated by, received by, or generated in response to the energized bipole(s) 76 or 78 as discussed above. In some variations the system or devices create a vibration or sound that a user manipulating the device 20 may feel or hear. The intensity of the output may vary as a function of detected signal.

As shown in FIG. 11B, a nerve localization device may include a pair of electrical conductors 36 (anodal conductor and cathodal conductor) which form one or more bipole pairs. The anode or a cathode of the bipole pair(s) 76, 78 may be formed as described above via an opening 37 filled with a conductive material 38, such as a conductive gel, solid, matrix, or other conductive material. An example of this is shown in FIG. 11C. Alternatively, the bipole pair 36 and the conductive material 38 could be formed from the same conductive elastic or semi-elastic material. The elongate body of the device 30 may include a bipole network comprising bipole pairs that are configured in a coil or zig-zag pattern along the length of the probe. This arrangement may help ensure continuous conduction during flexion of the probe 30. In another variation, the anodal and/or cathodal conductors are formed of conductive ink (e.g., loaded in an elastomeric matrix) may be deposited on the outside of the probe. The conductive ink could be insulated with the exception of discrete points forming the anode or cathode of the bipole pair. In another embodiment a thin flex circuit could be wrapped around probe to construct the bipoles.

FIG. 11D is a partial, simplified diagram of a rongeur jaw 680 configured as a nerve localization device. In this variation the rongeur jaw forms the elongate body of the device on which at least one bipole pair is located. The rongeur jaw 680 may include a lower jaw 682 and an upper jaw 684. The lower jaw 682 may have a tip 688 and a bipolar network or pair 78 on an inner surface. The upper jaw 684 may have a tip 686 and a bipolar network or pair 76 on an inner surface. In one variation, the first bipolar network or pair 78 may be energized to determine whether a nerve is located near or adjacent to the first or bottom jaw 682. The second bipole network or pair 76 may be energized to determine whether a nerve is located near or adjacent to the second or top jaw 684. The first bipolar network or pair 76 and the second bipolar network or pair 78 may be alternatively energized to independently determine whether a nerve is located near or adjacent to the first, bottom jaw 682 and/or the second, upper jaw 684.

In operation, a user may employ such a device to ensure that a nerve is located between the lower jaw 682 and upper jaw 684 or that a nerve is not located between the lower jaw 682 and upper jaw 684. A user may then engage the rongeur jaws 680 to excise tissue located between the jaws 682, 684. A user may continue to energize or alternately energize the bipole networks or pairs 76, 78 on either jaw while excising tissue.

Figure 12A:
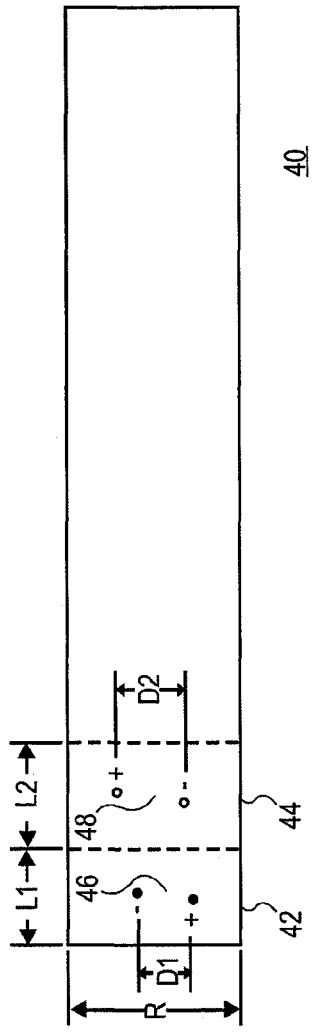
FIGS. 12A-12C illustrate elongate bodies having a plurality of regions each including at least one bipole pair.
Figure 12B:
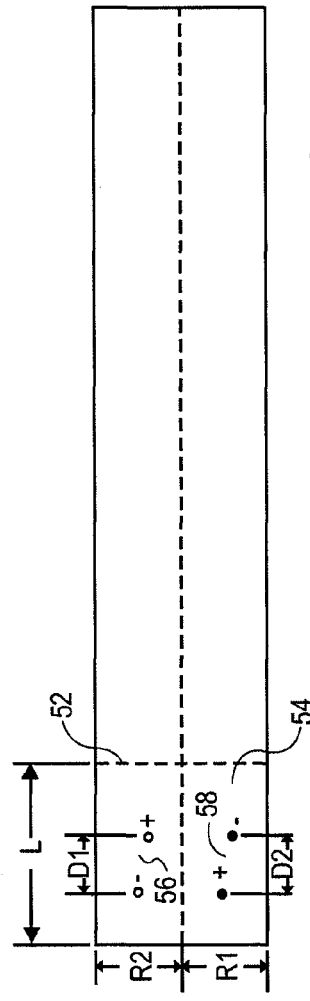
Figure 12C:
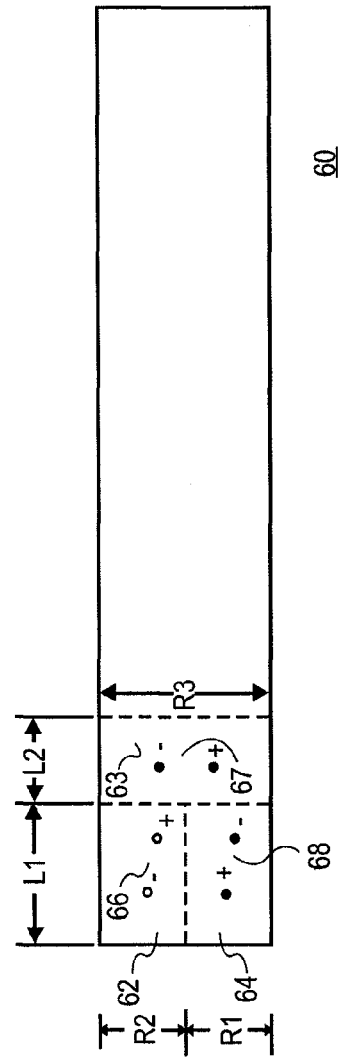

FIGS. 12A-12C are examples of elongate bodies having regions which include at least one bipole pair, and may include a bipole network. Each elongate body in FIGS. 12A-12C (40, 50, and 60, respectively) may be part of a device or system capable of determining if a nerve is nearby the device, and may be configured as part of surgical instrument such as a rongeur 680, or other instrument. The configuration 40 shown in FIG. 12A includes two longitudinal regions 42, 44 at the distal end. The distal section 42 has a longitudinal length L1 and a width R, which may also be referred to as a radial length. The more proximal section 44 has a longitudinal length L2 and a width of R. Each region 42, 44 includes at least one bipole pair 46, 48. A bipole pair 46, 48 typically includes at least one anode (−) and cathode (+) that can be excited to create a restricted current pathway between the anode and cathode 46, 48.

The distance between the anode and cathode pair of may be less than the distance between any of the electrodes forming part of a bipole pair in an adjacent region of the elongate body. For example, the electrodes forming the bipole pair (or bipole network) in the first region 42 are closer to each other than to either the anode or the cathode in the adjacent region 44. Likewise, the distance between the anode and cathode pair in the second region 44 is less than the distance between the anode and the cathode of the first region. For example, the distance between the anode and cathode forming bipole pairs in the first region 42 is labeled D1 and the distance between the anode and cathode in the bipole pair in the second region is labeled D2. D1 may be less than or equal to L1 and R and D2 may be less than or equal to L2 and R. Any appropriate spacing (D1 or D2) may be used between the anodes and cathodes forming the bipole pairs. For example, D1 and D2 may be about 0.25 mm to 2.0 mm apart. In one variation D1 and/or D2 are about 0.50 mm. When a bipole or bipole network in a region 46, 48, is energized, current may flow between the anode and cathode along a conductive pathway substantially only within its respective sections 42, 44. This current flow (and/or the related magnetic field) may be referred to as the 'broadcast field of the bipole pair or bipolar network. A device including regions having tight bipoles or bipole networks 40 may be employed to determine whether a nerve is closer to the first region 42 or the second 44, as described above. The bipole pairs (or bipole networks) in each region may be alternatively energized and an external sensor(s) can be used to monitor and/or determine whether a nerve is closer to the first region 42 or second region 44.

The arrangement of the bipole pairs or bipole network may help determine the sensitivity of the device. For example, D1 may be less than D2, resulting in the bipole pair in the first region having a smaller broadcast field (and a shorter conductive pathway) than the bipole pair 48 in the second region. This may allow detection of a nerve located further from second region than the first region, assuming a nearly equivalent energy is applied to the bipole pairs (or networks) within each region. Of course, the energy applied may be varied between different regions.

FIG. 12B shows an example of an elongate member 50 having two regions 52, 54 separated along the longitudinal (or circumferential if the member is rounded) axis of the member 50. Each region 52, 54 may include one or more a bipole pairs 56, 58. For example, each region may include a bipole network formed of multiple bipole pairs. The individual bipole pairs may share anodes and cathodes, as described above. In this example, the width of the first region is the circumferential or linear distance, R1, and the length is the distance L. The width of the second region is R2 and the length is L. The bipole pairs 56, 58 in each region may be longitudinally oriented, radially oriented, or some combination. For example, a bipole network may have anodes and cathodes arranged in a linear pattern (e.g., extending longitudinally) or a zigzag pattern (also extending generally lineally). Other arrangements are possible.

FIG. 12C shows another variation of an elongate member having three regions, two arranged longitudinally 62, 64, and one more proximally 63, adjacent to the two distal longitudinal (or circumferential) regions. Each region 62, 63, 64 may include one or more bipoles 66, 67, 68 or bipole networks. The spacing between the electrodes forming the bipoles of a bipole pair or network in one of the regions may be less than the spacing to electrodes outside of the region. This may prevent current from passing from an electrode (e.g., anode, cathode) in one region and electrodes in another region. In some variations the controller or device is configured so that the anodes and/or cathodes are electrically isolated (e.g., do not share a common ground) and may be configured to electrically float when not being energized.

Figure 13B:
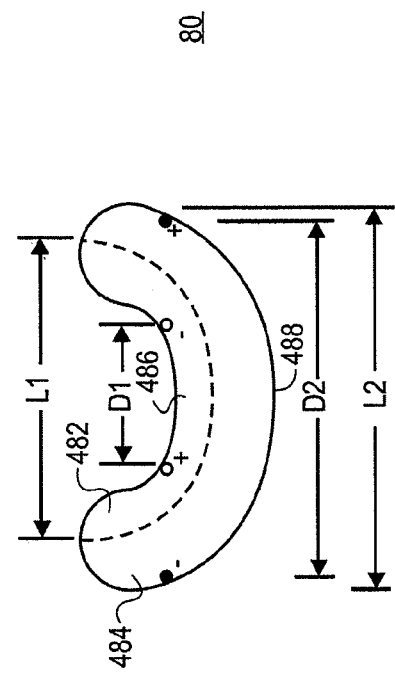
FIGS. 13A-13D show partial cross-sections through various devices having elongate bodies including multiple regions.
Figure 13D:
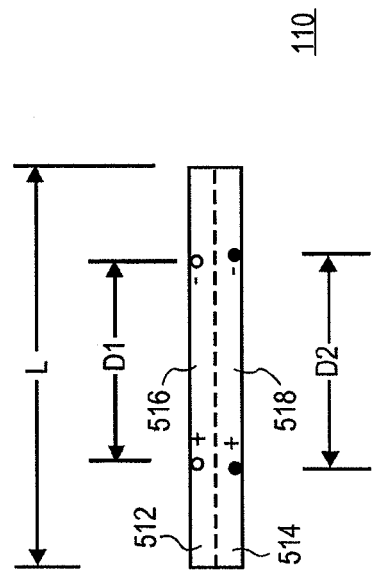
Figure 13A:
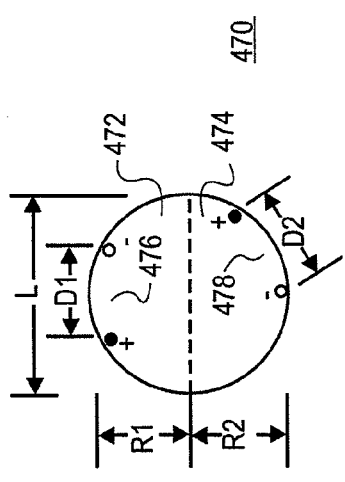

FIGS. 13A-13D show partial cross-sections through elongate members 470, 480, 490, 510 which may be used as part of a device for determining if a nerve is nearby. Each region includes multiple (e.g., two or more) regions that each include one or more bipole pairs (e.g., bipole networks). These examples each have a different cross-sectional shape, and have circumferential regions that are oriented differently around the perimeter of the elongate member. For example, FIG. 13A shows a portion of a device having an outer surface that includes two regions or sections 472, 474 that are circumferentially distributed. Each region 472, 474 includes one or more bipoles 476, 478, having at least one anode (−) and one cathode (+) that can be powered so that current flows between the anode and cathode, resulting in a broadcast field. In this embodiment, the distances between the anode and cathode pairs forming the bipoles in each region are less than the distance between the anode of one region and the cathode of the other region. Region 472 may have a radial length R1 and circumferential span of L (e.g., a width of R1*pi); the longitudinal distance or length is not apparent from this cross-section, but may extend for some distance. In this example, a bipole pair in the first region may have an anode and cathode 476 that are separated by a distance (approximately D1) that is less than half the length of the first circumferential region, and the spacing of the tight bipole pair (approximately D2) in the second region may be less than half the length of the second circumferential region. In one variation, D1 and/or D2 may be about 0.50 mm. In some variations the spacing between the bipole pairs in different regions (and within the same region for bipole networks) is approximately the same.

The configuration 480 shown in FIG. 13B may also include two circumferential regions 482, 484 on the distal end of the elongate member. Each region 482, 484 may include a bipole pair or network 86, 88, as described above. In this embodiment, the distances between the anode and cathode pairs of either of region 486 and 488 is less than the distance between the anode of one region and the cathode of the other region.

Figure 13C:
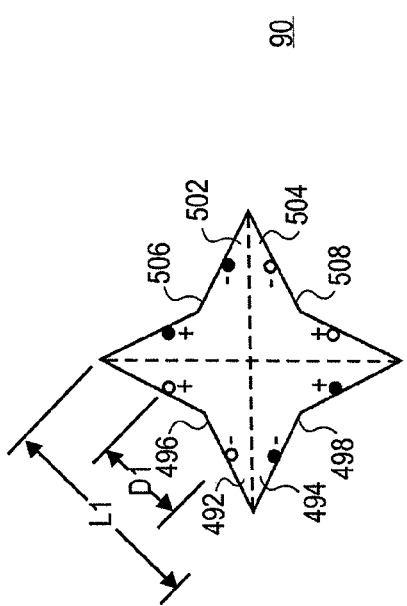

The configuration 490 shown in FIG. 13C includes four radial regions 492, 494, 502, 504 which may also each have one or more bipole 496, 498, 506, 508. FIG. 13D has two circumferential regions 512, 514. Each radial region 512, 514 includes at least one bipole pair 516, 518.

FIGS. 14A-14C are partial diagrams of a portion of a device capable of determining if a nerve is nearby. The device includes an elongate body (shown in cross-section) having to regions with at least one bipole pair in each region. The device is deployed in tissue 522, 524. The device 470 shown in FIG. 14A includes two radially separated regions 472, 474, similar to the device shown in FIG. 13A. Each region 472, 474 has a bipole network or at least one bipole pair 476, 478 having an anode (−) and cathode (+). The device may determine whether the module 476 is near or adjacent a nerve (e.g., in the tissue 522 or 524) as a function of signals generated in response to one or more energized bipole pairs in the regions, as described above. When a bipole pair or network 476 is energized, the conductive pathway (or bipole field) typically does not extend substantially into the tissue 524, 522.

The first region 472 may have a radial length R1 and longitudinal length, L, and the second region 474 may have a radial length R2 and longitudinal length, L. An anode and a cathode forming at least one bipole pair within the first region 472 may be separated by a distance, D1, and an anode and cathode in the second region may be separated by a distance D2. In some variations the energy applied to a bipole pair or network does not project very far into the tissue. This may be a function of the configuration of the bipole pair (e.g., the size and spacing) and the energy applied. For example, the energy projecting in to the tissue from a bipole pair in the first region 472 may not extend substantially further than a distance of T1, so that it would not provoke a response from a neuron located further than T1 from the electrodes. Similarly, the energy projecting into the tissue from a bipole pair (or the bipole network) in the second region 474 may not extend substantially further than a distance of T2 from the electrodes. The electrodes of the bipole pair or network in the first region 472 may be are separated by a distance, D1 that is less than or equal to R1, T1, and L, and the bipole pair or network in the second region 474 may be separated by a distance D2 that is less than or equal to R2, T2, and L. For example, D1 and D2 may be about 0.25 mm to 2.0 mm apart (e.g., 0.50 mm). The energy applied to the bipole pair or network may be limited to limit the projection of energy into the tissue. For example, the current between the bipole pairs may be between about 0.1 mA to 10 mA.

The device may be used to determine if a nerve is near one or more regions of the outer surface of the device, and/or which region the nerve is closest to. For example, a first electrical signal may be applied to the bipole pair/network in the first region 472 for a first predetermined time interval, and a response (or lack of response) determined. A response may be determined by using one or more sensors, it may be determined by observing the subject (e.g., for muscle twitch), or the like. Thereafter a second electrical signal may be applied to the bipole pair/network in the second region 474 for a second predetermined time interval, and a response (or lack of a response) determined. The first predetermined time interval and the second predetermined time interval may not substantially overlap, allowing temporal distinction between the responses to different regions. The device may include more than two regions, and the bipole network may be of any appropriate size or length.

Based on the monitored response generated after the application of energy during the predetermined time intervals, it may be determined if a nerve is nearby one or the regions of the device, or which region is closest. For example, if application of energy to the bipole pairs/networks in both regions results in a response, the magnitude of the response may be used to determine which region is closest. The durations of the predetermined time intervals may be the same, or they may be different. For example, the duration of the firs predetermined time interval may be longer than the duration of the second predetermined time interval. The average magnitude of the electrical signals applied may be the same, or they may be different. For example, the magnitude of the signal applied to the bipole pair/network in the first region may be greater than the average magnitude of the signal applied to the second region.

The device 450 shown in FIGS. 14A and 14B includes two longitudinally separated sections 452, 454. Each section 452, 454 has a bipole pair or bipole network 456, 458 that has at least one anode (−) and one cathode (+).

The device 440 shown in FIG. 14C includes two longitudinally separated regions 442, 444, each including a bipole pair or network 446, 448 including at least one anode (−) and one cathode (+). When the bipole pair or network in a region is energized, the device may be used to determine if a nerve is nearby based on the generated response to the energized bipole pair/network.

FIG. 14D shows a cross-section through a region of an elongate body of a device having four regions which each include bipole pairs or networks. The electrodes forming the bipole pairs or networks are connected to an electrically conductive element so that the anode(s) and cathode(s) in a particularly region are all in electrical communication. For example, as illustrated in FIG. 14D, four cathodal conductors 644, 664, 632, 652 pass through the body of the device and electrically connect to electrode regions (not visible in FIG. 14D) on the surface of the device. Similarly, four anodal conductors 642, 662, 634, 654 pass through the body of the device and electrically connect to electrode regions (not visible in FIG. 14D) on the surface. This forms bipole pairs 640, 660, 630, 650. When the cathodal and/or anodal conductors form multiple electrode regions (electrodes) in each region, they may form a bipole network 640, 660, 630, 650.

Figure 14E:
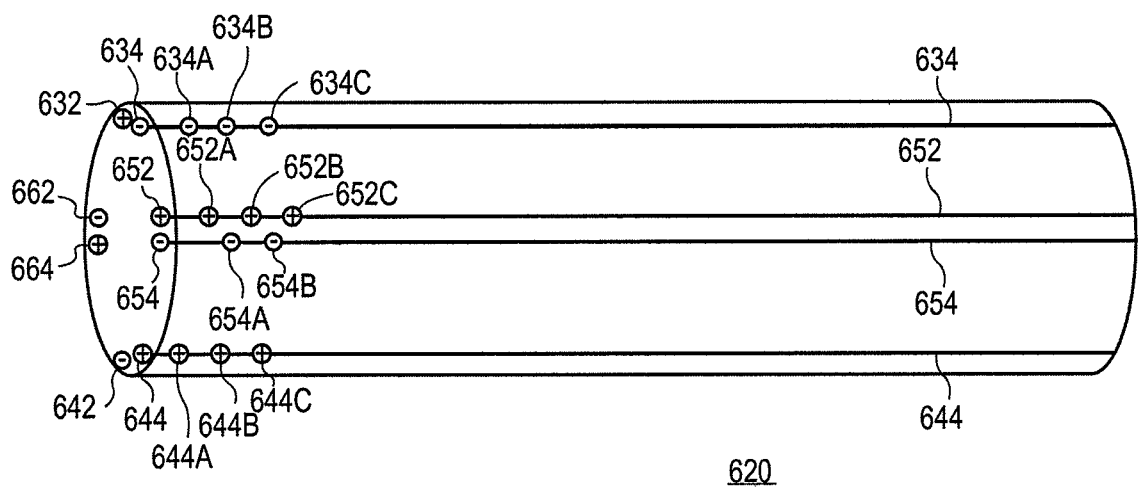

FIG. 14E is a partial isometric diagram of a device shown in FIG. 14D, in which each region includes a bipole network formed along the lengths of the device. Each bipole network includes anodes formed from a single anodal conductor and cathodes formed from a single cathodal conductor. FIG. 14F is an exemplary illustration of an anode or cathode 632. The anode may have any appropriate shape (e.g., round, oval, square, rectangular, etc.), and any appropriate surface area (e.g., less than 10 mm$^2$, less than 5 mm$^2$, less than 3 mm$^2$, less than 2 mm$^2$, less than 1 mm$^2$). For example, in some variations, the height of the anode or cathode (e.g., Y1) may be about 0.25 mm to 0.75 mm, and the width of the anode or cathode (e.g., X1) is about 3× the height (e.g., X1=3*Y1). As mentioned previously, the electrode may be formed of a conductive material (e.g., metal, polymer, etc.), and may be formed by forming a passage into the body of the elongate member until contacting the conductive member, then filling the passage with an electrically conductive material.

The conductive element may be a conductive wire, gel, liquid, etc. that may communicate energy to the anodes or cathodes.

The elongate body may be any appropriate dimension, and may be typically fairly small in cross-sectional area, to minimize the damage to tissue. For example, the outer diameter of elongate member may be about 1.5 mm to 5 mm (e.g., about 2 mm).

Figure 15:
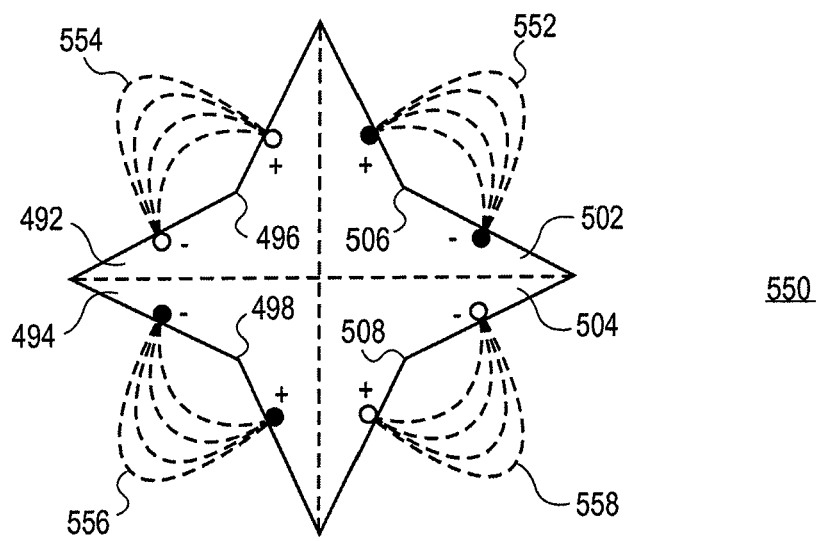
FIG. 15 is a cross-section through another variation of a device.

FIG. 15 illustrates conductive pathways 550 of one example of a device 490 (similar to the variation shown in FIG. 13C) that includes four radial regions 492, 494, 502, 504 near the distal region of the elongate body. Each bipole pair or network 496, 498, 506, 508 includes at least one anode (−) and cathode (+) that, when energized, creates a limited conductive pathway between the respective anode(s) and cathode (s) of the bipole or bipole network 496, 498, 506, 508. For example, the current pathways 554, 556, 552, and 558 between the bipoles may broadcast energy about 3 to 5 times the distance between the respective cathodes and anodes forming the bipole(s). Thus, the current pathways 554, 556, 558, 552 may be substantially confined to the respective regions 492, 494, 502, 504 of the elongate body forming the bipole or bipole network.

In operation, each bipole network is stimulated separately for a predetermined time. For example, one bipole network 496, 498, 506, or 508 may be energized with a first signal for a predetermined first time interval. Thereafter, another bipole network 496, 498, 506, or 508 may be energized with a second signal for a predetermined second time interval. Different energy levels may be applied, for example, as a function of the tissue 522, 524 that a user is attempting to locate or identify.

FIGS. 16A-16D are diagrams of electrical signal waveforms 580, 590, 210, 220, 230, 240 that may be applied to one or more bipole pairs (or bipole networks). Exemplary signal waveforms include square-wave pulses 582, 584, 586. Each pulse 582, 584, 586 may a have a similar magnitude and envelope. The square-wave pulses may be idealized (e.g., with square edges, etc.), or rounded (as shown in FIGS. 16A-16D). The waveforms may be used to energize the bipole network periodically P1 for a predetermined interval T1 where each pulse 582, 584, 586 has an amplitude A1. For example, A1 maybe about 0.1 milliamperes (mA) to 10 mA, the pulse width T1 may be about 100 microseconds (μs) to 500 μs and the period P1 may from 100 ms to 500 ms. For example, A1 may be about 0.5 milliamperes (mA) to 5 mA, the pulse width T1 may be about 200 microsecond (μs) and the period P1 may about 250 ms as a function of the energy required to depolarize neutral tissue. The applied energy may also be expressed as a voltage.

FIG. 16B illustrates another variation, in which the applied signal waveform 590 includes square-wave pulses 592, 594, 596 that have an increasing magnitude but similar pulse width T1. The waveform 590 may be used to energize a bipole network periodically P1 for a predetermined interval T1 where pulses 592, 594, 596 have increasing or ramping amplitudes A1, A2, A3. The waveform 590 may continue to increase pulse amplitudes in order to identify a nerve (up to some predetermined limit). For example, stimulation of one or more bipole pairs may cycle a ramping stimulation. In one example, A1, A2, and A3 are about 1 milliamps (mA) to 5 mA where A3>A2>A1, the pulse width T1 maybe about 100 microsecond (μs) to 500 μs and the period P1 may from 100 ms to 500 ms. For example, the pulse width T1 may be about 200 microseconds (μs) and the period P1 may about 250 ms.

In FIG. 16C the signals applied to energize different regions of the device are different. For example, a first waveform 210 may be applied to a first bipole network of a device, and a second waveform 220 may be applied to energize a second bipole network of the device. In this example, the signals are interleaved. The signal waveform 210 includes several square-wave pulses 212, 214, and 216 and the signal waveform 220 includes several square-wave pulses 222, 224, and 226. Each pulse 212, 214, 216, 222, 224, 226 may a have a similar magnitude and envelope. The waveform 210 may be used to energize the first bipole network periodically P1 for a predetermined interval T1, where each pulse 212, 214, 216 has an amplitude A1. The second waveform 220 may be used to energize a second bipole network periodically P2 for a predetermined interval T2 where each pulse 222, 224, 226 has an amplitude B1. In some variations, the pulse width T1, T2 is about 100 microseconds (μs) to 500 μs, and the period P1, P2 is from 100 ms to 500 ms. For example, A1, A2 may be about 0.5 milliamperes (mA) to 5 mA, the pulse width T1, T2 may be about 200 microsecond (μs) and the period P1, P2 may about 250 ms. The pulses 212, 214, 216 do not substantially overlap the pulses 222, 224, 226. In some variations, T1>T2 and P2 is an integer multiple of P1.

FIG. 16D is another example, in which different regions of the device are energized with pulses having increasing amplitudes. In this example, an amplitude increasing or ramping pulse waveform 230 may be applied to a first bipole network, and a second amplitude increasing or ramping pulse waveform 240 may be applied to a second bipole network. The signal waveform 230 includes several amplitude increasing or ramping square-wave pulses 232, 234, and 236 and the signal waveform 240 includes several amplitude increasing or ramping square-wave pulses 242, 244, and 246. In variations having more than two regions, each region may be stimulated separately, so that the time period between stimulations (P1-T1) may be larger than illustrated here. Methods may also include changing the stimulation applied, or scaling it based on a response, as described in more detail below.

FIG. 17A is illustrates a schematic of a subject 310 in which the device for determining if a nerve is nearby is being used. In this illustration 300, a tissue localization device 10 is used as part of a system including sensors 322, 324. In this system, the device 10 may energize one or more bipole pairs or bipole networks to depolarize neutral tissue that is near a region of the device including the bipole pair or network. A sensor 322 may be placed on, near, or within muscle that may be innervated when neutral tissue is depolarized by a nearby energized bipolar or optical module. The sensor 322 may be innervately coupled to nerve tissue via a neural pathway 316 and sensor 324 may be innervately coupled to nerve tissue via a neural pathway 314. For example, the device may be used as part of a spinal procedure and the sensors 322 may detect an Electromyography (EMG) evoked potentials communicated in part by a patient's cauda equina along the pathways 314, 316.

FIGS. 17B-11D are simplified diagrams of sensors 330, 340, 350 that may be employed according to various embodiments. For example, a sensor 330 may include a multiple axis accelerometer employed on or near muscle, particularly muscle innervated by neurons within the region of tissue being operated on. The accelerometer may be a low-g triaxial accelerometer. The accelerometer 330 may detect differential capacitance where acceleration may cause displacement of the silicon structure of the accelerometer and change its capacitance. The sensor 340 may include a strain gauge that also may be applied on or near muscle innervated by neurons within the region begin operated on. The strain gauge may a multiple planar strain gauge where the gauge's resistance or capacitance varies as a function of gauge flex forces in multiple directions. The sensor 350 may include an EMG probe. The EMG probe may include a needle to be inserted near or within muscle innervated by a neuron or neurons within the region being operated on. For example, a sensor may determine a positive response when detecting an EMG signal of about 10 to 20 μV on the EMG probe 350 for about 1 second.

FIGS. 18A-18B illustrate the outer surface of a device having an elongate body having two regions 446, 448, wherein each region includes at least one bipole pair. The bipole pairs in the different regions may have different geometries. For example the bipole pair in the second region 444 is spaced further apart (D2>D1) than the bipole pair in the first region 442. This may result in the bipole pair in the second region projecting the bipole field further into the tissue than the bipole pair in the first region.

The configuration shown in FIG. 18B is similar, but illustrates a bipole network 449 in the second region 444 that is a tripolar electrode, having two anodes (−) separated from the cathode (+) in this example by different distances D2, D3. A bipole network may include additional cathodes and electrodes that are typically electrically coupled (e.g., to the same anodal or cathodal conductor) so that they can be stimulated substantially simultaneously.

Methods of Operation

In general, a method of determining if a nerve is nearby a device, or a region of a device, includes the steps of exciting a bipole pair or a bipole network to pass current between the bipole pair, resulting in a limited broadcast field that can stimulate a nearby neuron. The broadcast field may be limited by the geometry of the tight bipole pairs and the bipole networks described herein, and by the applied energy. It can then be determined if a nerve has been stimulated in response to the excitation of bipole pair or network; the magnitude of the response can also be compared for different bipole networks (or bipole pairs) in different regions of the device to determine which region is nearest the nerve.

FIGS. 19A-19C are flow diagrams illustrating methods of determining if a nerve is near a device as described herein. In the algorithm 380 shown in FIG. 19A a first bipole network (or bipole pair) located on a first region or section of a device having two or more regions is energized 382. The bipole network may be energized by the application of signal for a predetermined time interval. The energization of the bipolar module may generate a current between an anode (−) and cathode (+) (or anodes and cathodes). The subject is then monitored to determine if a response is detected 384. If a response is detected, then a nerve may be nearby. The first bipole network may be energized with a first signal for a first predetermined time interval. In some variations, the first bipole network is energized as the device is moved within the tissue (e.g., as it is advanced) to continuously sense if a nerve is nearby. For example, FIG. 19B illustrates one method of sensing as advancing.

In FIG. 19B the bipole pair in the first region is energized and a response (or lack of a response) is determined. The bipole network (or pair) may be energized as described above. For example, a continuous signal may be applied, a periodic signal may be applied, or a varying (e.g., ramping) signal may be applied 392. A response may be detected by muscle twitch, nerve firing, or otherwise 394. The device can then be moved based on the response 396, or continued to be moved based on the response. Movement may be continued in the same direction (e.g., if no response is detected) or in a new direction (if a nerve is detected). Movement may also be stopped if a nerve is detected. Steps 394 and 396 may be repeated during motion to guide the device.

In some variations, multiple regions of the device are stimulated to determine if a nerve is nearby. For example, FIG. 19C illustrates one variation in which a second region of the device, having its own, separated bipole network, is stimulated. In FIG. 19C, the first bipole network (or a bipole pair) in the first region is energized 532, and the patient is monitored for a response 534 to the stimulation. The bipole pair in a second region is then energized 536, and the patient is monitored for a response 538. Additional energizing and monitoring steps (not shown) may also be included for other regions of the device, if present. The responses to the different region can be compared 542, and the device can be moved in response to the presence of a nerve in one or more of the regions 546. Optionally, it may be determined which region of the device is closer to the nerve 544. If the nerve is detected, the tissue may be acted on (e.g., cut, ablated, removed, etc., or the device may be further oriented by moving it, and these steps may be repeated. If no nerve is detected, the steps may be repeated until the device is positioned as desired, and a procedure may then be performed.

In some variations, the device may be used to position (or form a passage for) another device or a region of the device that acts on the tissue. For example, the device may be used to position a guide channel or guide wire. In some variations, the method may include repeatedly energizing only a subset of the bipole networks (or bipole pairs) until a nerve is detected, and then other bipole networks on the device may be energized to determine with more accuracy the relationship (e.g., orientation) of the nerve with respect to the device.

As mentioned, the step of monitoring or detecting a response may be performed manually (e.g., visually), or using a sensor or sensor. For example, using an accelerometer may be coupled to muscle. The accelerometer may be a multiple axis accelerometer that detects the movement of the muscle in any direction, and movement coordinated with stimulation may be detected. In some variations, a strain gauge may be used on muscle innervated by a nerve passing through or originating in the region of tissue being examined. The strain gauge may be a multiple axis strain gauge that detects the movement of the muscle in any direction. In some variations, an EMG probe may be used to measure evoked potentials of the muscle. The magnitude of any response may also be determined.

Systems

Any of the devices described herein may be used as part of a system, which may be referred to as a nerve localization system. Systems may include components (e.g., hardware, software, or the like) to execute the methods described herein.

Figure 20:
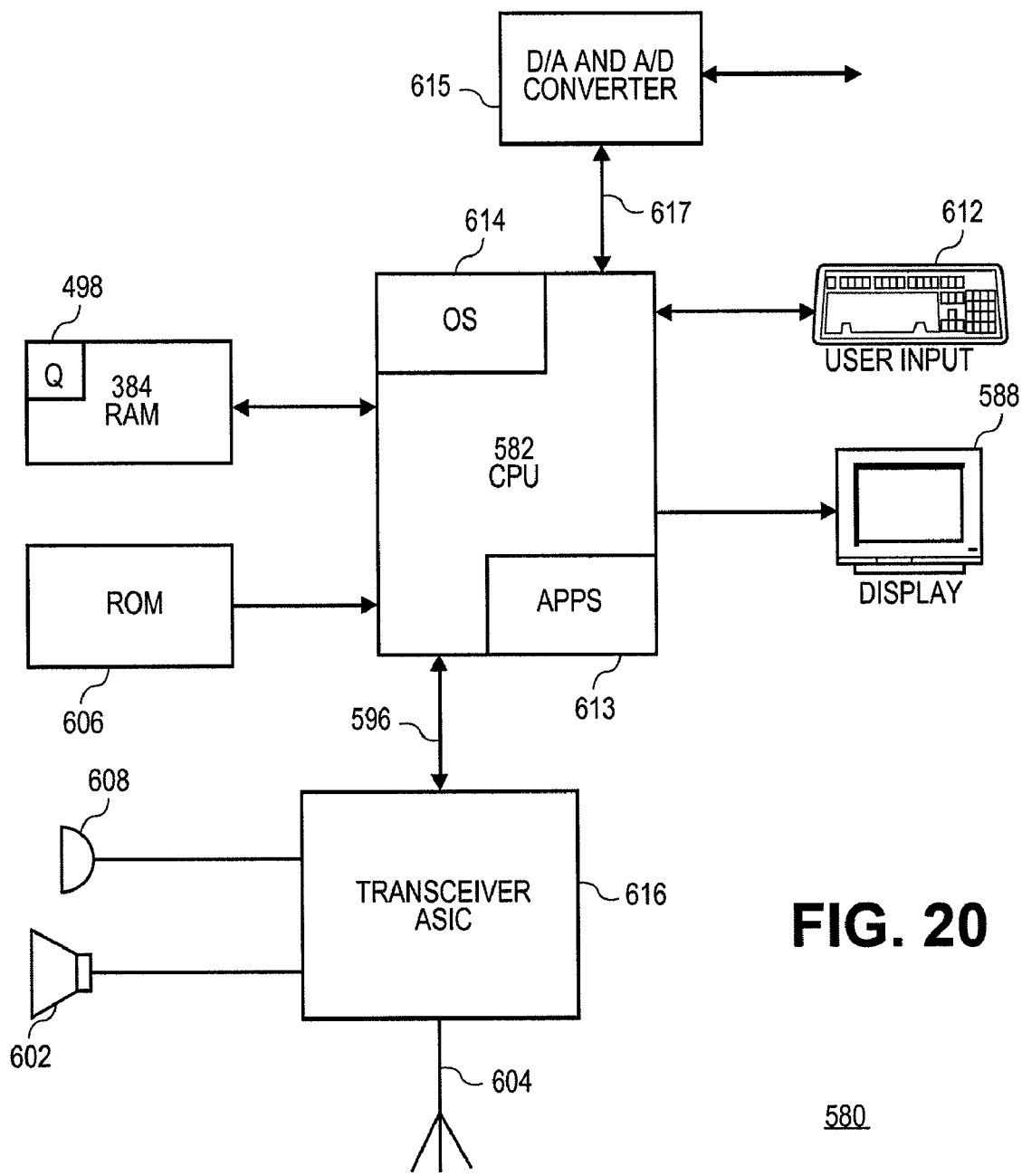
FIG. 20 is a block diagram illustrating components that may be part of a system for determining if a nerve is nearby a device.

FIG. 20 is a block diagram of additional components of a system 580 for determining if a nerve is nearby a device. The components 580 shown in FIG. 20 may be used with any of the devices described herein, and may include any computing device, including a personal data assistant, cellular telephone, laptop computer, or desktop computer. The system may include a central processing unit (CPU) 582, a random access memory (RAM) 584, a read only memory (ROM") 606, a display 588, a user input device 612, a transceiver application specific integrated circuit (ASIC) 616, a digital to analog (D/A) and analog to digital (A/D) convertor 615, a microphone 608, a speaker 602, and an antenna 604. The CPU 582 may include an OS module 614 and an application module 613. The RAM 584 may include a queue 598 where the queue 598 may store signal levels to be applied to one or more bipolar modules 46, 48. The OS module 614 and the application module 613 may be separate elements. The OS module 614 may execute a computer system or controller OS. The application module 612 may execute the applications related to the control of the system.

The ROM 606 may be coupled to the CPU 582 and may store program instructions to be executed by the CPU 582, OS module 614, and application module 613. The RAM 584 is coupled to the CPU 582 and may store temporary program data, overhead information, and the queues 598. The user input device 512 may comprise an input device such as a keypad, touch pad screen, track ball or other similar input device that allows the user to navigate through menus in order to operate the article 580. The display 588 may be an output device such as a CRT, LCD, LED or other lighting apparatus that enables the user to read, view, or hear user detectable signals.

The microphone 608 and speaker 602 may be incorporated into the device. The microphone 608 and speaker 602 may also be separated from the device. Received data may be transmitted to the CPU 582 via a serial bus 596 where the data may include signals for a bipole network. The transceiver ASIC 616 may include an instruction set necessary to communicate data, screens, or signals. The ASIC 616 may be coupled to the antenna 604 to communicate wireless messages, pages, and signal information within the signal. When a message is received by the transceiver ASIC 616, its corresponding data may be transferred to the CPU 582 via the serial bus 596. The data can include wireless protocol, overhead information, and data to be processed by the device in accordance with the methods described herein.

The D/A and A/D convertor 615 may be coupled to one or more bipole networks to generate a signal to be used to energize them. The D/A and A/D convertor 615 may also be coupled to one or more sensors 322, 324 to monitor the sensor 322, 324 state or condition.

Any of the components previously described can be implemented in a number of ways, including embodiments in software. These may include hardware circuitry, single or multi-processor circuits, memory circuits, software program modules and objects, firmware, and combinations thereof, as desired by the architect of the system 10 and as appropriate for particular implementations of various embodiments.

EXAMPLE 1

Neural Localization When Treating Spinal Stenosis

One area of surgery which could benefit from the development of less invasive techniques including neural localization is the treatment of spinal stenosis. Spinal stenosis often occurs when nerve tissue and/or blood vessels supplying nerve tissue in the lower (or "lumbar") spine become impinged by one or more structures pressing against them, causing pain, numbness and/or loss of function in the lower back and/or lower limb(s). In many cases, tissues such as ligamentum flavum, hypertrophied facet joint and bulging intervertebral disc impinge a nerve root as it passes from the cauda equine (the bundle of nerves that extends from the base of the spinal cord) through an intervertebral foramen (one of the side-facing channels between adjacent vertebrae). Here we provide one example of a device for determining if a nerve is nearby that may be used as part of method for treating spinal stenosis.

Figure 21:
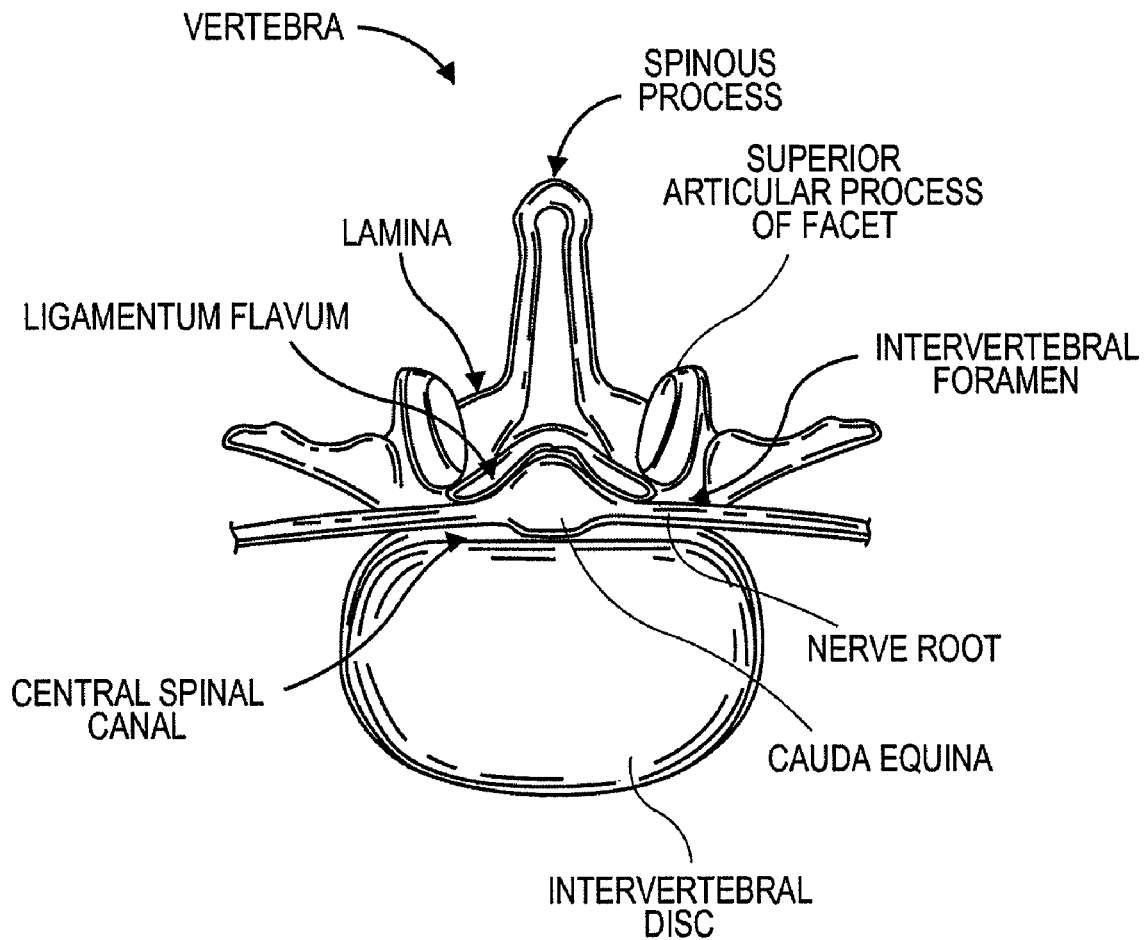
FIG. 21 is a cross-sectional view of a spine, showing a top view of a lumbar vertebra, a cross-sectional view of the cauda equina, and two exiting nerve roots.
Figure 22:
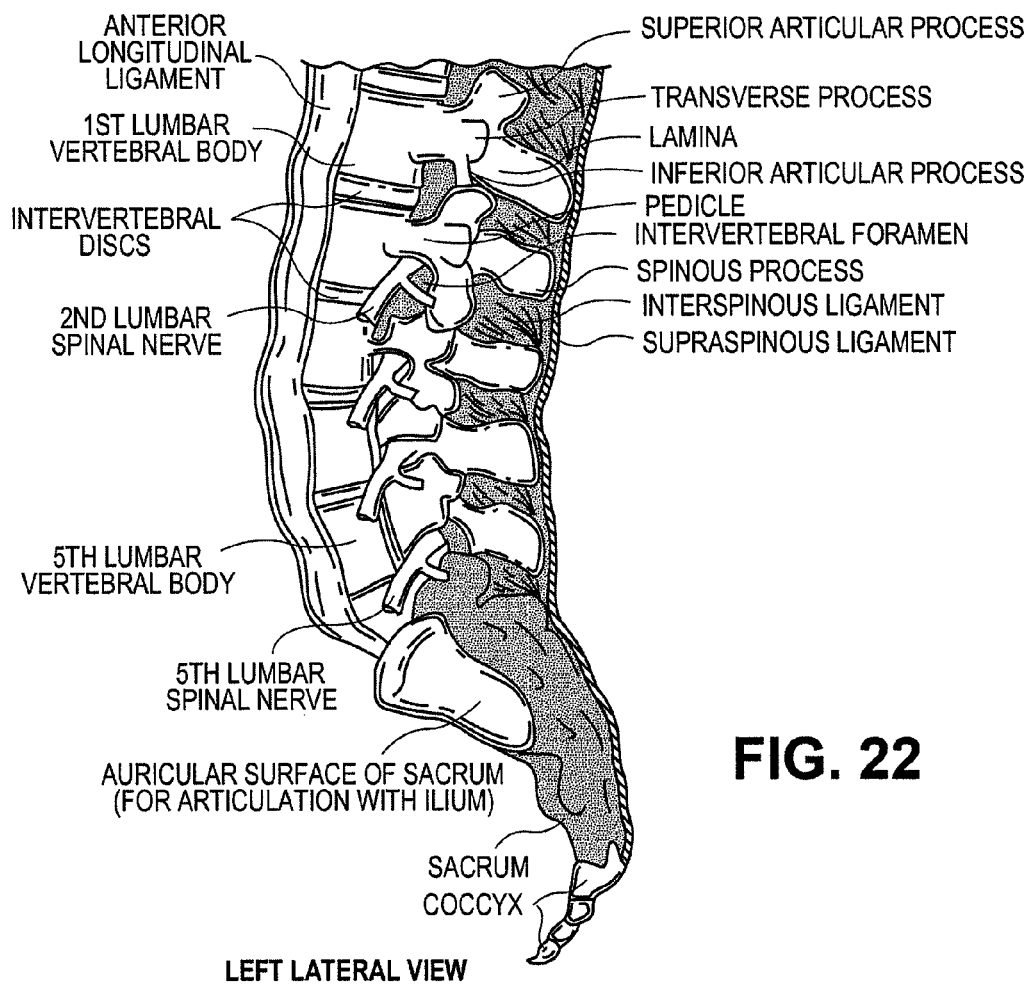
FIG. 22 is a side view of a lumbar spine.

FIG. 21 is a top view of a vertebra with the cauda equina shown in cross section and two nerve roots branching from the cauda equina to exit the central spinal canal and extend through intervertebral foramina on either side of the vertebra. FIG. 22 is a side view of the lumbar spine, showing multiple vertebrae, the intervertebral foramina between adjacent vertebrae, and the 1st-5th spinal nerves exiting the foramina.

Surgery may be required to remove impinging tissue and decompress the impinged nerve tissue of a spinal stenosis. Lumbar spinal stenosis surgery typically involves first making an incision in the back and stripping muscles and supporting structures away from the spine to expose the posterior aspect of the vertebral column. Thickened ligamentum flavum is then exposed by complete or partial removal of the bony arch (lamina) covering the back of the spinal canal (laminectomy or laminotomy). In addition, the surgery often includes partial or complete facetectomy (removal of all or part of one or more facet joints), to remove impinging ligamentum flavum or bone tissue. Spinal stenosis surgery is performed under general anesthesia, and patients are usually admitted to the hospital for five to seven days after surgery, with full recovery from surgery requiring between six weeks and three months. Many patients need extended therapy at a rehabilitation facility to regain enough mobility to live independently.

Removal of vertebral bone, as in laminectomy and facetectomy, often leaves the affected area of the spine very unstable, requiring an additional highly invasive fusion procedure that puts extra demands on the patient's vertebrae and limits the patient's ability to move. Unfortunately, a surgical spine fusion results in a loss of ability to move the fused section of the back, diminishing the patient's range of motion and causing stress on the discs and facet joints of adjacent vertebral segments. Such stress on adjacent vertebrae often leads to further dysfunction of the spine, back pain, lower leg weakness or pain, and/or other symptoms. Furthermore, using current surgical techniques, gaining sufficient access to the spine to perform a laminectomy, facetectomy and spinal fusion requires dissecting through a wide incision on the back and typically causes extensive muscle damage, leading to significant post-operative pain and lengthy rehabilitation. Thus, while laminectomy, facetectomy, and spinal fusion frequently improve symptoms of neural and neurovascular impingement in the short term, these procedures are highly invasive, diminish spinal function, drastically disrupt normal anatomy, and increase long-term morbidity above levels seen in untreated patients.

A number of devices, systems and methods for less invasive treatment of spinal stenosis have been described, for example, in U.S. patent application Ser. No. 11/250,332, entitled "Devices and Methods for Selective Surgical Removal of Tissue," and field Oct. 15, 2005; Ser. No. 11/375,265, entitled "Method and Apparatus for Tissue Modification," and field Mar. 13, 2006; and Ser. No. 11/535,000, entitled Tissue Cutting Devices and Methods," and field Sep. 25, 2006, all of which applications are hereby incorporated fully be reference herein.

Challenges in developing and using less invasive or minimally invasive devices and techniques for treating neural and neurovascular impingement include accessing hard-to-reach target tissue and locating nerve tissue adjacent the target tissue, so that target tissue can be treated and damage to nerve tissue can be prevented. These challenges may prove daunting, because the tissue impinging on neural or neurovascular tissue in the spine is typically located in small, confined areas, such as intervertebral foramina, the central spinal canal and the lateral recesses of the central spinal canal, which typically have very little open space and are difficult to see without removing significant amounts of spinal bone. The assignee of the present invention has described a number of devices, systems and methods for accessing target tissue and identifying neural tissue. Exemplary embodiments are described, for example, in U.S. patent application Ser. No. 11/251,205, entitled "Devices and Methods for Tissue Access," and field Oct. 15, 2005; Ser. No. 11/457,416, entitled "Spinal Access and Neural Localization," and field Jul. 13, 2006; and Ser. No. 11/468,247, entitled "Tissue Access Guidewire System and Method," and field Aug. 29, 2006, all of which applications are hereby incorporated fully be reference herein.

The methods and devices for neural localization described herein may be used in less invasive spine surgery procedures, including the treatment of spinal stenosis. For example, the methods and devices described herein can be used with minimal or no direct visualization of the target or nerve tissue, such as in a percutaneous or minimally invasive small-incision procedure.

Figure 23:
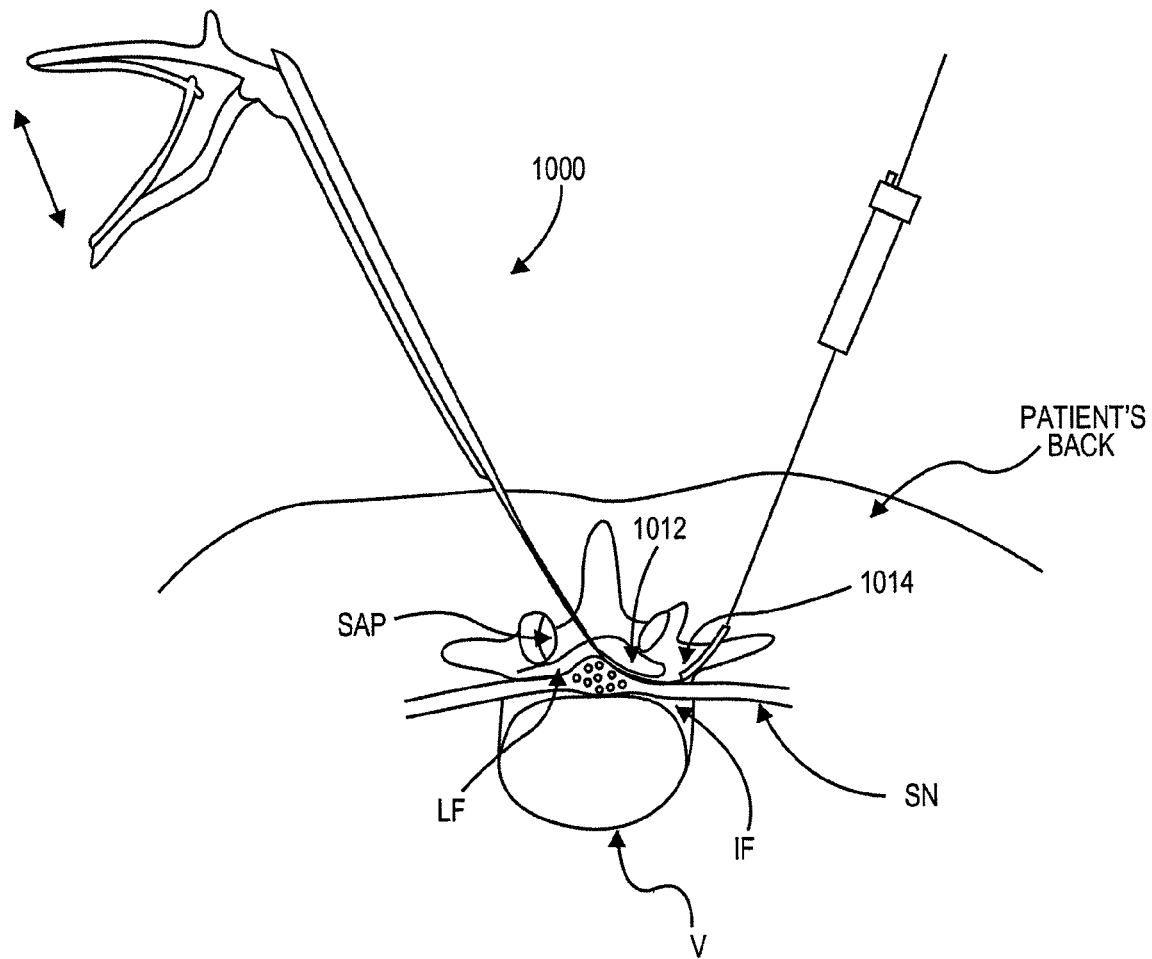
FIG. 23 is a cross-sectional view of a spine, illustrating a minimally invasive spinal decompression device and method including the use of neural localization as described herein.

FIG. 23 illustrates one device for treatment of spinal stenosis including a tissue cutting device 1000 including a guidewire. For further explanation of guidewire systems and methods for inserting device 1000 and other tissue removal or modification devices, reference may also be made to U.S. patent application Ser. Nos. 11/468,247 and 11/468,252, both titled "Tissue Access Guidewire System and Method," and both field Aug. 29, 2006, the full disclosures of which are hereby incorporated by reference.

Cutting device 1000 may be at least partially flexible, and in some embodiments may be advanced through an intervertebral foramen IF of a patient's spine to remove ligamentum flavum LF and/or bone of a vertebra V, such as hypertrophied facet (superior articular process SAP in FIG. 23), to reduce impingement of such tissues on a spinal nerve SN and/or nerve root. In one embodiment, device 1000 cuts tissue by advancing a proximal blade 1012 on an upper side of device 1000 toward a distal blade 1014. This cutting device may be used with (or as part of) a system for determining if a nerve is nearby, and may prevent damage to nerves in the region which the device operates.

In various embodiments, device 1000 may be used in an open surgical procedure, a minimally invasive surgical procedure or a percutaneous procedure. In any procedure, it is essential for a surgeon to know that device 1000 is placed in a position to cut target tissue, such as ligament and bone, and to avoid cutting nerve tissue. In minimally invasive and percutaneous procedures, it may be difficult or impossible to directly visualize the treatment area, thus necessitating some other means for determining where target tissue and neural tissue are located relative to the tissue removal device. At least, a surgeon performing a minimally invasive or percutaneous procedure will want to confirm that the tissue cutting portion of device 1000 is not directly facing and contacting nerve tissue. The various nerve localization devices and systems described herein may help the surgeon verify such nerve/device location. A neural localization system and method may be used in conjunction with device 1000 or with any other tissue removal, tissue modification or other surgical devices. Furthermore, various embodiments may have applicability outside the spine, such as for locating nerve tissue in or near other structures, such as the prostate gland, the genitourinary tract, the gastrointestinal tract, the heart, and various joint spaces in the body such as the knee or shoulder, or the like. Therefore, although the following description focuses on the use of embodiments of the invention in the spine, all other suitable uses for the various embodiments described herein are also contemplated.

Figure 24:
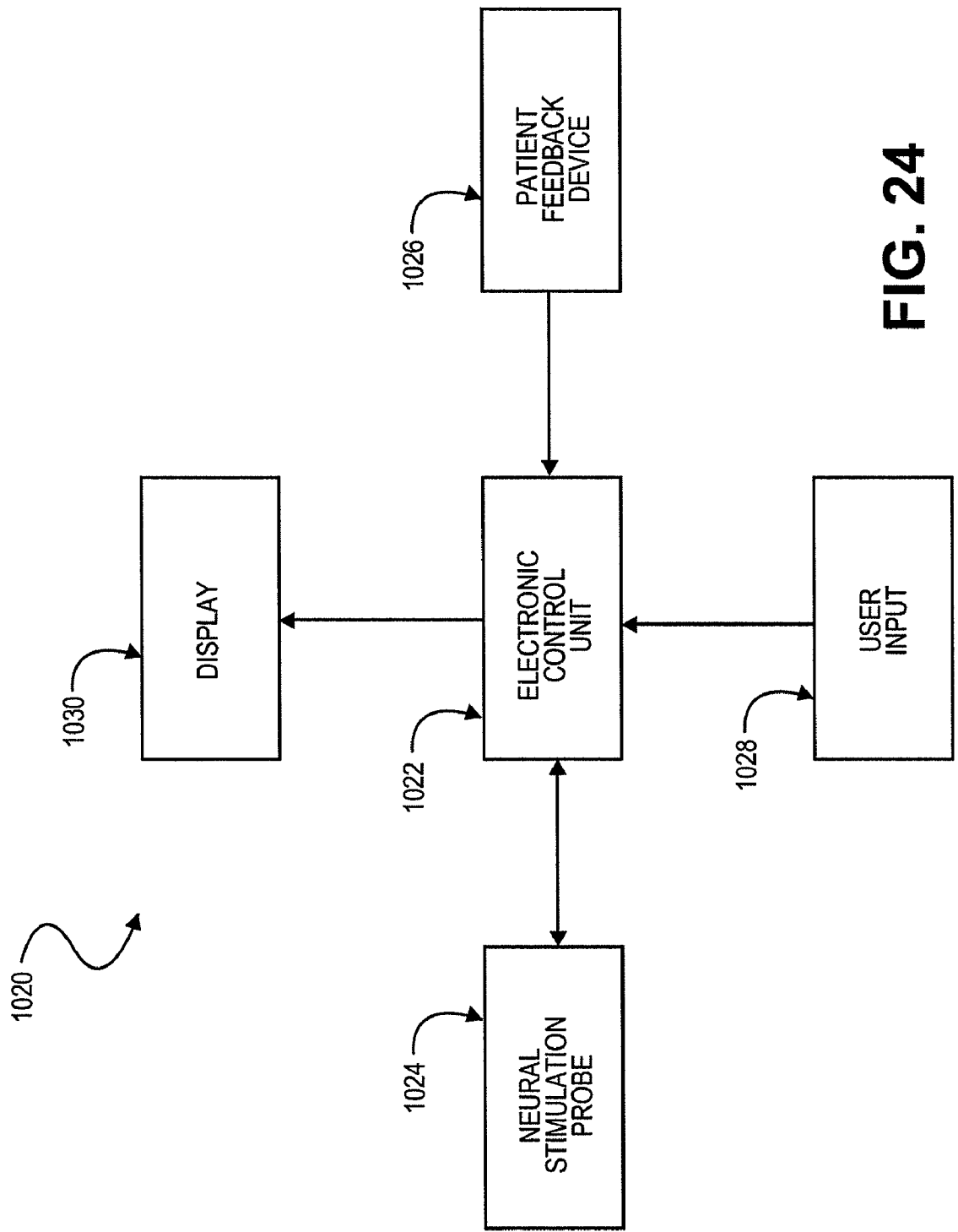
FIG. 24 is a block diagram of one variation of a nerve tissue localization system.

Referring now to FIG. 24, a diagrammatic representation of one embodiment of a nerve tissue localization system 1020 is shown. Neural localization system 1000 may include an electronic control unit 1024 and a neural stimulation probe 1024, a patient feedback device 1026, a user input device 1028 and a display 1030, all coupled with control unit 1022.

In one embodiment, electronic control unit (ECU) 1020 may include a computer, microprocessor or any other processor for controlling inputs and outputs to and from the other components of system 1020. In one embodiment, for example, ECU 1020 may include a central processing unit (CPU) and a Digital to Analog (D/A) and Analog to Digital Converter (A/D). ECU 1022 may include any microprocessor having sufficient processing power to control the operation of the D/A A/D converter and the other components of system 1020. Generally, ECU 1022 may control the operation of the D/A A/D converter and display device 1030, in some embodiments based on data received from a user via user input device 1028, and in other embodiments without input from the user. User input device 1028 may include any input device or combination of devices, such as but not limited to a keyboard, mouse and/or touch sensitive screen. Display device 1030 may include any output device or combination of devices controllable by ECU 1022, such as but not limited to a computer monitor, printer and/or other computer controlled display device. In one embodiment, system 1020 generates electrical signals (or other nerve stimulating energy signals in alternative embodiments), which are transmitted to electrodes on probe 1024, and receives signals from patient feedback device 1026 (or multiple feedback devices 1026 in some embodiments). Generally, ECU 1022 may generate a digital representation of signals to be transmitted by electrodes, and the D/A A/D converter may convert the digital signals to analog signals before they are transmitted to probe 1024. ECU 1022 also receive a return current from probe 1024, convert the current to a digital signal using the D/A A/D converter, and process the converted current to determine whether current was successfully delivered to the stimulating portion of probe 1024. The D/A A/D converter may convert an analog signal received by patient feedback device(s) 1026 into a digital signal that may be processed by ECU 1022. ECU 1022 may hold any suitable software for processing signals from patient feedback devices 1026, to and from probe 1024 and the like. According to various embodiments, display device 1030 may display any of a number of different outputs to a user, such as but not limited to information describing the signals transmitted to probe 1024, verification that stimulating energy was successfully delivered to a stimulating portion of probe 1024, information describing signals sensed by patient feedback devices 1026, a visual and/or auditory warning when a nerve has been stimulated, and/or the like. In various alternative embodiments, system 1020 may include additional components or a different combination or configuration of components, without departing from the scope of the present invention.

The neural stimulation probe 1024 is an elongate body having an outer surface including one or more regions with a bipole pair or bipole network. Furthermore, any suitable number of regions may be included on a given probe 1024. In various embodiments, for example, probe 1024 may includes two or more regions, each having a bipole pair or bipole network (comprising a plurality of bipole pairs) disposed along the probe in any desired configuration. In one embodiment, probe 1024 may include four regions, each having at least one bipole pairs, one pair on each of top, bottom, left and right sides of a distal portion of the probe that is configured to address neural tissue.

In some embodiments, ECU 1022 may measure current returned through probe 1024 and may process such returned current to verify that current was, in fact, successfully transmitted to a nerve stimulation portion of probe 1024. In one embodiment, if ECU 1022 cannot verify that current is being transmitted to the nerve stimulation portion of probe 1024, ECU 1022 may automatically shut off system 1020. In an alternative embodiment, if ECU 1022 cannot verify that current is being transmitted to the nerve stimulation portion of probe 1024, ECU 1022 may signal the user, via display device 1030, that probe 1024 is not functioning properly. Optionally, in some embodiments, system 1020 may include both a user signal and automatic shut-down.

Patient feedback device 1026 may include any suitable sensing device and typically includes multiple devices for positioning at multiple different locations on a patient's body. In some embodiments, for example, multiple motion sensors may be included in system 1020. Such motion sensors may include, but are not limited to, accelerometers, emitter/detector pairs, lasers, strain gauges, ultrasound transducers, capacitors, inductors, resistors, gyroscopes, and/or piezoelectric crystals. In one embodiment, where nerve tissue stimulation system 1020 is used for nerve tissue detection in the lumbar spine, feedback device 1026 may include multiple accelerometers each accelerometer attached to a separate patient coupling member, such as an adhesive pad, for coupling the accelerometers to a patient. In one such embodiment, for example, each accelerometer may be placed over a separate muscle myotome on the patients lower limbs.

When nerve tissue is stimulated by probe 1024, one or more patient feedback devices 1026 may sense a response to the stimulation and deliver a corresponding signal to ECU 1022. ECU 1022 may process such incoming signals and provide information to a user via display device 1030. For example, in one embodiment, information may be displayed to a user indicating that one sensor has sensed motion in a particular myotome. As part of the processing of signals, ECU 1022 may filter out "noise" or sensed motion that is not related to stimulation by probe 1024. In some embodiments, an algorithm may be applied by ECU 1022 to determine which of multiple sensors are sensing the largest signals, and thus to pinpoint the nerve (or nerves) stimulated by probe 1024.

In an alternative embodiment, patient feedback device 1026 may include multiple electromyography (EMG) electrodes. EMG electrodes receive EMG or evoked muscle action potential (EMAP) signals generated by muscle electrically coupled to EMG electrodes and to a depolarized nerve (motor unit). One or more nerves may be depolarized by one or more electrical signals transmitted by probe. As with the motion sensor embodiment, ECU 1022 may be programmed to process incoming information from multiple EMG electrodes and provide this processed information to a user in a useful format via display device 1030.

User input device 1028, in various embodiments, may include any suitable knob, switch, foot pedal, toggle or the like and may be directly attached to or separate and coupleable with ECU 1022. In one embodiment, for example, input device 1028 may include an on/off switch, a dial for selecting various bipolar electrode pairs on probe 1024 to stimulate, a knob for selecting an amount of energy to transmit to probe 1024 and/or the like.

Referring now to FIG. 1025, in one embodiment, a nerve tissue localization system 1040 may include an ECU 1042, a neural stimulation probe 1044, multiple patient feedback devices 1026, and a user input device 48. Probe 1044 may include, in one embodiment, a curved, flexible nerve stimulating elongate member 1058, which may slide through a rigid cannula 1056 having a handle 1054.

The probe 1044 is a device for determining if a nerve is nearby a region of the device, and includes a plurality of regions which each include one or more bipole pairs. In some variations the probe 1044 includes two regions (an upper region and a lower region), and each region includes a bipole network configured to form a continuous bipole field along the length of the probe in either the upper or lower regions. A nerve stimulating member 1058 may include a guidewire lumen for allowing passage of a guidewire 1059, for example after nerve tissue has been detected to verify that the curved portion of nerve stimulating member 1058 is in a desired location relative to target tissue TT and nerve tissue NT. Patient feedback devices 1046 and probe 1044 may be coupled with ECU 1042 via wires 1050 and 1052 or any other suitable connectors. ECU 1042 may include user input device 1048, such as a knob with four settings corresponding to top, bottom, left and right sides of a nerve tissue stimulation portion of nerve stimulating member 1058. ECU 1042 may also optionally include a display 1047, which may indicate an amount of muscle movement sensed by an accelerometer feedback device 1046. In one embodiment, ECU 1042 may include one or more additional displays, such as red and green lights 1049 indicating when it is safe or unsafe to perform a procedure or whether or not probe 1044 is functioning properly. Any other suitable displays may additionally or alternatively be provided, such as lamps, graphs, digits and/or audible signals such as buzzers or alarms.

In one embodiment, each of patient feedback devices 1046 may include an accelerometer coupled with an adhesive pad or other patient coupling device. In one embodiment, a curved portion of nerve stimulating member 1058 may be configured to pass from an epidural space of the spine at least partway through an intervertebral foramen of the spine. In other embodiments, nerve stimulating member 1058 may be straight, steerable and/or preformed to a shape other than curved.

Figure 25:
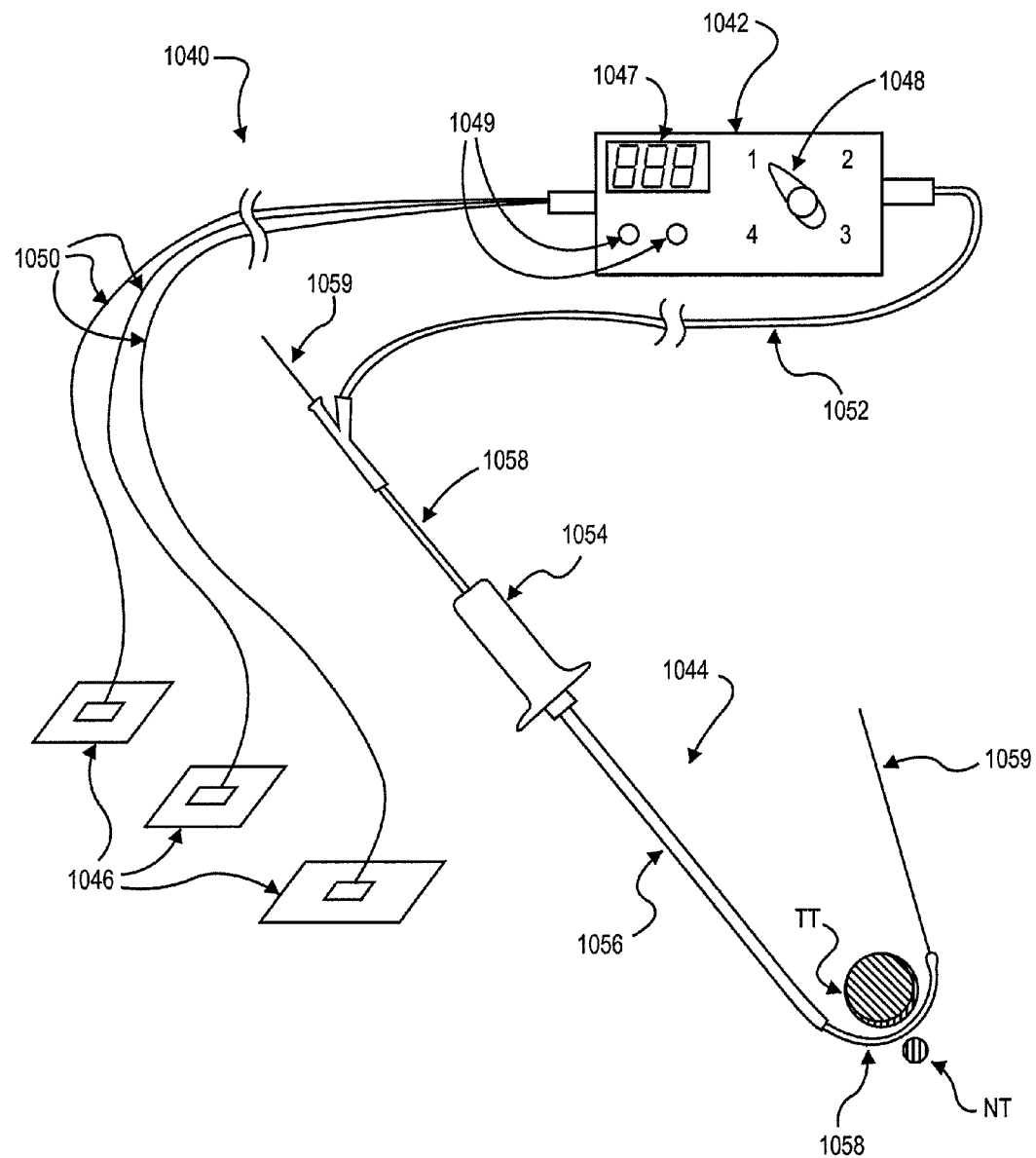
FIG. 25 is a perspective view of a nerve tissue localization system.
Figure 26A:
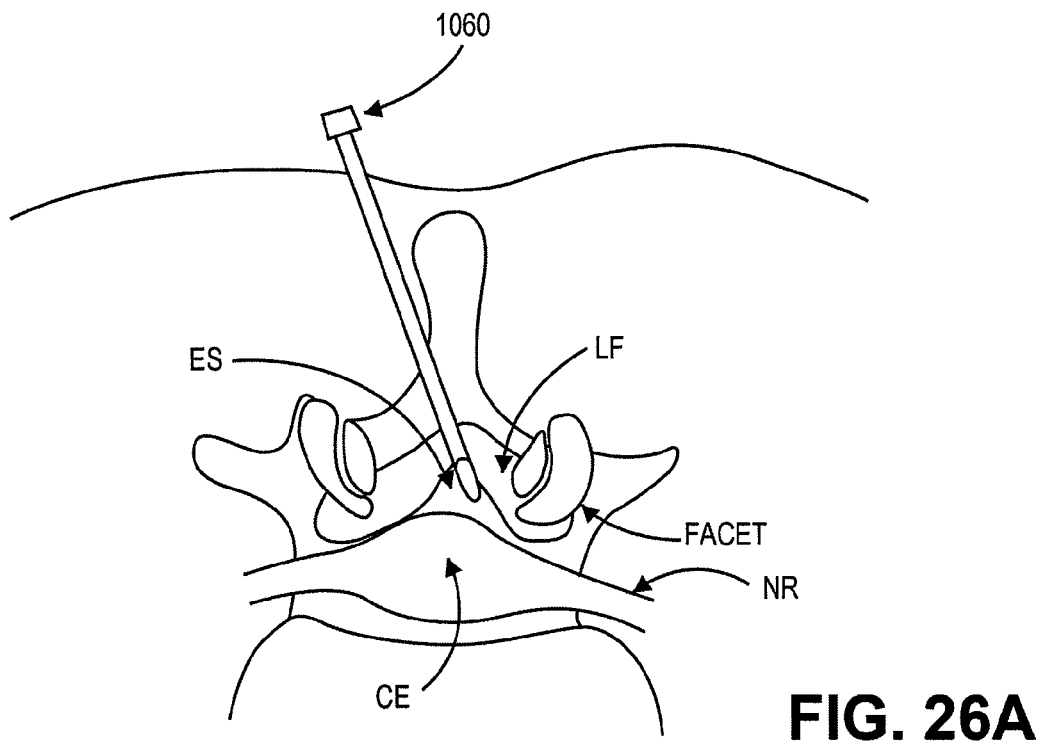
FIGS. 26A-26F are cross-sectional views of a spine, illustrating one method for using a nerve tissue localization system.
Figure 26B:
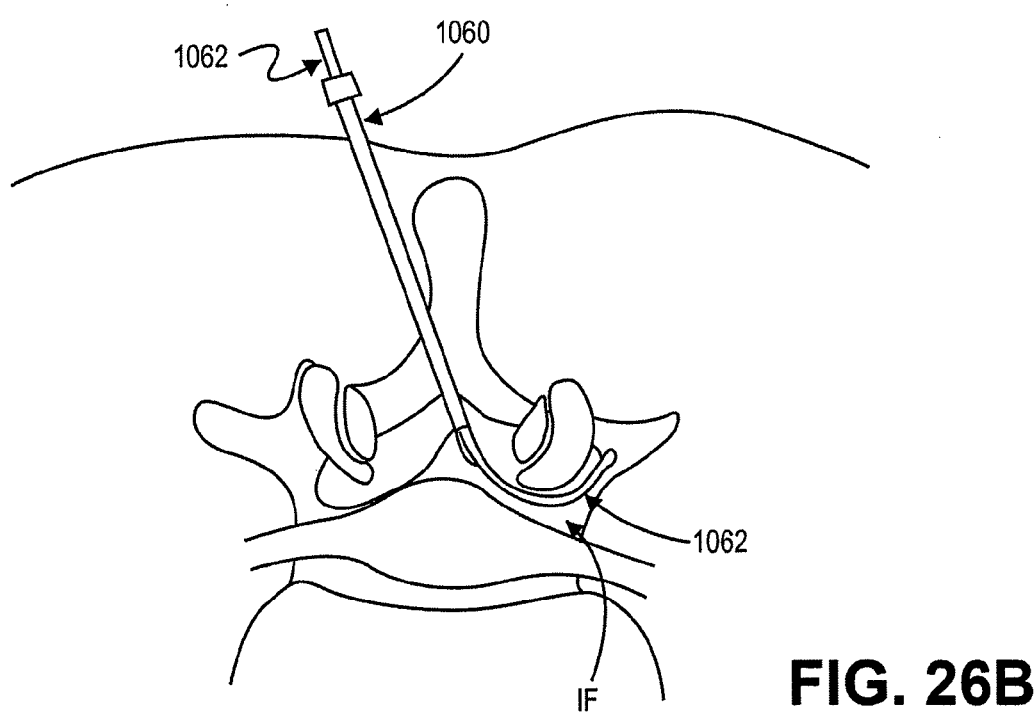

FIGS. 26A-26B and 26B describe a method for localizing nerve tissue and placing a guidewire in a desired location in a spine using the device configured to determine if a nerve is nearby. Before advancing a nerve tissue localization probe into the patient, and referring again to FIG. 25, multiple patient feedback devices 1046, such as accelerometers or EMG electrodes, may be placed on the patient, and ECU 1042 may be turned on. In one embodiment, a test current may be transmitted to probe 1044, and a return current from probe 1044 may be received and processed by ECU 1042 to verify that probe 1044 is working properly.

Figure 26C:
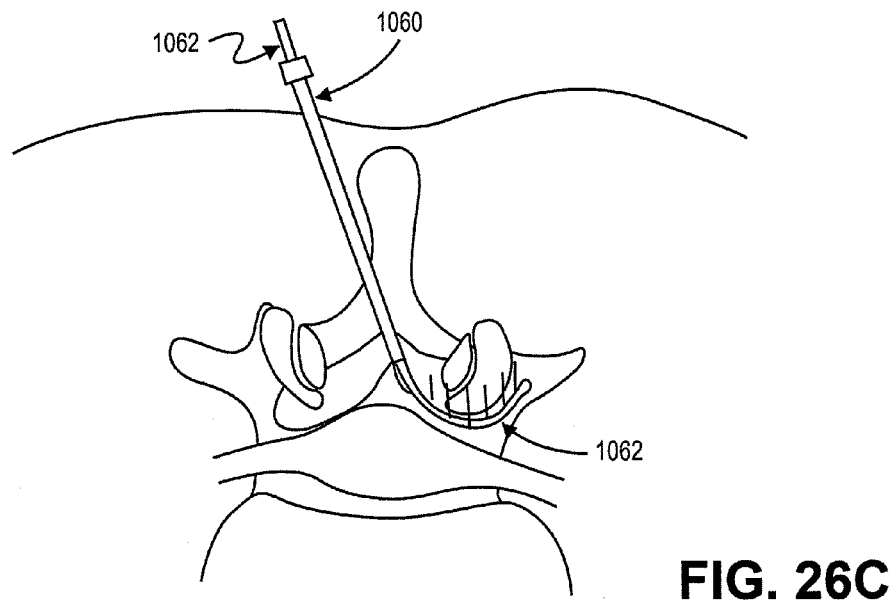
Figure 26D:
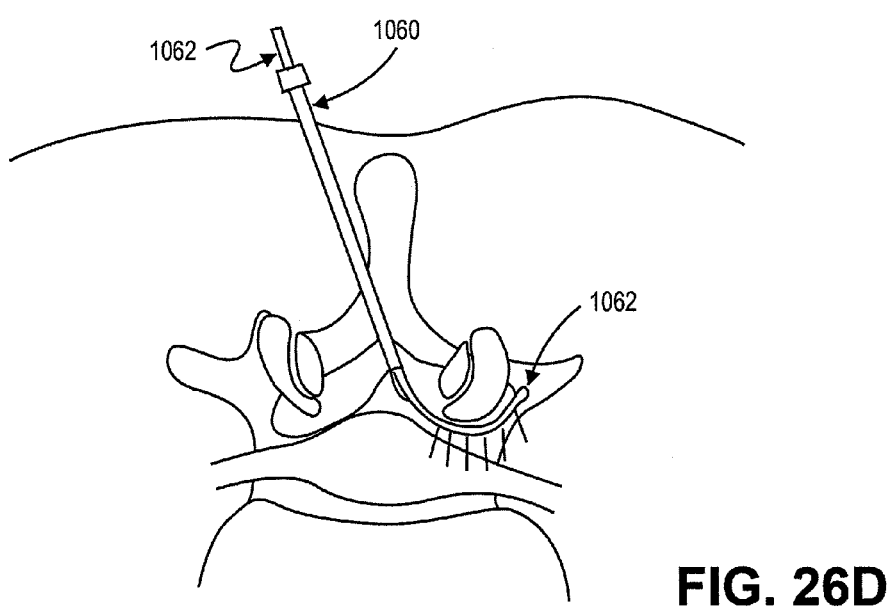

As shown in FIG. 26A, an epidural needle 1060 (or cannula) may be passed through the patient's skin, and a distal tip of needle 1060 may be advanced through the ligamentum flavum LF of the spine into the epidural space ES. Next, as shown in FIG. 26B, a probe that is configured to determine if a nerve is nearby the probe 1062 may be passed through epidural needle 1060, such that a curved, flexible, distal portion passes into the epidural space ES and through an intervertebral foramen IF of the spine, between target tissue (ligamentum flavum LF and/or facet bone) and non-target neural tissue (cauda equina CE and nerve root NR). As shown in FIG. 26C, the upper region of the probe having a first bipole network may be energized to generate a bipole field as current passes between the anodes and cathodes of the bipole network in the upper region 1062. In some variations, the bipole pairs may be monitored to confirm that transmitted energy returned proximally along the probe, as described previously. As shown in FIG. 26D, the lower bipole network may then be energized to generate a bipole field from the curved portion of probe 1062. In an alternative embodiment, energy may be transmitted only to the top, only to the bottom, or to the bottom first and then the top regions. In some embodiments, energy may be further transmitted to electrodes on left and right regions of probe 1062. Depending on the use of a given probe 1062 and thus its size constraints and the medical or surgical application for which it is being used, any suitable number of electrodes may form the bipole network of a particular region.

As energy is transmitted to the bipole network in any region of the probe 1062, patient response may be monitored manually or via multiple patient feedback devices (not shown in FIG. 26), such as, but not limited to, accelerometers or EMG electrodes. In one method, the same amount of energy may be transmitted to the bipole network in the different regions of the probe in series, and amounts of feedback sensed to each transmission may be measured and compared to help localize a nerve relative to probe 1062. If a first application of energy does not generate any response in the patient, a second application of energy at higher level(s) may be tried and so forth, until a general location of nerve tissue can be determined. In an alternative embodiment, the method may involve determining a threshold amount of energy required by bipole network to stimulate a response in the patient. These threshold amounts of energy may then be compared to determine a general location of the nerve relative to the probe. In another alternative embodiment, some combination of threshold and set-level testing may be used.

Figure 26E:
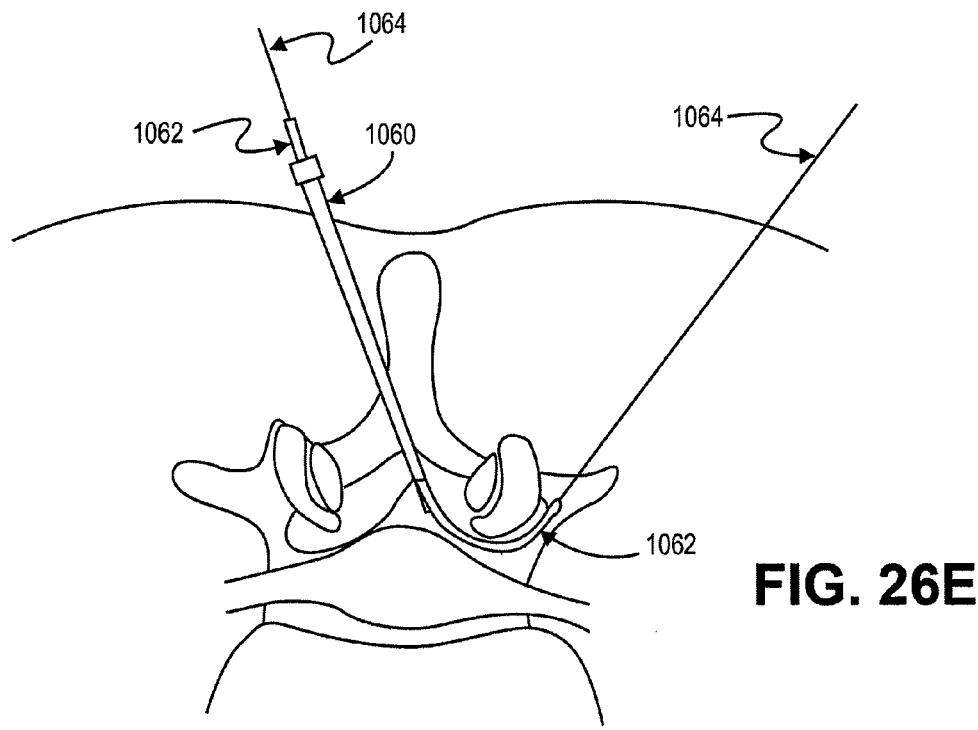
Figure 26F:
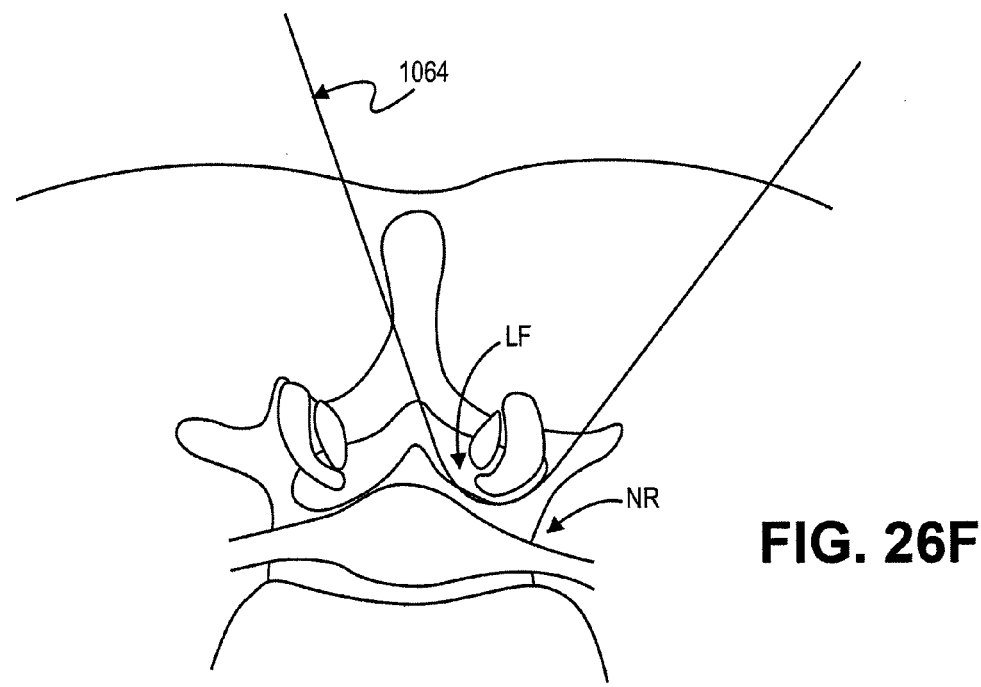

In one embodiment, as shown in FIG. 26E, nerve probe 1062 may include a guidewire lumen through which a guidewire may be passed, once it is determined that device 1062 is placed in a desired position between target and non-target tissue (e.g., avoiding a nerve adjacent to the upper region). As shown in FIG. 26F, when epidural needle 1060 and probe 1062 are removed, guidewire 1064 may be left in place between target tissue (such as ligamentum flavum LF and/or facet bone) and non-target tissue (such as cauda equina CE and nerve root NR). Any of a number of different minimally invasive or percutaneous surgical devices may then be pulled into the spine behind guidewire 1064 or advanced over guidewire 1064, such as the embodiment shown in FIG. 23 and others described by the assignee of the present application in other applications incorporated by reference herein.

Figure 27A:
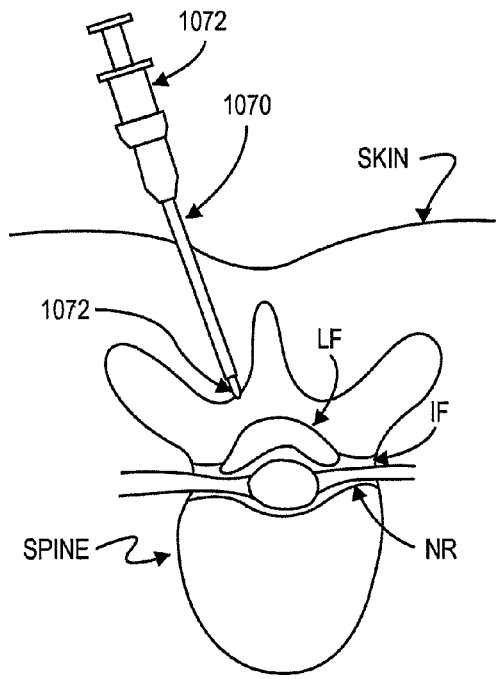
FIGS. 27A-27H are cross-sectional views of a spine, illustrating another method for using a nerve tissue localization system.
Figure 27B:
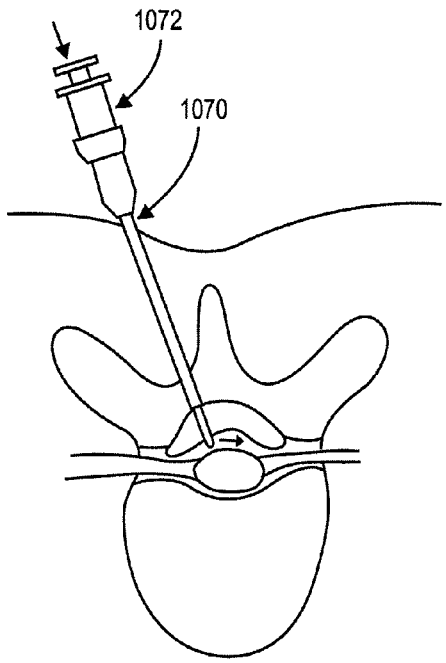
Figure 27C:
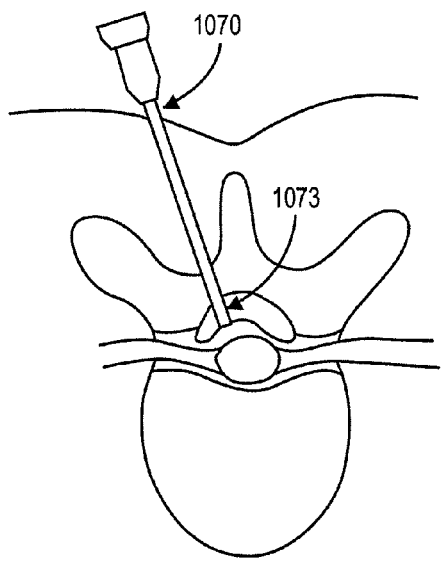

Referring now to FIGS. 27A-27H, another embodiment of a method for accessing an intervertebral foramen IF and verifying a location of a probe relative to tissue (such as ligamentum flavum LF and nerve/nerve root NR tissue) is demonstrated. In this embodiment, as shown in FIG. 27A, an access cannula 1070 may be advanced into the patient over an epidural needle 1072 with attached syringe. As shown in FIG. 27B, cannula 1070 and needle 1072 may be advanced using a loss of resistance technique, as is commonly performed to achieve access to the epidural space via an epidural needle. Using this technique, when the tip of needle 1072 enters the epidural space, the plunger on the syringe depresses easily, thus passing saline solution through the distal end of needle 1072 (see solid-tipped arrows). As shown in FIG. 27C, once epidural access is achieved, needle can be withdrawn from the patient, leaving cannula in place with its distal end contacting or near ligamentum flavum LF. Although needle 1072 may be removed, its passage through ligamentum flavum LF may leave an opening 1073 (or path, track or the like) through the ligamentum flavum LF.

Figure 27D:
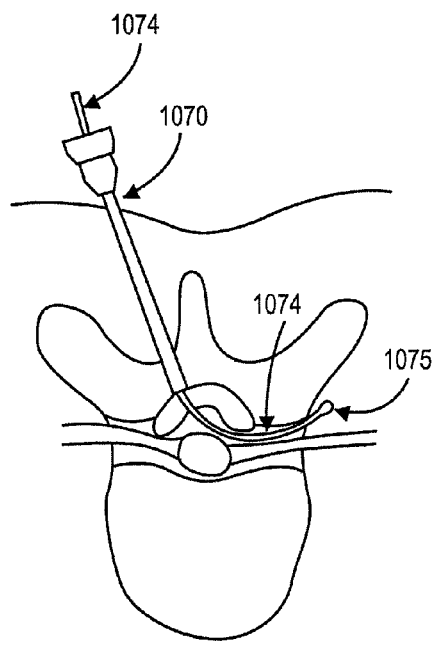

As shown in FIG. 27D, a curved, flexible guide 1074 having an atraumatic distal tip 1075 may be passed through cannula 1070 and through opening 1073 in the ligamentum flavum LF, to extend at least partway through an intervertebral foramen IF. In this variation, the guide 1074 is configured as a device for determining if a nerve is nearby a region of the device. The guide 1074 is an elongate member that includes at least a first region having a bipole pair, or more preferably a bipole network thereon.

Figure 27E:
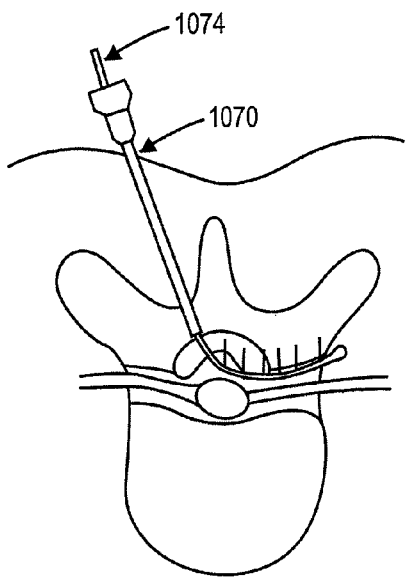
Figure 27F:
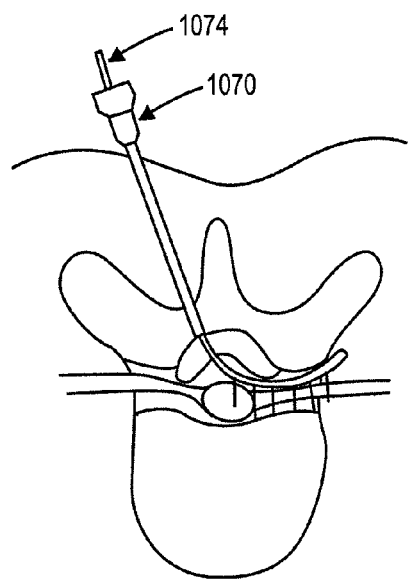

In FIG. 27E, a first bipole network on or near an external surface of guide 1074 may then be energized, and the patient may be monitored for response. As in FIG. A7F, a second bipole network disposed along guide 1074 in a different circumferential region than the region may be energized, and the patient may again be monitored for response. This process of activation and monitoring may be repeated for any number of bipole networks or as the device is manipulated in the tissue, according to various embodiments. For example, in one embodiment, guide 1074 may include a first region having a bipole network on its top side (inner curvature), a second region having a bipole network on the bottom side (outer curvature), and a third and fourth region each having a bipole network on the left side and right side, respectively. A preselected amount of electrical energy (current, voltage, and/or the like) may be transmitted to a bipole network, and the patient may be monitored for an amount of response (EMG, muscle twitch, or the like). The same (or a different) preselected amount of energy may be transmitted to a second bipole network, the patient may be monitored for an amount of response, and then optionally the same amount of energy may be transmitted sequentially to third, fourth or more bipole networks, while monitoring for amounts of response to each stimulation. The amounts of response may then be compared, and from that comparison a determination may be made as to which region is closest to nerve tissue and/or which region is farthest from nerve tissue.

In an alternative method, energy may be transmitted to a first bipole electrode and the amount may be adjusted to determine a threshold amount of energy required to elicit a patient response (EMG, muscle twitch, or the like). Energy may then be transmitted to a second bipole network, adjusted, and a threshold amount of energy determined. Again, this may be repeated for any number of bipole networks (e.g., regions). The threshold amounts of required energy may then be compared to determine the location of the regions relative to nerve tissue.

Figure 27G:
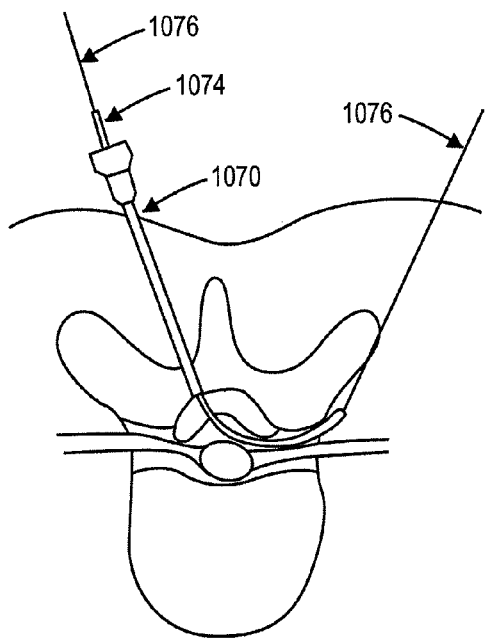
Figure 27H:
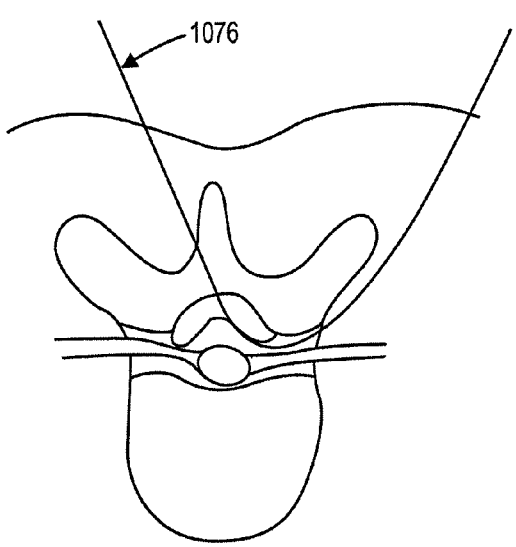

Referring now to FIG. 27G, once it is verified that guide 1074 is in a desired position relative to nerve tissue and/or target tissue, a guidewire 1076 may be passed through guide and thus through the intervertebral foramen IF and out the patient's skin. Cannula 1070 and guide 1074 may then be withdrawn, leaving guidewire 1076 in place, passing into the patient, through the intervertebral foramen, and back out of the patient. Any of a number of devices may then be pulled behind or passed over guidewire 1076 to perform a procedure in the spine.

Rotating a Tight Bipole Pair

Another variation of nerve localizing device including one or more tight bipole pairs is a device having at least one tight bipole pair that can be scanned (e.g., rotated) over at least a portion of the circumference of the device to detect a nearby nerve.

In general, a device having a movable tight bipole pair may include an elongate body that has an outer surface and at least one bipole pair that can be scanned (moved) with respect to the outer surface of the device so as to be energized in different regions of the outer surface of the device to determine if a nerve is nearby. For example, a device may include an elongate body having an outer surface that can be divided up into a plurality of circumferential regions and a scanning that is movable with respect to the outer surface. At least one tight bipole pair (or a bipole network) is attached to the scanning surface, allowing the bipole pair or network to be scanned to different circumferential regions.

Figure 28A:
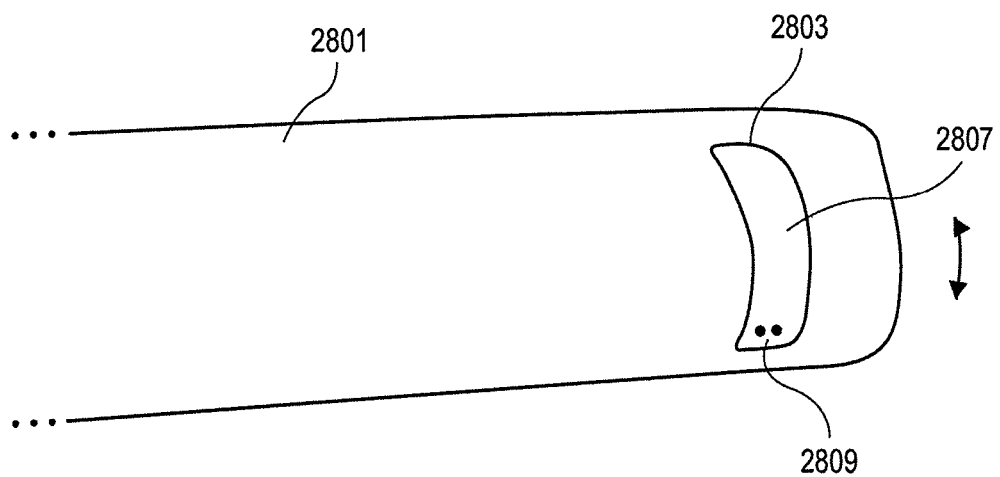
FIGS. 28A and 28B show variations of devices for determining if a nerve is nearby.
Figure 28B:
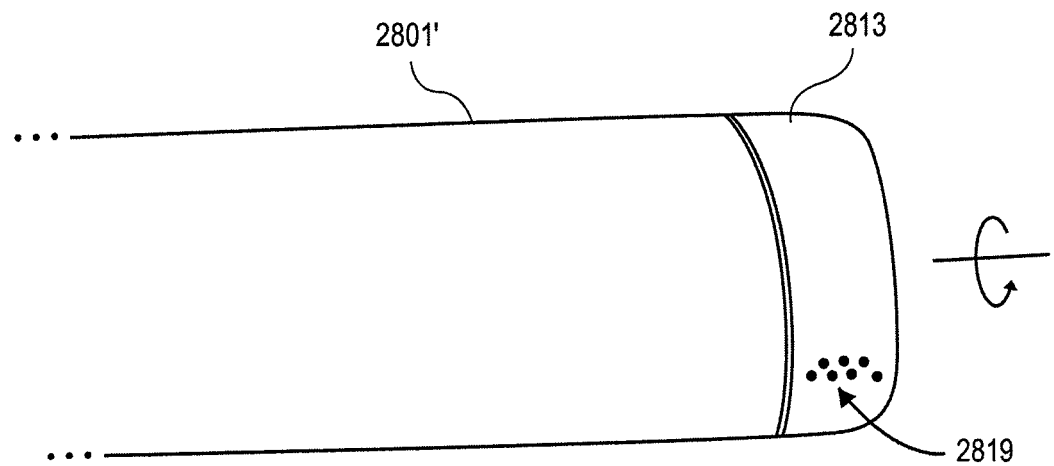

FIGS. 28A and 28B illustrate variations of a device having a scanning or movable bipole pair (or bipole network). For example, FIG. 28A includes an elongate body 2801 having an outer surface. In this variation the elongate body has a circular or oval cross-section, although other cross-sectional shapes may be used, including substantially flat. The surface of the outer body includes a window 2803 region exposing a scanning surface 2807 to which at least one bipole pair is connected. The scanning surface may be moved relative to the outer surface (as indicated by the arrow). In this example, the window extends circumferentially, and the scanning surface may be scanned radially (e.g., up and down with respect to the window).

FIG. 28B illustrates another variation, in which the distal end of the elongate body 2801' is rotatable with respect to the more proximal region of the device. The distal end includes one or more bipole pairs. In FIG. 28 the rotatable distal end includes a bipole network 2819. The bipole network may be energized as it is rotated, or it may be rotated into different positions around the circumference of the device and energized after it has reached each position.

The devices illustrated in FIGS. 28A and 28B may include a controller configured to control the scanning (i.e., rotation) of the bipole pair. The device may also include a driver for driving the motion of the bipole pair. For example, the drive may be a motor, magnet, axel, shaft, cam, gear, etc. The controller may control the driver, and may control the circumferential position of the bipole pair (or bipole network). The device may also include an output for indicting the circumferential region of the bipole network or pair.

In operation, the scanning bipole pair can be used to determine if a nerve is near the device by moving the bipole pair or network with respect to the rest of the device (e.g., the outer surfaced of the elongate body). For example, the device may be used to determine if a nerve is nearby the device by scanning the bipole pair (or a bipolar network comprising a plurality of bipole pairs) across a plurality of circumferential regions of the outer surface of the elongate body, and by energizing the bipole pair(s) when it is in one of the circumferential regions. As mentioned, the bipole pair(s) may be energized as they are moved, or they may be energized once they are in position. The movement may be reciprocal (e.g., back and forth) or rotation, or the like.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of detecting if a nerve is above or below a given region of a device in tissue, the method comprising:
    positioning a guidewire within the tissue of a patient;
    positioning a device within the tissue using the guidewire, wherein the device comprises a flexible elongate body having an outer surface including an upper surface that is opposite a lower surface and plurality of anodes and cathodes on the outer surface;
    determining a threshold amount of energy required to stimulate a response in the patient by applying increasing levels of energy to form a substantially continuous broadcast field between the plurality of anodes and cathodes on the upper surface such that the broadcast field is formed by adjacent bipole pairs of anodes and cathodes which share alternating anodes, to determine the first stimulation level at which the nerve responds;
    determining a threshold amount of energy required to stimulate a response in the patient from a plurality of anodes and cathodes on the lower surface of the device by applying energy to form a substantially continuous broadcast field from the lower surface; and
    determining if the nerve is closer to the upper or lower surface regions by comparing the threshold amounts from the upper surface and the lower surface.

2. The method of claim 1, wherein the step of determining a threshold amount of energy required to stimulate a response in the patient comprises determining the threshold current required to stimulate an EMG response in the patient.

3. The method of claim 1, wherein the step of positioning the device comprises positioning a device that is substantially flat, having a first major side on the upper surface and a second major side on the lower surface.

4. The method of claim 1, wherein the step of positioning the device comprises moving the device over the guidewire.

5. The method of claim 1, wherein the step of positioning the guidewire comprises passing the guidewire from outside of the patient, through a neural foramen, and out of the patient, so that both ends of the guidewire extend from the patient.

6. The method of claim 1, wherein the step of determining a threshold amount of energy required to stimulate a response in the patient comprises incrementally increasing the current applied to the plurality of anodes and cathodes to form the substantially continuous broadcast field.

7. A method of detecting if a nerve is above or below a given region of a device in a tissue, the method comprising:
    positioning a device within the tissue so that an upper surface of the device faces the dorsal region of the patient and a lower surface of the device faces ventral region of the patient, wherein the device comprises a flexible elongate body having a first plurality of anodes and cathodes on the upper surface and a second plurality of anodes and cathodes on the lower surface;
    determining a threshold amount of energy required to stimulate a response in the patient from the upper surface by applying increasing levels of energy to form a substantially continuous broadcast field along the upper surface between the first plurality of anodes and cathodes such that the broadcast field is formed by adjacent bipole pairs of anodes and cathodes which share alternating anodes and cathodes, to determine the first stimulation level at which the nerve responds;
    determining a threshold amount of energy required to stimulate a response in the patient from the lower surface by applying increasing levels of energy to form a substantially continuous broadcast field along the lower surface between the second plurality of anodes and cathodes such that the broadcast field is formed by adjacent bipole pairs of anodes and cathodes which share alternating anodes and cathodes, to determine the first stimulation level at which the nerve responds;
    determining the location of the nerve relative to the upper and lower surfaces by comparing the threshold amounts.

8. The method of claim 7, further comprising moving the device over a guidewire.

9. The method of claim 7, further comprising positioning a guidewire by passing the guidewire from outside of the patient, through a neural foramen, and out of the patient, so that both ends of the guidewire extend from the patient.

10. The method of claim 7, wherein the steps of determining a threshold amount of energy required to stimulate a response in the patient from the upper and lower surfaces comprises determining the threshold current required to stimulate an EMG response in the patient.

11. The method of claim 7, further comprising confirming that a nerve is ventral to the device by comparing the threshold amounts from the upper and lower surfaces.

12. The method of claim 7, further comprising positioning a guidewire within the tissue by passing the guidewire through a lumen in the device.

13. The method of claim 12, wherein the step of positioning the guidewire comprises passing the guidewire through the device.

* * * * *